(12) United States Patent
Schneider et al.

(10) Patent No.: US 7,884,185 B2
(45) Date of Patent: Feb. 8, 2011

(54) HYDROGELS AND USES THEREOF

(75) Inventors: Joel P. Schneider, Newark, DE (US); Darrin J. Pochan, Landenberg, PA (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 10/900,344

(22) Filed: Jul. 28, 2004

(65) Prior Publication Data

US 2006/0025524 A1  Feb. 2, 2006

(51) Int. Cl.
A61K 38/10 (2006.01)
A61K 38/16 (2006.01)

(52) U.S. Cl. ............... 530/326; 530/300; 530/350

(58) Field of Classification Search ............ 525/54, 525/54.1, 54.11; 530/300, 326, 350
See application file for complete search history.

(56) References Cited

U.S. PATENT DOCUMENTS

| | | | | |
|---|---|---|---|---|
| 5,134,057 A | * | 7/1992 | Kuypers et al. | 430/325 |
| 5,662,899 A | * | 9/1997 | Chokri et al. | 424/93.7 |
| 5,807,757 A | * | 9/1998 | Andrianov et al. | 436/535 |
| 5,965,532 A | * | 10/1999 | Bachovchin | 514/12 |

FOREIGN PATENT DOCUMENTS

WO WO 01/37896 5/2001

OTHER PUBLICATIONS

Kisiday et al., PNAS Jul. 23, 2002, vol. 99, No. 15, pp. 9996-10001.*
Schneider et al., JACS 2002, 124, 15030-15037.*
Pochan et al., JACS 2003, 125, 11802-11803.*
Rajagopal, Karthikan, et al.; "Self-Assembling Peptides and Proteins for Nanotechnological Applications"; Curr. Opinion in Struct. Bio.; 2004; vol. 14; pp. 480-486.
Ozbas, et al., "Salt-Triggered Peptide Folding and Consequent Self-Assembly Into Hydrogels With Tunable Modulus", Macromolecules, 2004, vol. 37, pp. 7331-7337.
Petka, et al., "Reversible Hydrogels from Self-Assembling Artificial Proteins", Science, Jul. 17, 1998, vol. 281, pp. 389-392.
McMillan, et al., "Synthesis and Characterization of Elastin-Mimetic Protein Gels Derived from a Well-Defined Polypeptide Precursor", Macromolecules, 2000, vol. 33, pp. 4809-4821.
Caplan, et al., "Self-Assembly of a β-Sheet Protein Governed by Relief of Electrostatic Repulsion Relative to van der Waals Attraction", Biomacromolecules, 2000, vol. 1, pp. 627-631.
Wang, et al., "Hybrid Hydrogels Assembled from Synthetic Polymers and Coiled-Coil Protein Domains", Nature, 1999, vol. 397, pp. 417-420.
Schneider, et al., Responsive Hydrogels from the Intramolecular Folding and Self-Assembly of a Designed Peptide, *J. Am. Chem Soc.* 2002 124, 15030, Dept. of Chemistry and Biochemistry and Materials Science and Engineering and the Delaware Biotechnology Inst., University of DE, Newark, DE.
Pochan, et al., Thermally Reversible Hydrogels Via Intramolecular Folding and Consequent Self-Assembly of a *de novo* Designed Peptide, *J. Am. Chem. Soc.* 2003, 125, 11802., Dept. of Materials Science and Engineering and the Delaware Biotechnology Inst., and Chemistry and Biochemistry, University of DE, Newark.
Ohnishi, et al., The Roles of Turn Formation and Cross-Strand Interactions in Fibrillization of Peptides Derived From The Ospa Single-Layer B-Sheet, Dept. of Biochemistry and Biophysics, Univ. of Rochester Medical Center, New York.
Münoz, et al., A Statistical Mechanical Model for B-Hairpin Kinetics, Laboratory of Chemical Physics, Building 5, National Institute of Diabetes and Digestive and Kidney Diseases, National Institutes of Health, Bethesda, MD.
Tran, Thao; "PCT International Search Report, Written Opinion"; Mar. 8, 2007; 7 pp; USPTO(PCT), Alexandria, VA, US.
Niaounakis, Michael; "Supplementary European Search Report"; Mar. 4, 2010; 8 pp; Rijswijk, The Netherlands.
Komsa-Penkova, Regina; "Thermal Stability of Calf Skin Collagen Type I in Salt Solutions"; Biochimica et Biophysica Acta; Jun. 3, 1996; pp. 171-181; Issue 1297; Elsevier Science B.V.

* cited by examiner

*Primary Examiner*—Thao T. Tran
(74) *Attorney, Agent, or Firm*—RatnerPrestia

(57) ABSTRACT

The present invention provides novel hydrogels and methods of making and using such hydrogels. The present invention provides hydrogels that may be formed by the self-assembly of peptides in solution. Such self-assembly may be brought about by a change in one or more characteristics of the solution. Characteristics of the solution that may be changed include pH, ionic strength, temperature, and concentration of one or more specific ions. In addition, hydrogels of the invention may be disassembled by changing one or more characteristic of the hydrogel such as pH, ionic strength, temperature, and concentration of one or more specific ions.

18 Claims, 26 Drawing Sheets

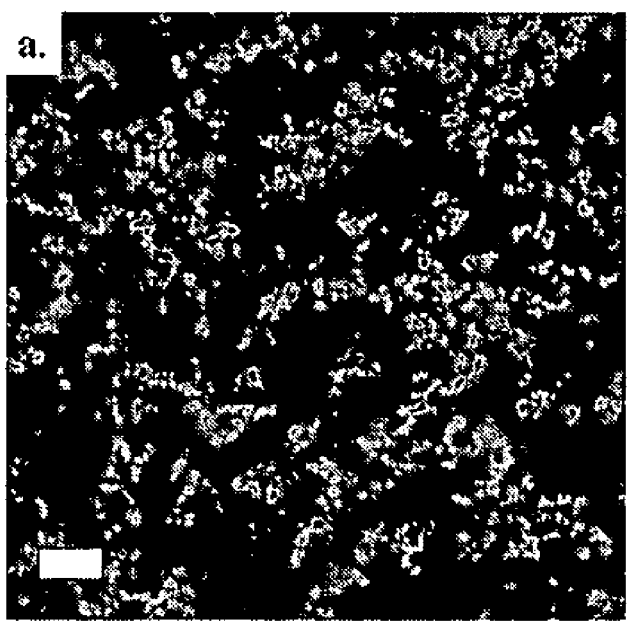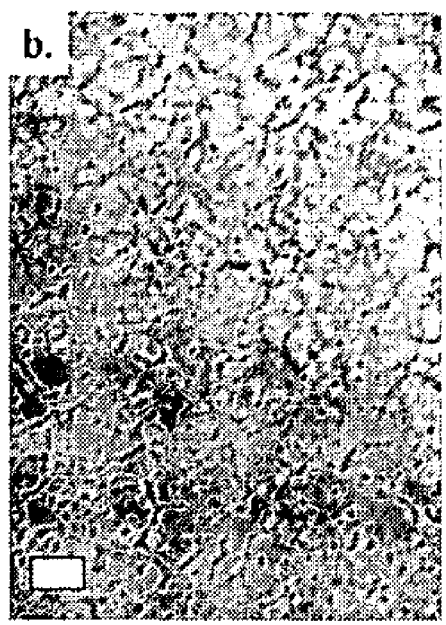
Figure 7A Figure 7B

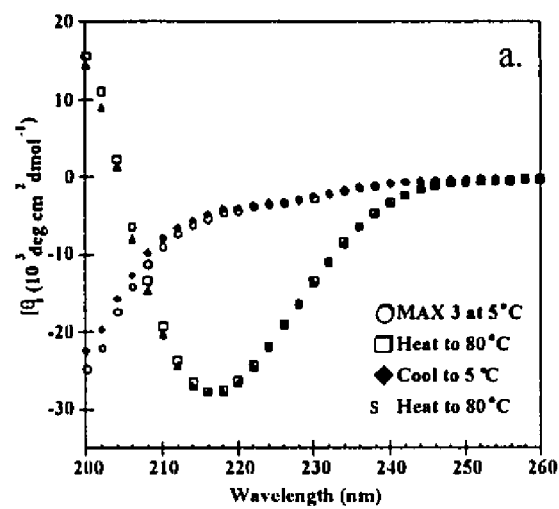 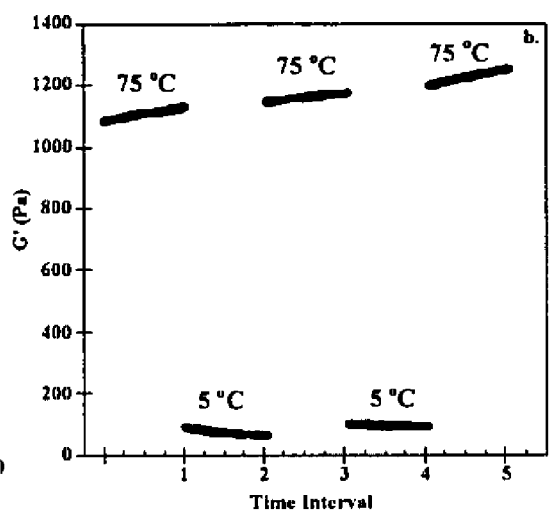
Figure 10A Figure 10B

Figure 11A
Figure 11B
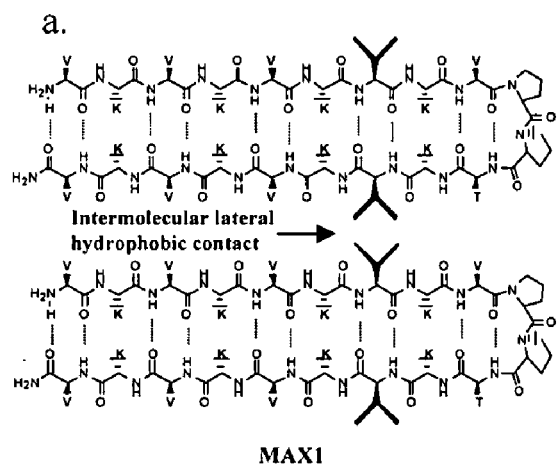
MAX1
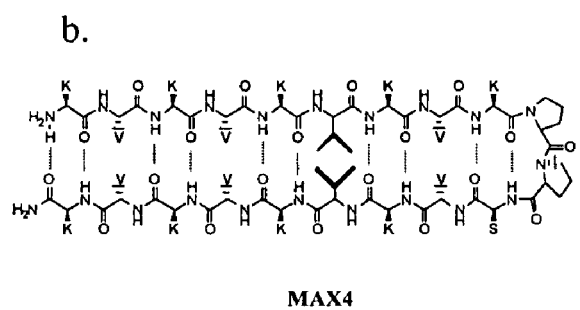
MAX4

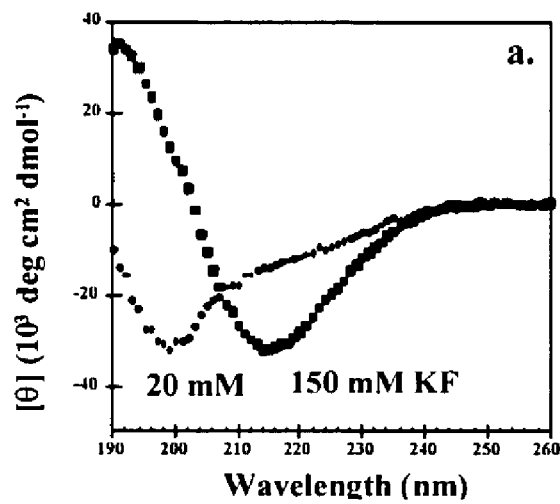 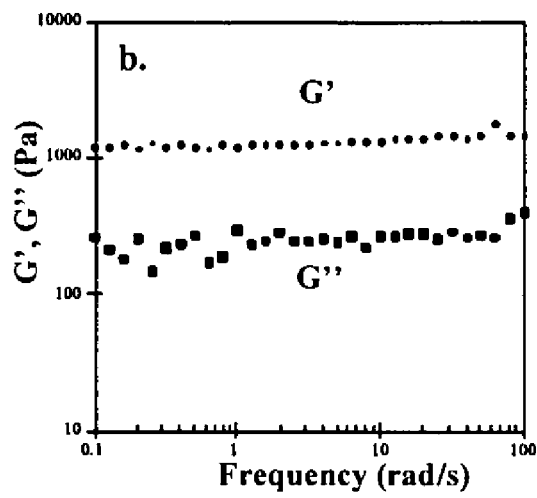
Figure 14A  Figure 14B

Figure 16A  Figure 16C  Figure 16E
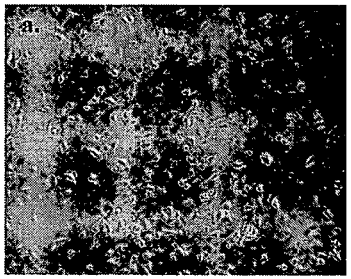 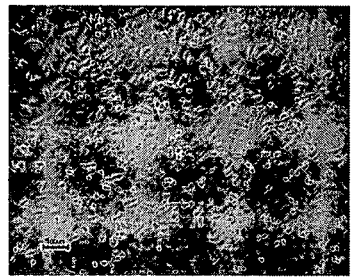 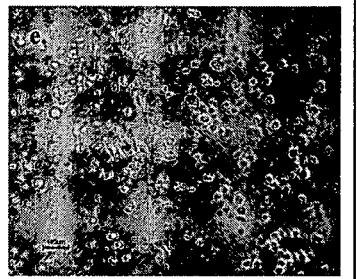
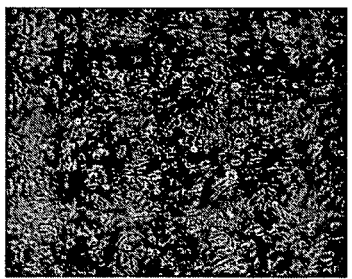 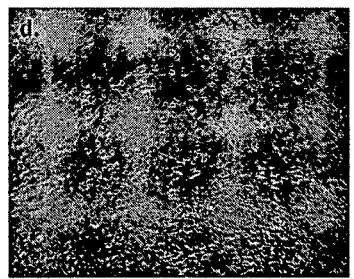 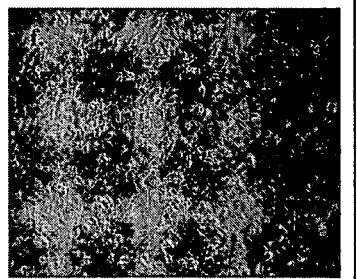
Figure 16B  Figure 16D  Figure 16F

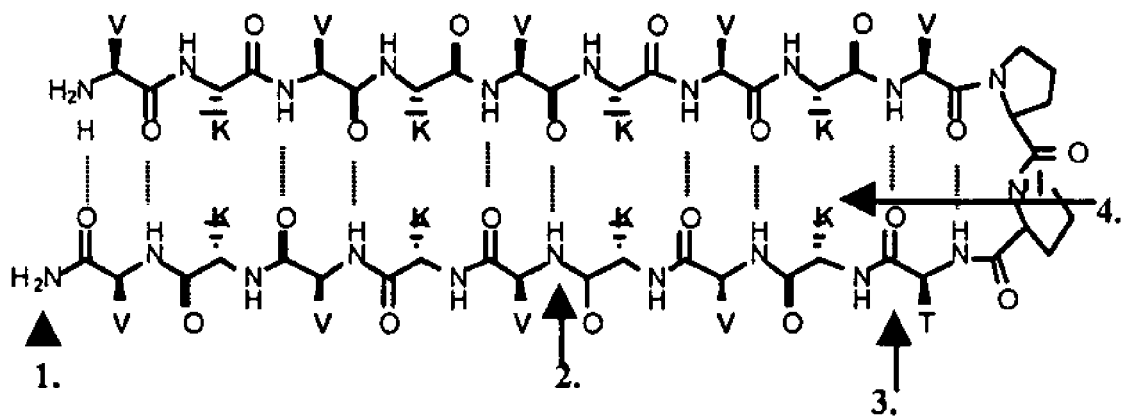
1. Append RGD at one or both ends
2. Insert RGD in middle of one or both strands
3. Insert RGD at one or both turn flanking positions
4. Covently attach RGD onto lysine side chain(s) e.g.
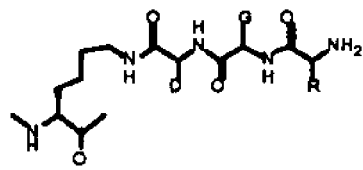
Figure 19.

| Trigger | Modification |
|---|---|
| 1. hv(330-360 nm) | Replace Val(16) with |
| 2. hv(330-360 nm) | Modify Val(16) amide as |
| 3. Ca(II) binding | Replace -V<sup>D</sup>PPT- turn with calcium binding loop region of Troponin C (–DRKADGYIDFEE-) |
| 4. Ca(II) binding | Replace -V<sup>D</sup>PPT- turn with DOTAM |

SEQUENCE LISTING

<160> NUMBER OF SEQ ID NOS: 20

<210> SEQ ID NO 1
<211> LENGTH: 20
<212> TYPE: PRT
<213> ORGANISM: Artificial
<220> FEATURE:
<223> OTHER INFORMATION: synthetic peptide sequence

<400> SEQUENCE: 1

Val Lys Val Lys Val Lys Val Lys Val Pro Pro Thr Lys Val Lys Val
1               5                   10                  15

Lys Val Lys Val
            20

<210> SEQ ID NO 2
<211> LENGTH: 20
<212> TYPE: PRT
<213> ORGANISM: Artificial
<220> FEATURE:
<223> OTHER INFORMATION: synthetic peptide sequence

<400> SEQUENCE: 2

Val Lys Val Lys Val Lys Val Lys Tyr Asn Gly Thr Lys Val Lys Val
1               5                   10                  15

```
Lys Val Lys Val
            20

<210> SEQ ID NO 3
<211> LENGTH: 20
<212> TYPE: PRT
<213> ORGANISM: Artificial
<220> FEATURE:
<223> OTHER INFORMATION: synthetic peptide sequence

<400> SEQUENCE: 3

Val Lys Val Lys Val Lys Val Lys Gly Gly Gly Gly Lys Val Lys Val
1               5                   10                  15

Lys Val Lys Val
            20

<210> SEQ ID NO 4
<211> LENGTH: 20
<212> TYPE: PRT
<213> ORGANISM: Artificial
<220> FEATURE:
<223> OTHER INFORMATION: synthetic peptide sequence

<400> SEQUENCE: 4

Val Lys Val Lys Val Lys Val Lys Val Arg Gly Asp Lys Val Lys Val
1               5                   10                  15

Lys Val Lys Val
            20

<210> SEQ ID NO 5
<211> LENGTH: 30
<212> TYPE: PRT
<213> ORGANISM: Artificial
<220> FEATURE:
<223> OTHER INFORMATION: synthetic peptide sequence
<220> FEATURE:
<221> NAME/KEY: MISC_FEATURE
<222> LOCATION: (9)..(12)
<223> OTHER INFORMATION: Xaa can be any natural or non-natural amino
      acid or analog
<220> FEATURE:
<221> NAME/KEY: MISC_FEATURE
<222> LOCATION: (19)..(22)
<223> OTHER INFORMATION: Xaa can be any natural or non-natural amino
      acid or analog

<400> SEQUENCE: 5

Val Lys Val Lys Val Lys Val Lys Xaa Xaa Xaa Xaa Lys Val Lys Val
1               5                   10                  15

Lys Val Xaa Xaa Xaa Xaa Lys Val Lys Val Lys Val Lys Val
            20                  25                  30

<210> SEQ ID NO 6
<211> LENGTH: 4
<212> TYPE: PRT
<213> ORGANISM: Artificial
<220> FEATURE:
<223> OTHER INFORMATION: beta turn sequence

<400> SEQUENCE: 6

Lys Asn Gly Lys
1

<210> SEQ ID NO 7
<211> LENGTH: 4
<212> TYPE: PRT
<213> ORGANISM: Artificial
```

```
<220> FEATURE:
<223> OTHER INFORMATION: beta turn sequence

<400> SEQUENCE: 7

Val Asn Gly Thr
1

<210> SEQ ID NO 8
<211> LENGTH: 8
<212> TYPE: PRT
<213> ORGANISM: Artificial
<220> FEATURE:
<223> OTHER INFORMATION: synthetic peptide sequence
<220> FEATURE:
<221> NAME/KEY: MISC_FEATURE
<222> LOCATION: (1)..(2)
<223> OTHER INFORMATION: residues 1 and 2 may be repeated from 1 to 100
      times
<220> FEATURE:
<221> NAME/KEY: MISC_FEATURE
<222> LOCATION: (7)..(8)
<223> OTHER INFORMATION: residues 7 and 8 may be repeated from 1 to 100
      times

<400> SEQUENCE: 8

Val Lys Val Pro Pro Thr Lys Val
1               5

<210> SEQ ID NO 9
<211> LENGTH: 8
<212> TYPE: PRT
<213> ORGANISM: Artificial
<220> FEATURE:
<223> OTHER INFORMATION: synthetic peptide sequence
<220> FEATURE:
<221> NAME/KEY: MISC_FEATURE
<222> LOCATION: (1)..(2)
<223> OTHER INFORMATION: residues 1 and 2 may be repeated from 1 to 100
      times
<220> FEATURE:
<221> NAME/KEY: MISC_FEATURE
<222> LOCATION: (7)..(8)
<223> OTHER INFORMATION: residues 7 and 8 may be repeated from 1 to 100
      times

<400> SEQUENCE: 9

Val Lys Gly Gly Gly Gly Lys Val
1               5

<210> SEQ ID NO 10
<211> LENGTH: 8
<212> TYPE: PRT
<213> ORGANISM: Artificial
<220> FEATURE:
<223> OTHER INFORMATION: synthetic peptide sequence
<220> FEATURE:
<221> NAME/KEY: MISC_FEATURE
<222> LOCATION: (1)..(2)
<223> OTHER INFORMATION: residues 1 and 2 may be repeated from 1 to 100
      times
<220> FEATURE:
<221> NAME/KEY: MISC_FEATURE
<222> LOCATION: (7)..(8)
<223> OTHER INFORMATION: residues 7 and 8 may be repeated from 1 to 100
      times

<400> SEQUENCE: 10

Val Lys Tyr Asn Gly Thr Lys Val
1               5

<210> SEQ ID NO 11
```

```
<211> LENGTH: 8
<212> TYPE: PRT
<213> ORGANISM: Artificial
<220> FEATURE:
<223> OTHER INFORMATION: synthetic peptide sequence
<220> FEATURE:
<221> NAME/KEY: MISC_FEATURE
<222> LOCATION: (1)..(2)
<223> OTHER INFORMATION: residues 1 and 2 may be repeated from 1 to 100
      times
<220> FEATURE:
<221> NAME/KEY: MISC_FEATURE
<222> LOCATION: (7)..(8)
<223> OTHER INFORMATION: residues 7 and 8 may be repeated from 1 to 100
      times

<400> SEQUENCE: 11

Val Lys Val Arg Gly Asp Lys Val
1               5

<210> SEQ ID NO 12
<211> LENGTH: 20
<212> TYPE: PRT
<213> ORGANISM: Artificial
<220> FEATURE:
<223> OTHER INFORMATION: synthetic peptide sequence
<220> FEATURE:
<221> NAME/KEY: MISC_FEATURE
<222> LOCATION: (9)..(12)
<223> OTHER INFORMATION: Xaa may be any natural or non-natural amino
      acid or analog

<400> SEQUENCE: 12

Val Lys Val Lys Val Lys Val Lys Xaa Xaa Xaa Xaa Lys Val Lys Val
1               5                   10                  15

Lys Val Lys Val
            20

<210> SEQ ID NO 13
<211> LENGTH: 4
<212> TYPE: PRT
<213> ORGANISM: Artificial
<220> FEATURE:
<223> OTHER INFORMATION: turn sequence

<400> SEQUENCE: 13

Val Gly Gly Thr
1

<210> SEQ ID NO 14
<211> LENGTH: 30
<212> TYPE: PRT
<213> ORGANISM: Artificial
<220> FEATURE:
<223> OTHER INFORMATION: synthetic peptide sequence

<400> SEQUENCE: 14

Val Lys Val Lys Val Lys Val Lys Val Asp Arg Lys Ala Asp Gly Tyr
1               5                   10                  15

Ile Asp Phe Glu Glu Val Lys Val Lys Val Lys Val Lys Val
            20                  25                  30

<210> SEQ ID NO 15
<211> LENGTH: 6
<212> TYPE: PRT
<213> ORGANISM: Artificial
<220> FEATURE:
<223> OTHER INFORMATION: synthetic peptide sequence
```

```
<400> SEQUENCE: 15

Thr Arg Gly Asp Ser Pro
1               5

<210> SEQ ID NO 16
<211> LENGTH: 4
<212> TYPE: PRT
<213> ORGANISM: Artificial
<220> FEATURE:
<223> OTHER INFORMATION: synthetic peptide sequence

<400> SEQUENCE: 16

Arg Gly Asp Gly
1

<210> SEQ ID NO 17
<211> LENGTH: 4
<212> TYPE: PRT
<213> ORGANISM: Artificial
<220> FEATURE:
<223> OTHER INFORMATION: synthetic peptide sequence

<400> SEQUENCE: 17

Arg Gly Asp Tyr
1

<210> SEQ ID NO 18
<211> LENGTH: 4
<212> TYPE: PRT
<213> ORGANISM: Artificial
<220> FEATURE:
<223> OTHER INFORMATION: synthetic peptide sequence

<400> SEQUENCE: 18

Arg Gly Asp Trp
1

<210> SEQ ID NO 19
<211> LENGTH: 7
<212> TYPE: PRT
<213> ORGANISM: Artificial
<220> FEATURE:
<223> OTHER INFORMATION: synthetic peptide sequence

<400> SEQUENCE: 19

Phe His Arg Arg Ile Lys Ala
1               5

<210> SEQ ID NO 20
<211> LENGTH: 7
<212> TYPE: PRT
<213> ORGANISM: Artificial
<220> FEATURE:
<223> OTHER INFORMATION: synthetic peptide sequence

<400> SEQUENCE: 20

Gly Arg Gly Asp Ser Pro Tyr
1               5
```

HYDROGELS AND USES THEREOF

This work was supported in part by NIH grant no. 1 P20 RR17716-01. The U.S. Government may have certain rights to the present invention.

BACKGROUND OF THE INVENTION

Hydrogels are a class of materials that have significant promise for use in soft tissue and bone engineering. The general characteristic of hydrogels that make them important materials for these applications are their well hydrated, porous structure. The present invention provides a new class of environmentally responsive peptide-based hydrogels that fulfill critical material requirements not currently met with existing technology. Hydrogels of the invention may be designed to be compatible with the adhesion and proliferation of various cell types, e.g., fibroblasts and osteoblasts, making them potential tissue engineering scaffolds for generating connective tissue and bone. There is a demanding set of biological and material properties required of hydrogels for use in tissue regeneration. Irrespective of ultimate target tissue type, a hydrogel must exhibit a general set of biological properties. First, the material must be cytocompatible. Cytocompatibility, defined herein, means that the hydrogel must not be cytotoxic to desired cells. Second, the material must be biocompatible. Biocompatible, defined herein, means that a scaffold does not cause a significant immunological and inflammatory response if placed in vivo for tissue regeneration and is preferably biodegradable affording non-toxic species. The present invention relates to the development of new materials using novel self-assembly methodology and the assessment of resultant material cytocompatibility.

Desired material properties are challenging to comprehensively incorporate into any one material since some desired properties are seemingly mutually exclusive. For example, the morphology of an ideal hydrogel contains a high level of porosity (spanning nanoscale to microscale dimensions) for cell motility and nutrient/waste diffusion. Also, the hydrogel should primarily be composed of aqueous media with as little solid material as possible in order to allow ample volume for cell proliferation and ease of eventual scaffold biodegradation. However, despite their dilute, porous nature, these well hydrated materials must also be mechanically rigid. This apparent contradiction, rigidity from a dilute porous scaffold, must be inherently addressed by the design of constituent molecular crosslinks (chemical and/or physical) formed during the hydrogelation process. However, introducing chemical crosslinks may be biologically problematic since by-products from the crosslinking chemistry may be toxic and difficult to remove from the scaffold. Ideally, benign, biocompatible chemical or physical crosslinking methods should be used for either in vitro gelation for eventual incorporation in the body or direct, rapid in vivo gelation where formation of crosslinks are triggered by physiological stimuli (temperature, ionic strength, pH, etc). The idea of using environmental triggers to initiate material formation via self-assembly is being actively pursued. For example, it has been shown that peptide self-assembly (and thus gelation) can be triggered by the release of salt from temperature and light sensitive liposomes (Collier, et al., *Journal of the American Chemical Society* 2001, 123, 9463-9464). An additional design complication is that hydrogel rigidity seemingly precludes any viable processibility in preformed scaffolds. For example, one may wish to form a rigid tissue engineering construct in vitro but subsequently inject it into a host for tissue regeneration. Injection is not possible in a permanently crosslinked, rigid network.

Current hydrogel technology utilizes both naturally-derived macromolecules and synthetic polymers. Generally, hydrogels prepared from natural polymers exhibit favorable biological properties but may lack desired material properties, e.g. low sample rigidity. In contrast, synthetic polymers can be engineered for desired material properties but may display limited cytocompatibility. A common approach to increase the cytocompatibility of synthetic polymers is to incorporate peptide epitopes, for example RGD motifs. However, incorporating these motifs into preformed polymers in a regiospecifically controlled manner is extremely difficult to impossible. As a result, controlling the material properties of the polymers is problematic. For example, controlling the concentration of an epitope displayed on the surface for cell adhesion or controlling the accessibility of the epitopes is a challenge. In addition, these scaffolds are structurally homogeneous (not porous) on the microscale due to their underlying molecular network structure, which can limit cell proliferation. These systems must undergo additional processing (e.g. freeze-thaw cycling, particulate leaching, microsphere sintering and non-woven fiber formation) in order to introduce microscale porosity in the gel network. In short, there is currently no single hydrogel system that successfully incorporates all requisite properties of an ideal tissue engineering scaffold.

An opportunity and need exists for the design of novel hydrogel scaffold strategies. There remains a need for rigid, porous, easily processed, cytocompatible hydrogels that can be rapidly formed in vitro or in vivo.

SUMMARY OF THE INVENTION

The present invention provides novel hydrogels. In addition, the present invention provides a novel process for the construction of hydrogels. As used herein, the term hydrogel means a dilute interconnected scaffold, preferably encapsulating a large volume fraction of water and mechanically self-supporting. As used herein, the term hydrogel also encompasses dilute interconnected scaffolds encompassing aqueous organic mixtures and/or organic solvents (e.g., DMF, DMSO, etc.). In one aspect, the present invention provides a combination of a new process and novel peptides to construct a smart hydrogelation system. Novel peptides (for example, MAX1) have been designed to undergo a change in secondary structure in response to one or more environmental signals or stimuli (e.g., changes in one or more environmental characteristics). In one particular aspect, peptides of the invention may be in aqueous solution and one or more parameters of the solution may be altered in order to induce a change in secondary structure of the peptides. In specific embodiments, one or more of pH, ionic strength, specific ion concentration, and/or temperature of the solution may be altered and may induce a change in the secondary structure of the peptides. Typically, after the peptides have undergone a change in secondary structure as a result of a change in one or more parameter of the solution, the peptides will assemble into a higher order structure, e.g., a hydrogel. In another aspect of the invention, an environmental signal may involve electromagnetic radiation, e.g., light. For example, a peptide of the invention may undergo a structural change, which may be a change in primary structure, secondary structure or both, as a result of being subjected to electromagnetic radiation. Typically, after being exposed to electromagnetic radiation, peptides embodying this aspect of the invention will assume a desired secondary structure and self-assemble into a higher order structure, e.g., a hydrogel.

In one aspect, the transition from a low viscosity aqueous solution to a rigid hydrogel material (essentially an infinite change in viscosity) via a self-assembly mechanism is preferably predicated on individual peptides folding into a desired conformation. This intramolecular folding process can be controlled to occur only with a desired environmental signal. Environmental signals include, but are not limited to, physiological solution conditions (37 degrees Celsius, pH7.4, and high salt concentration). Due to robust, chemically benign gelation at physiological conditions, these gels have major potential in the field of tissue engineering and wound healing.

In one particular embodiment, peptides may be designed to adopt a β-hairpin secondary structure in response to one or more environmental signals. Typically, after adopting a β-hairpin structure, peptides will self-assemble into a higher order structure, for example a three dimensional network and, consequently, a hydrogel. In one aspect, the self-assembly does not take place unless side chains on the peptide molecules are uniquely presented in the β-hairpin conformation.

Thus, in one aspect, the present invention provides a process for designing peptides to adopt a desired secondary structure in response to one or more environmental stimuli. Further, the present invention provides a process for designing a peptide that will form a higher order structure, e.g., a hydrogel, in response to one or more environmental stimuli. The present invention also encompasses the higher order structures thus formed, e.g., hydrogels.

In some aspects, the adoption of a secondary structure and the formation of a higher order structure are linked. Thus, peptide folding and self-assembly (e.g., gelation) are linked. This aspect of the invention allows the control of gelation. In particular, this aspect permits the control of the kinetics of hydrogel formation (i.e., how fast a gel is formed). Also, control of the self-assembly process allows control of the physical characteristics of the hydrogel thus formed (e.g., the stiffness of the resulting gel). Peptides may be designed and/or environmental stimuli may be chosen such that, after application of one or more environmental stimuli, hydrogel formation may take from about 1 second to about 5 hours, from about 1 second to about 4 hours, from about 1 second to about 3 hours, from about 1 second to about 2 hours, from about 1 second to about 1 hour, from about 1 second to about 50 minutes, from about 1 second to about 40 minutes, from about 1 second to about 30 minutes, from about 1 second to about 20 minutes, from about 1 second to about 15 minutes, from about 1 second to about 10 minutes, from about 1 second to about 5 minutes, from about 1 second to about 2 minutes, from about 10 seconds to about 5 hours, from about 10 seconds to about 4 hours, from about 10 seconds to about 3 hours, from about 10 seconds to about 2 hours, from about 10 seconds to about 1 hour, from about 10 seconds to about 50 minutes, from about 10 seconds to about 40 minutes, from about 10 seconds to about 30 minutes, from about 10 seconds to about 20 minutes, from about 10 seconds to about 15 minutes, from about 10 seconds to about 10 minutes, from about 10 seconds to about 5 minutes, from about 10 seconds to about 2 minutes, from about 30 seconds to about 5 hours, from about 30 seconds to about 4 hours, from about 30 seconds to about 3 hours, from about 30 seconds to about 2 hours, from about 30 seconds to about 1 hour, from about 30 seconds to about 50 minutes, from about 30 seconds to about 40 minutes, from about 30 seconds to about 30 minutes, from about 30 seconds to about 20 minutes, from about 30 seconds to about 15 minutes, from about 30 seconds to about 10 minutes, from about 30 seconds to about 5 minutes, from about 30 seconds to about 2 minutes, from about 60 seconds to about 5 hours, from about 60 seconds to about 4 hours, from about 60 seconds to about 3 hours, from about 60 seconds to about 2 hours, from about 60 seconds to about 1 hour, from about 60 seconds to about 50 minutes, from about 60 seconds to about 40 minutes, from about 60 seconds to about 30 minutes, from about 60 seconds to about 20 minutes, from about 60 seconds to about 15 minutes, from about 60 seconds to about 10 minutes, from about 60 seconds to about 5 minutes, or from about 60 seconds to about 2 minutes.

Hydrogels formed according to the invention may have varying amounts of solid material. For example, hydrogels may be formed comprising a percent by weight of peptide of from about 0.1% to about 10.0%, from about 0.1% to about 9.0%, from about 0.1% to about 8.0%, from about 0.1% to about 7.0%, from about 0.1% to about 6.0%, from about 0.1% to about 5.0%, from about 0.1% to about 4.0%, from about 0.1% to about 3.0%, from about 0.1% to about 2.0%, from about 0.1% to about 1.0%, from about 0.1% to about 0.75%, from about 0.1% to about 0.5%, from about 0.1% to about 0.25%, from about 0.25% to about 10.0%, from about 0.25% to about 9.0%, from about 0.25% to about 8.0%, from about 0.25% to about 7.0%, from about 0.25% to about 6.0%, from about 0.25% to about 5.0%, from about 0.25% to about 4.0%, from about 0.25% to about 3.0%, from about 0.25% to about 2.0%, from about 0.25% to about 1.0%, from about 0.25% to about 0.75%, from about 0.25% to about 0.5%, from about 0.5% to about 10.0%, from about 0.5% to about 9.0%, from about 0.5% to about 8.0%, from about 0.5% to about 7.0%, from about 0.5% to about 6.0%, from about 0.5% to about 5.0%, from about 0.5% to about 4.0%, from about 0.5% to about 3.0%, from about 0.5% to about 2.0%, from about 0.5% to about 1.0%, from about 0.5% to about 0.75%, from about 1.0% to about 10.0%, from about 1.0% to about 9.0%, from about 1.0% to about 8.0%, from about 1.0% to about 7.0%, from about 1.0% to about 6.0%, from about 1.0% to about 5.0%, from about 1.0% to about 4.0%, from about 1.0% to about 3.0%, from about 1.0% to about 2.0%, or from about 1.0% to about 1.5%.

In one aspect, the amount by weight of peptide and the kinetics of gelation may be varied to produce a hydrogel having a desired modulus (stiffness). Hydrogels of the invention may have a modulus from about 1 Pascal (Pa) to about 100,000 Pa, from about 1 Pa to about 50,000 Pa, from about 1 Pa to about 25,000 Pa, from about 1 Pa to about 10,000 Pa, from about 1 Pa to about 7,500 Pa, from about 1 Pa to about 5,000 Pa, from about 1 Pa to about 2,500 Pa, from about 1 Pa to about 2,000 Pa, from about 1 Pa to about 1,500 Pa, from about 1 Pa to about 1,000 Pa, from about 1 Pa to about 500 Pa, from about 1 Pa to about 250 Pa, from about 1 Pa to about 100 Pa, from about 100 Pa to about 100,000 Pa, from about 100 Pa to about 50,000 Pa, from about 100 Pa to about 25,000 Pa, from about 100 Pa to about 10,000 Pa, from about 100 Pa to about 7,500 Pa, from about 100 Pa to about 5,000 Pa, from about 100 Pa to about 2,500 Pa, from about 100 Pa to about 2,000 Pa, from about 100 Pa to about 1,500 Pa, from about 100 Pa to about 1,000 Pa, from about 100 Pa to about 500 Pa, or from about 100 Pa to about 250 Pa.

In one aspect of the invention, the hydrogels formed may be processed. For example, hydrogels of the invention may be injected into an animal (e.g., mammal). Since hydrogels of the invention self-assemble, one can easily process the stiff gel (e.g. inject through a syringe) while it immediately reassembles/stiffens after the cessation of processing. In a related aspect, hydrogels may be formed physically via self-assembly from a low viscosity solution, thus, hydrogels may be produced in restrictive geometries, in vitro or in vivo.

In some preferred embodiments, peptide-based hydrogels of the invention are completely noncytotoxic and may also promote the adhesion and proliferation of common mammalian cells (e.g. fibroblasts, osteoblasts). Thus, hydrogels of the invention may be used in the culture of cells. Cell cultures can be encapsulated in three dimensions due to self-assembly mechanism thus allowing 3-D cell attachment and proliferation. In some embodiments, hydrogels may be used as three-dimensional supports to grow/maintain cells lines that have been engineered to produce therapeutics such as pharmaceutical compounds, peptides, proteins, antibodies and the like. Continuous flow of media through a bioreactor containing hydrogel and cells affords rapid isolation of compounds and a means of continual cell proliferation.

In some aspects, hydrogels prepared from peptides of the invention (e.g., MAX-1 and related hairpin peptides) exhibit antimicrobial behavior against gram positive and gram negative bacteria. Therefore, hydrogels of the invention may be antimicrobial in a clinical setting. This characteristic of hydrogels of the invention will make them useful in situations in which the hydrogel is to be placed inside a living animal (e.g., a mammal such as a human) as well in methods of culturing cells. In a particular embodiment, hydrogels of the invention may be used for tissue engineering. For example, a desired quantity of one or more types of cell may be placed in solution with one or more peptides of the invention. The cell containing solution may be caused to form a hydrogel in which the cells may be dispersed throughout the hydrogel. The cell containing hydrogel may then be used as tissue, for example, to replace a damaged tissue. The antimicrobial character of the hydrogels of the invention will help to prevent infection when introduced into an animal. In some embodiments, the hydrogels of the invention may be constructed to undergo reversible gelation, i.e., to form a hydrogel under one set of conditions and then go back into solution under other conditions. This may be used in tissue engineering application such that cells may introduced in a hydrogel scaffolding that eventually dissolves leaving the cells in place. Antimicrobial gels will also be useful in wound healing applications. Hydrogels for use in wound healing applications may comprise therapeutic agents in addition to the hydrogel. For example, a solution of peptides that undergo hydrogel formation when placed in physiological conditions (i.e., in contact with a wound) may comprise agents to promote coagulation, analgesics and/or other therapeutic agents.

In some aspects, hydrogels of the invention may be readily functionalized with further biochemistry (e.g. growth factor or cell adhesion peptide epitopes) for further optimization. Thus, peptides of the invention may comprise additional components, which may be peptides, that give the hydrogels of the invention varying characteristics.

Hydrogels of the invention may be used in microfluidic devices as environmentally responsive barrier materials. For example, the channels of a microfluidic devices can flooded with an aqueous solution of peptide. Hydrogelation can initiated with spatial resolution to install channel barriers at desired locations. These barriers or dams can act as sensing devices. When solution passes over them which causes hydrogel dissolution (dam destruction), nascent channels are opened allowing fluid to flow to detectors, providing the means of detection of analyte. The dissolution of hydrogel barriers can also be used to initiate and facilitate mixing of reacting components for desired chemical transformations and reactions.

The hydrogels of the invention may be used as sensors for the detection of one or more analyte of interest. For example, a solution of peptides of the invention may be contacted with a sample that may contain the analyte. In some instances, presence of the analyte may induce gelation of the solution. For example, the analyte of interest may be a metal ion and contact of the solution of peptides with the metal ion may result in gelation of the solution. In other instances, a hydrogel of the invention may be formed and then contacted with a sample that may contain the analyte of interest. The presence of the analyte may result solubilizing the hydrogel. The detection of the formation or dissolution of hydrogel may be accomplished using standard techniques well known to one of ordinary skill in the art, for example, optical techniques.

In some embodiments, hydrogels of the invention may be used to prepare matrices for separation of molecules of interest (e.g., biomolecules, proteins, DNA, RNA, etc.). Peptides may be designed to have characteristics useful for separation of the molecules of interest. For example, moieties capable of specific interactions with a molecule of interest may be designed into peptides that are used to make a hydrogel. Suitable moieties capable of specific interaction include, but are not limited to, epitopes, ligands, specific small molecules, nucleic acid sequences, and the like. Hydrogels of this type may be used in either a positive selection (i.e., binding the molecule of interest) or negative selection (i.e., binding contaminants) mode. For use in embodiments of this type, it may be desirable to control the nanoporous and miroporous morphology of the hydrogels in order to purify the desired molecule. For example, the size of the pores in the hydrogels of the invention may be controlled by varying the amount by weight of peptide used, gelation conditions, and/or the peptide structure to optimize purification of a molecule of interest.

The hydrogels of the invention may be used to improve the tolerance and/or adhesion of materials placed in a living organism. For example, material to be implanted in a living organism (e.g., prosthetics, pace makers, supports, etc) may be first coated with a hydrogel of the invention. Such hydrogels may be made of peptides having one or more moieties that promote the adhesion of the tissues of the organism to the implanted device. Such moieties may include adhesion epitopes and the like. Hydrogels may also include immune modulating (e.g., suppressing or stimulating) moieties such as small molecules or epitopes.

In another embodiment, hydrogels of the invention may be used for harmful metal ion remediation from aqueous solutions. Peptides may be designed that contain functionalities that bind to the harmful metal ion. The peptides may be introduced into a solution comprising the harmful metal ion and then the gelation of the peptides may be induced. The harmful metals may be trapped inside the hydrogel and the hydrogel may be separated from the rest of the solution by any suitable technique, for example, by filtration. Optionally, the hydrogel may be dissolved and the harmful metal ion may be isolated.

In some aspects, the present invention provides a method of making a hydrogel. Such a method may entail providing a solution comprising peptides and altering one or more characteristics of the solution, wherein a hydrogel is formed. The characteristic altered may be any characteristic that results in formation of a hydrogel upon its alteration. Suitable examples include, but are not limited to, ionic strength, temperature, concentration of a specific ion, and pH. In some embodiments, altering one or more characteristic of the solution may comprise contacting the solution with electromagnetic radiation. In particular embodiments, the character altered may be the pH of the solution. In some embodiments, altering one or more characteristic of the solution results in a salt concentration of from about 20 mM to about 400 mM. Any salt may be used, for example, KCl, NaCl, MgCl$_2$, KF, MgSO$_4$, etc. In one embodiment, the salt may be NaCl. In some embodiments, the solution may have a desired pH, for example, a pH of less than 9, a pH of from about 6.0 to about 8.5, a pH of from about 7.0 to about 8.0, or a pH of about 7.4, which may stay the same or be changed upon formation of the hydrogel.

In some aspects, the present invention provides a hydrogel. Such hydrogels may comprise peptides and from about 20 mM to about 400 mM salt. As discussed above, any salt may be used, for example, NaCl. Any peptide capable of forming a hydrogel may be used, for example, MAX1.

In one aspect, the present invention provides a method of making a hydrogel. Such a method may comprise injecting a solution comprising peptides into an animal, wherein the solution forms a hydrogel inside the animal. Any animal may be used, for example, mammals including humans. A solution for use in this aspect of the invention may comprise any number of components. In some embodiments, the solution may comprise one or more therapeutic agents. Any therapeutic agent known to those skilled in the art may be used. In particular embodiments, the solutions may comprise one or more therapeutic agent selected from a group consisting of small molecules, peptides, proteins, and cells.

In another aspect of the invention, the invention provides a method of delivering a therapeutic agent to an animal in need thereof. Such a method may comprise administering a solution comprising the therapeutic agent and one or more peptides to the animal, wherein the solution forms a hydrogel inside the animal. Such a method may be practiced on any type of animal including mammals such as humans. Any type of therapeutic agent known to those skilled in the art may be used, for example, small molecules, peptides, proteins, and cells. One of ordinary skill in the art will appreciate that a therapeutic agent is any agent that results in the prevention and/or amelioration of any undesirable condition.

In another aspect, the present invention provides a method of delivering a therapeutic agent to an animal in need thereof, comprising administering a hydrogel comprising the therapeutic agent and one or more peptides to the animal. Such a method may be practiced on any type of animal including mammals such as humans. Any type of therapeutic agent known to those skilled in the art may be used, for example, small molecules, peptides, proteins, and cells.

In another aspect, the present invention provides a method of treating a wound in an animal. Such a method may comprise contacting the wound with a solution comprising a peptide, wherein the solution forms a hydrogel. Solutions for use in this aspect of the invention may further comprise one or more therapeutic agents. Methods of this type may be practiced on any type of animal, for example, mammals including humans. Any type of therapeutic agent known to those skilled in the art may be used, for example, small molecules, peptides, proteins, and cells.

In another aspect, the present invention provides a method of growing cells. Such methods may comprise forming a hydrogel comprising cells and maintaining the cells under conditions suitable for cell viability. Hydrogels for use in this aspect of the invention typically comprise peptides. Hydrogels may be formed, for example, by adjusting one or more characteristic of a solution comprising peptides. The characteristic adjusted may be one or more of pH, ionic strength, and specific ion concentration. In one particular embodiment, the characteristic adjusted is ionic strength. In another particular embodiments, the characteristic adjusted is Ca$^{2+}$ ion concentration. Any type of cell may be grown using methods of the invention, for example, animal cells such as mammalian cells including human cells. In some particular embodiments, the cells may be osteoblasts or fibroblasts. Cells to be grown using methods of the invention may be recombinant cells, i.e., may contain one or more exogenous nucleic acid molecules. Such nucleic acid molecules may be incorporated into the genome of the cell and/or may be maintained extra-chromosomally. Cells to be grown using methods of the invention may express a protein of interest. Examples of proteins of interest include, but are not limited to, antibodies.

In another aspect, the present invention provides a sensor comprising a hydrogel. Hydrogels for use in sensors of the invention may have one or more characteristic that is altered when the hydrogel is contacted with an analyte of interest. An analyte of interest is any material desired to be detected. In some embodiments, the characteristic of the hydrogel altered in response to the analyte is stiffness. In other embodiments, the characteristic altered is an optical property. Optical properties include, but are not limited to, absorbance, ellipticity, light scattering characteristics and the like.

In another aspect, the present invention provides a method of detecting environmental conditions. Such methods may entail contacting a sensor comprising a hydrogel with a sample representative of the environmental conditions and determining one or more characteristic of the hydrogel. Typically, in methods of this type, one or more characteristic of the hydrogel is altered when the hydrogel is contacted with an analyte of interest. Any characteristic of the hydrogel may be altered, for example, stiffness and/or an optical property. Methods of this type may also include comparing the characteristic of the hydrogel to the same characteristic of the hydrogel determined at a different time.

In another aspect, the present invention provides methods of purifying a molecule of interest. Such methods may include contacting a solution comprising the molecule of interest and one or more contaminants with a hydrogel under conditions causing the molecule of interest to be retained by the hydrogel and recovering the molecule of interest from the hydrogel. Typically, in methods of this type, at least one contaminant is not retained by the hydrogel or is retained to a lesser degree than the molecule of interest. Molecules of interest may be any molecule known to one of ordinary skill in the art. Examples of molecules of interest include proteins, nucleic acid molecules, small molecules and the like. In one particular embodiment, the molecule of interest may be an antibody. A molecule of interest may be a therapeutic agent or a component part of a therapeutic agent. A component part of a therapeutic agent is a material that may be modified to become a therapeutic agent. One example of a component part of a therapeutic agent is an antibody that may be covalently modified with a cytotoxic compound to become a therapeutic agent.

In another aspect, the present invention provides a method of purifying a molecule of interest including contacting a solution comprising the molecule of interest and one or more contaminants with a hydrogel under conditions causing at least one contaminant to be retained by the hydrogel and recovering the molecule of interest. Typically, in methods of this type, at least one contaminant is retained by the hydrogel or is retained to a greater degree than the molecule of interest. Molecules of interest may be any molecule known to one of ordinary skill in the art. Examples of molecules of interest include proteins, nucleic acid molecules, small molecules and the like. In one particular embodiment, the molecule of interest may be an antibody. A molecule of interest may be a therapeutic agent or a component part of a therapeutic agent. A component part of a therapeutic agent is a material that may be modified to become a therapeutic agent. One example of a component part of a therapeutic agent is an antibody that may be covalently modified with a cytotoxic compound to become a therapeutic agent.

BRIEF DESCRIPTION OF THE DRAWINGS

FIG. 2 shows a schematic representation of some of the factors that can be varied in peptides used in preparing hydrogels having desired characteristics according to the present invention. The specific molecular factors that can be changed include:

FIG. 4 shows experimental results obtained from a hydrogel prepared according to the invention.

FIG. 6 shows rheology data on 2 wt % MAX1 hydrogel at pH 9.

FIG. 7 shows results obtained with laser scanning confocal microscopy (LSCM) and cryo transmission electron microscopy (cryoTEM). FIG. 7A shows LSCM of hydrogel microstructure. Green regions are fluorescently stained self-assembled peptide and black regions are water filled pores and channels. Space bar is=20 μm. FIG. 7B shows cryoTEM of self-assembled nanostructure. Dark structures are self-assembled peptide scaffold while lighter gray areas are composed of vitrified water. Space bar is equal to 200 nm.

FIG. 10A shows reversible temperature dependent CD of a 150 μM solution of MAX3 (125 mM Borate, 10 mM NaCl, pH 9). ○ is MAX3 at 5° C. showing completely unfolded character. □ is MAX3 after heating to 80° C. and undergoing intramolecular folding. ◆ is MAX3 after cooling back to 5° C. showing completely unfolded character. ▲ is MAX3 after reheating to 80° C. and undergoing intramolecular folding. FIG. 10B shows temperature dependency of the storage modulus (G') for a 2 wt % aqueous preparation of MAX3 under identical conditions; data was collected at the indicated temperatures for 20 min. time intervals allotting time for approximate instrumental/sample equilibrium between intervals. The rheology clearly shows reversible self-assembly and consequent solid hydrogel rigidity with temperature.

FIG. 11 shows the structure of various peptides that may be used in the practice of the instant invention. FIG. 11A shows the structure of MAX1, in which valines incorporated at H-bonding positions within each hairpin project their side chains outward making intermolecular lateral hydrophobic contacts (as described in FIG. 2) possible which help drive self-assembly. FIG. 11B shows the structure of MAX4, in which valines are now incorporated at non H-bonding positions and project their side chains inward; valine-derived intermolecular interactions are less likely and self-assembly is not as favorable.

FIG. 14A shows the salt dependent CD of 150 μM MAX1 at pH 7 (20 mM Tris). At 20 mM KF salt the CD indicates a completely unfolded conformation ●. At 150 mM KF the CD indicates strong beta-sheet conformation formation ■. FIG. 14B shows frequency sweep data for MAX1 hydrogel formed at pH 7 with serum free growth media. The frequency independence of the moduli (G'=●, G"=■) clearly indicate a heavily crosslinked, rigid hydrogel material.

FIG. 16 shows light microscopy results. FIG. 16A shows $10^4$ fibroblasts in DMEM with 10% calf serum plated on 2 wt % Max1 gel, t=4.5 hours. FIG. 16B shows the results from 16A at t=72 h. FIG. 16C shows the control, $10^4$ fibroblasts in DMEM with 10% calf serum plated on polystyrene, t=4 h. FIG. 16D shows the control at t=72 h. FIG. 16E shows $10^4$ fibroblasts in DMEM without serum plated on 2 wt % Max1 gel, t=4.5 hours. FIG. 16F shows the same material as FIG. 16E with calf serum added to the sample at 4 h and incubated for 72 h.

FIG. 19 shows a schematic representation of a peptide for use in the invention indicating locations in the peptide that may be modified. Cell binding epitopes, such as the sequence arginine, glycine, aspartic acid (RGD) can be incorporated at 1) one or both of the peptide ends, 2) in the middle of one or both of the peptide strands, 3) at one or both of the turn flanking positions, or 4) any lysine side chain via covalent attachment.

FIG. 23 shows negatively stained (Uranyl acetate) TEM images of self-assembled structure of hydrogels.

FIG. 26 shows rheology data (G':●, G":○) of 2 wt % Max1 solution in cell growth media at 37° C. As shown in FIG. 6 relative to a pH folding and assembly trigger, gels produced by peptide exposure to cell growth media form quickly, are significantly rigid, can be shear thinned (e.g. syringe injected), and can quickly reheal to their original stiffness after cessation of shear.

DETAILED DESCRIPTION OF THE INVENTION

Figure 1:
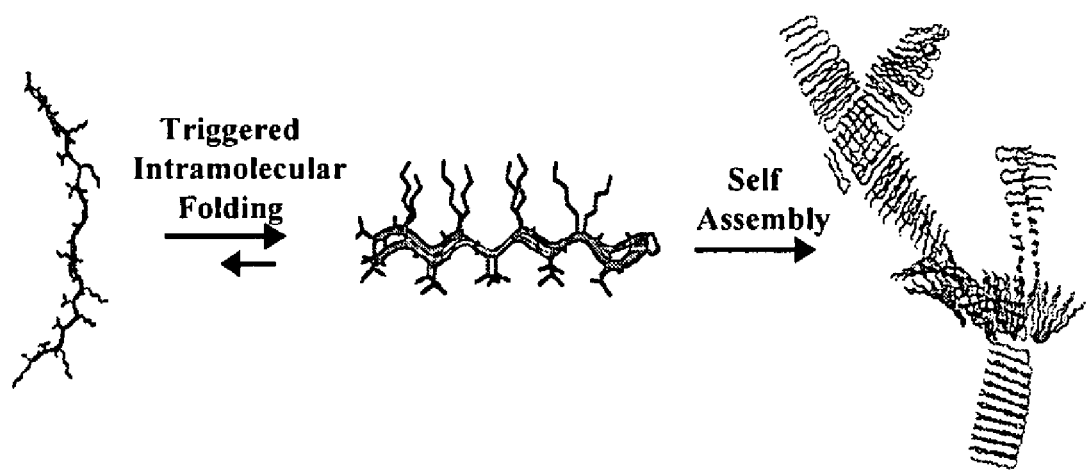
FIG. 1 shows a schematic representation of the self-assembly of peptides to form a hydrogel according to the present invention. Unfolded peptides are induced to individually fold into a conformation amenable to self-assembly with other like-folded peptides. The folding process is caused by exposure to desired stimuli and the self-assembly process results in an interconnected, fibrillar, hydrogel network.

In one aspect, the present invention provides a self-assembly hydrogelation strategy that employs small peptides as the gel scaffold building block. Peptides may be designed to undergo self-assembly only after intramolecular folding into a β-hairpin conformation that is capable of intermolecular association. The folding event can be triggered by environmental stimuli affording responsive hydrogelation systems. Using peptides is advantageous due to their quick chemical synthesis and the possibility of incorporating novel residues and functional epitopes for tailored material and biological properties. The self-assembled nature of the hydrogel eliminates the need for exogenous crosslinking agents. The peptide-based hydrogels presented herein are rigid yet easily processed. This hydrogelation strategy will provide a cytocompatible gelation system that may be used for potential in vitro and in vivo tissue engineering construct formation. The present invention establishes the relationship between peptide structure and ultimate hydrogel morphological, rheological, and cell-level biological properties. This has been accomplished by: 1) Gaining a fundamental understanding of the folding and self-assembly process leading to hydrogel formation and how molecular design affects material properties. By rigorously understanding the relationship between designed peptide structure, the folding/self-assembly process, and the ultimate material properties one can produce hydrogels having tailored tissue engineering properties. 2) Enhancing the processibility of hairpin-based hydrogels by designing active intramolecular folding triggers that allow peptide solutions to undergo hydrogelation on cue. By designing peptides that fold in response to biologically compatible cues; for example, pH, salt concentration, cell culturing media, light, body temperature, or specific ion concentration (e.g., $Ca^{2+}$); one of ordinary skill in the art can design hydrogelation processes for both in vitro and in vivo tissue engineering applications. 3) Determining how peptide structure and material properties affect the adhesion and proliferation of model cell lines (e.g., fibroblast and osteoblast cell lines). The peptidic and porous nature of the β-hairpin hydrogels make these materials candidates as cytocompatible (non-cytotoxic, promotes cell adhesion and proliferation), easily functionalized substrates for potential bone and soft tissue engineering applications. Correlations between peptide structure, hydrogel rigidity and cytocompatibility have been established.

The present invention incorporates one or more of the aforementioned material properties within one fundamental molecular design. This alternate strategy employs four fundamental design facets to produce hydrogels: 1) Small de novo designed peptides may be used to prepare hydrogels. 2) Hydrogels may be constructed via a pure self-assembly mechanism that eliminates the need for exogenous crosslinking agents. 3) The peptides may be designed such that they do not undergo self-assembly leading to hydrogel scaffold formation unless they are correctly intramolecularly folded into a targeted conformation. 4) This intramolecular folding event, and thus hydrogelation, can be triggered by specific, environmental stimuli.

FIG. 1 displays one embodiment of the premise of this simple material construction design. Small peptides are designed to be unstructured in aqueous solution until exact solution conditions dictate intramolecular folding into a β-hairpin conformation. This facially amphiphilic hairpin is amenable to self-assembly leading to a rigid, porous, β-sheet rich hydrogel. We propose a nanostructure for the self-assembled state (at right in FIG. 1) consistent with short segments of fibril interspersed with hydrophobically associated interfibril junctions (See FIG. 7B). It should be noted that this morphology is very different than that observed from self-associating peptides that afford classical fibril-based assemblies. In classical systems, peptides associate into laminated, β-sheet-rich fibrils. The self-assembly process is normally very slow (hours to months) and irreversible affording fibrils that can have micron length dimensions. Examples exist of hydrogels formed upon entanglement of well-developed, ripened fibrils. In contrast, our proposed peptide system provides a new mechanism in which triggered intramolecular folding must occur prior to desired intermolecular self-assembly. Thus, hydrogelation can be initiated by a diverse array of environmental triggers. The hydrogelation event is very rapid (occurring in seconds depending on conditions) and, if desired, can be designed to be completely reversible. Resultant gels are characterized by nano- to microporous morphology and significant material rigidity despite being composed of >98% water.

The feasibility of using small peptides to form complex materials is well demonstrated in the literature. Peptides have been observed to self-assemble into helical ribbons, nanotubes and vesicles, surface-assembled structures and others. The preparation of materials from small peptides is advantageous because they can be chemically synthesized rapidly and novel amino acid residues can be incorporated. In addition, the use of orthogonal protection strategies allows for regioselective ligation of chemical moieties to amino acid side chains affording conjugates with tailored functions (e.g. cell adhesion). In terms of regioselectivity, the ability to completely and precisely functionalize the monomeric building block of a self-assembling system is highly desirable when compared to the relatively nonselective methods used to chemically modify an existing polymer. In one aspect of the invention, peptides can be designed to fold in response to their environment; taking advantage of this property can lead to smart materials that form (or dissolve) on cue. Examples of peptides that may be used in the practice of one or more aspects of the invention include, but are not limited to, the following:

| | |
|---|---|
| MAX1 | VKVKVKVK $V^D$PPT KVKVKVKV-NH$_2$ |
| MAX2 | VKVKVKVK $V^D$PPT KVKTKVKV-NH$_2$ |
| MAX3 | VKVKVKTK $V^D$PPT KVKTKVKV-NH$_2$ |
| MAX4 | KVKVKVKV $K^D$PPS VKVKVKVK-NH$_2$ |
| MAX5 | VKVKVKVK $V^D$PPT KVKEKVKV-NH$_2$ |
| MAX6 | VKVKVKVK $V^D$PPT KVKCKVKV-NH$_2$ |
| MAX7 | VKVKVKVK $V^D$PGT KVKVKVKV-NH$_2$ |
| MAX8 | VKVKVKVK VP$^D$PT KVKVKVKV-NH$_2$ |

(SEQ ID NO: 1)

| | |
|---|---|
| MAX9 | VKVKVKVK VPPT KVKVKVKV-NH$_2$ |
| MAX10 | VKVKVKVK $V^D$P$^D$PT KVKVKVKV-NH$_2$ |
| MAX11 | VKVKKCK $V^D$PPT KVKCKVKV-NH$_2$ |
| MAX12 | VKVKCKVK $V^D$PPT KVCVKVKV-NH$_2$ |
| MAX13 | ISINYRTE I$^D$PPT SINYRTEI-NH$_2$ |
| MAX14 | VKVKVCVK $V^D$PPT CVKVKVKV-NH$_2$ |
| MAX15 | VKVKVCVK $V^D$PPT KVKVCVKV-NH$_2$ |
| MAX16 | VKVKVKVC $V^D$PPT KVKVCVKV-NH$_2$ |
| MAX17 | RGDVKVKVKVK $V^D$PPT KVKVKVKVRGD-NH$_2$ |
| MAX18 | VKVEVKVE $V^D$PPT KVEVKVEV-NH$_2$ |
| MAX19 | VKVKVKVKVK $V^D$PPT KVKVKVKVKV-NH$_2$ |

(SEQ ID NO: 2)

| | |
|---|---|
| MAX20 | VKVKVKVK YNGT KVKVKVKV-NH$_2$ |
| MAX21 | VKVKVK $V^D$PPT KVKVKV-NH$_2$ |

(SEQ ID NO: 3)

-continued

```
MAX22   VKVKVKVK GGGG KVKVKVKV-NH2

MAX23   VEVEVEVE VDPPT EVEVEVEV-NH2

MAX24   VXVXVXVX VDPPT XVXVXVXV-NH2
        X = Ornithine

MAX25   VXVXVXVX VDPPT XVXVXVXV-NH2
        X = Diaminobutyric acid

MAX26   VXVXVXVX VDPPT XVXVXVXV-NH2
        X = Diaminopropionic acid

MAX27   VYXYXYX YDPPT XYXYXYXY-NH2
        X = Valine

MAX28   VRVRVRVR VDPPT RVRVRVRV-NH2

(SEQ ID NO: 4)
MAX29   VKVKVKVKVRGDKVKVKVKV-NH2

MAX30   XKXKXKXK VDPPT KXKXKXKX-NH2
        X = Aminoisobutyric acid

MAX31   XKXKXKXK VDPPT KXKXKXKX-NH2
        X = Norvaline

MAX32   XKXKXKXK VDPPT KXKXKXKX-NH2
        X = Norleucine

MAX33   FKFKFKFK VDPPT KFKFKFKF-NH2

MAX34   IKIKIKIK VDPPT KIKIKIKI-NH2

MAX35   HWSFTIKIT_VDPPT_HWSFTIKIT-NH2
```

In addition to the amino acids specifically recited above, at any position of any of the above peptides indicated with X, each X can independently be any natural or non-natural amino acid (L or D stereochemistry) or any analog of an amino acid known to those skilled in the art. In this application, D stereochemistry will be indicated by a superscript before the D amino acid, thus $^{D}P$ is D-proline.

In some embodiments of the invention, peptides may fit the general formula VKVKVKVK(XXXX)$_a$KVKVKV (XXXX)$_b$KVKVKVKV-NH$_2$ (SEQ ID NO:5). Specific examples of this embodiment of the invention include, but are not limited to,

```
MAX36   (XXXX)a= VDPPT     (XXXX)b= KDPPK

MAX37   (XXXX)a= VDPGT     (XXXX)b= KDPGK

MAX38   (XXXX)a= VDPGT     (XXXX)b= KDPPK

MAX39   (XXXX)a= VDPAT     (XXXX)b= KDPAK

MAX40   (XXXX)a= VDPPT     (XXXX)b= KDPGK (SEQ ID NO:6)
MAX41   (XXXX)a= VDPPT     (XXXX)b = KNGK (SEQ ID NO:7)
MAX42   (XXXX)a= VNGT      (XXXX)b= KDPPK

MAX43   (XXXX)a= VNGT      (XXXX)b= KNGK

MAX44   (XXXX)a= VDPAT     (XXXX)b= KDPDAK
```

In addition to the amino acids specifically recited above, at any position of any of the above peptides indicated with X, each X can independently be any natural or non-natural amino acid (L or D stereochemistry) or any analog of an amino acid known to those skilled in the art. Preferably, each (XXXX)$_a$ and (XXXX)$_b$ may comprise a sequence capable of forming a turn (e.g., a β-turn).

In some embodiments of the invention, peptides may fit the following general formulas:

MAXX$_1$  (VK)$_m$V$^D$PPT (KV)$_n$-NH$_2$
m = 1-100, n = 1-100

MAXX$_2$  (VK)$_m$VPPT (KV)$_n$-NH$_2$ (SEQ ID NO:8)
m = 1-100, n = 1-100

MAXX$_3$  (VK)$_m$V$^D$P$^D$PT (KV)$_n$-NH$_2$
m = 1-100, n = 1-100

MAXX$_4$  (VK)$_m$GGGG (KV)$_n$-NH$_2$ (SEQ ID NO:9)
m = 1-100, n = 1-100

MAXX$_5$  (VK)$_m$VP$^D$DPT (KV)$_n$-NH$_2$
m = 1-100, n = 1-100

MAXX$_6$  (VK)$_m$YNGT (KV)$_n$-NH$_2$ (SEQ ID NO:10)
m = 1-100, n = 1-100

MAXX$_7$  (VK)$_m$VRGD (KV)$_n$-NH$_2$ (SEQ ID NO:11)
m = 1-100, n = 1-100

Each m and n may independently be from 1-100 and m may or may not equal n.

Among the advantages of the invention are the ease of hydrogel preparation and the favorable resultant material properties, particularly processibility and morphology. The use of a self-assembly strategy eliminates the need for chemical crosslinks. Using chemicals to induce crosslinks is generally non-selective and many crosslinking reagents are toxic and not easily purified away from the hydrogel scaffold.

In terms of processibility, hydrogels constructed from physically crosslinked, self-assembled networks can be responsive to mechanical shear. This characteristic provides a free flowing suspension during the application of shear and complete reformation of the gel network (self healing) after cessation of the shear (see Prudhomme, et al., *Langmuir* 1996, 12, 4651-4659, and Nowak, et al., *Nature* 2002, 417, 424-428). This combination of shear thinning and self-healing allows material formation in a spatially resolved manner. For example, in some embodiments of the invention, one of ordinary skill in the art could inject (shear thin) a hydrogel pre-formed ex vivo in the presence of desired biological constituents (growth media, growth factors, living cells, etc. . . . ) into a host where it self heals providing a scaffold for tissue regeneration. In addition, hydrogels formed via self-assembly are not limited to ex-vivo preparations as described above. The present invention provides peptide systems that undergo self-assembly when exposed to biologically relevant stimuli such as salt, temperature and pH (see Pochan, et al., *Journal of the American Chemical Society* 2003, 125, 11802-11803 and Schneider, et al., *Journal of the American Chemical Society* 2002, 124, 15030-15037). This could allow for the formation of hydrogel directly in vivo via the injection of a peptide solution. Hydrogel systems in which both ex and in vivo preparations are possible are most versatile in terms of processibility and are within the scope of the present invention.

The self-assembly of β-hairpins described herein may provide rigid networks composed of minimal solid material (shear moduli, G', >1000 Pa with ≦2 wt % peptide) providing for a significantly dilute, porous scaffold with no need for additional processing. These gels are porous on both the nanoscale and microscale. This porous character may aid cell migration within the hydrogel scaffold and allow the diffusion of nutrients. In one embodiment, the present invention provides correctly designed peptides that can undergo rapid, triggered hydrogelation affording rigid, porous materials that are cytocompatible. Self-assembly can be triggered by physiologically relevant stimuli resulting in hydrogels that shear thin, making processing of this system versatile.

The proposed hydrogelation system relies on the ability of a peptide to adopt a folded conformation that is amenable to self-assembly (i.e., if the peptide isn't correctly folded, it doesn't self-assemble into hydrogel). In addition, it is possible to design peptides that only fold in response to an environmental cue. The result is a peptide system that will undergo hydrogelation only in the presence of a desired stimulus. This environmental dependence provides for a hydrogel that is inherently "smart" in that the system will not gel until the individual peptides are folded. Depending on the nature of the stimulus (trigger), hydrogelation via this process can be designed to be totally reversible; simply removing the stimulus unfolds the peptides that comprise the scaffold resulting in hydrogel dissolution. Several examples of environmental triggers include temperature, pH, ionic strength, specific ion binding (e.g., $Ca^{2+}$), and electromagnetic radiation (e.g., light).

In some aspects, the present invention provides a method of producing a hydrogel that may comprise (a) triggering intramolecular peptide folding into β-hairpin conformation, and (b) self-assembling of hairpins into hydrogels. The peptides may be designed so as to provide a hydrogel having the desired material properties (e.g., porosity, rigidity/modulus, biofunctionality, etc, see FIG. 1).

All of the desired aspects of the hydrogels of the invention may be controlled by peptide design. Peptides for use in the present invention may be small peptides (e.g., from about 10 to about 200 residues, from about 10 to about 100 residues, from about 10 to about 75 residues, from about 10 to about 50 residues, from about 10 to about 40 residues, from about 10 to about 30 residues, from about 10 to about 25 residues, from about 10 to about 20 residues, from about 15 to about 200 residues, from about 15 to about 100 residues, from about 15 to about 75 residues, from about 15 to about 50 residues, from about 15 to about 40 residues, from about 15 to about 30 residues, from about 15 to about 25 residues, from about 15 to about 20 residues, from about 20 to about 200 residues, from about 20 to about 100 residues, from about 20 to about 75 residues, from about 20 to about 50 residues, from about 20 to about 40 residues, from about 20 to about 30 residues, or from about 20 to about 25 residues). Peptides of the invention may incorporate one or more modified amino acid residues (e.g., D-amino acids, homologs of naturally occurring amino acids, amino acids with modified side chains, etc). Peptides of the invention preferably adopt a secondary structure (e.g., β-hairpin secondary structure) in response to one or more triggers. Triggers may be one or more changes in environmental conditions. While specific peptides will be described later in detail, in one aspect peptides of the invention may be composed of high β-sheet propensity residues flanking an intermittent four residue turn sequence. Polar and apolar residues may be arranged sequentially in the strand regions to afford amphiphilic surfaces in the folded state.

In some embodiments of the invention, the ability of peptides to self-assemble is dependent upon their unimolecular folded state. For example, under folding conditions peptides may adopt a desired secondary structure (e.g., may adopt an amphiphilic α-hairpin structure where one face of the hairpin is lined with hydrophobic residues and the other face is lined with hydrophilic residues). In this example, intramolecular folding is dictated by the alleviation of charge density on the hydrophilic face upon folding, the formation of intramolecular hydrophobic van der Waals interactions, the formation of intramolecular hydrogen bonds between β-strands within the hairpin, and the turn propensity of the turn sequence, FIG. 2. Intimate knowledge of the factors that govern intramolecular folding allows one to design active triggering mechanisms of the folding event. After intramolecular folding, subsequent self-assembly of monomeric hairpins is facilitated facially by hydrophobic association of the hydrophobic faces of folded hairpins and laterally via H-bond formation and hydrophobic van der Waals contacts between neighboring hairpins. Detailed knowledge of these parameters allows one to control the self-assembly process and thus the ultimate material properties. All of these design parameters are outlined below and shown schematically in FIG. 2. One of ordinary skill in the art can appreciate that peptides may be designed so as to adopt other desired secondary structures that result in a configuration of peptide residues favoring intermolecular association of the peptides and gel formation.

Peptides for use in the hydrogels of the invention can be constructed to have any desired characteristics by varying one or more of the following parameters: 1) electrostatics, for example, by varying the charge within the peptide intramolecular folding rate can be varied; 2) Van der Waals interactions, for example, constructing peptides having varying a) lateral and facial intermolecular hydrophobic interactions and/or b) intramolecular hydrophobic interactions, allows varying the folding and self-assembly of the peptides as well as the material properties of the hydrogel; 3) hydrogen bonding, for example peptides may be constructed with varying a) intramolecular and/or b) intermolecular hydrogen bond formation to vary the folding, self-assembly and final material properties; and 4) turn sequence, for example, the turn region of peptides of the invention may be designed to control folding and thus trigger self-assembly.

The present invention permits one of ordinary skill in the art to design peptides with desired characteristics (i.e., the appropriate electrostatics, intra- and intermolecular hydrophobic van der Waals interactions, and turn sequence) so as to have the desired intramolecular folding, intermolecular self-assembly and material properties. In some embodiments, electrostatics and/or hydrophobic Van der Waals interactions can be used to design peptides having active intramolecular folding triggers. Triggers may be a change in one or more characteristic of a solution comprising the peptides, for example, pH, salt concentration, specific ion concentration, electromagnetic radiation and/or temperature.

In some embodiments, peptides designed as described herein may be used to produce hydrogels that may be used as non-cytotoxic scaffolds that support cell adhesion (for example, mammalian cell adhesion) and proliferation.

Figure 3:
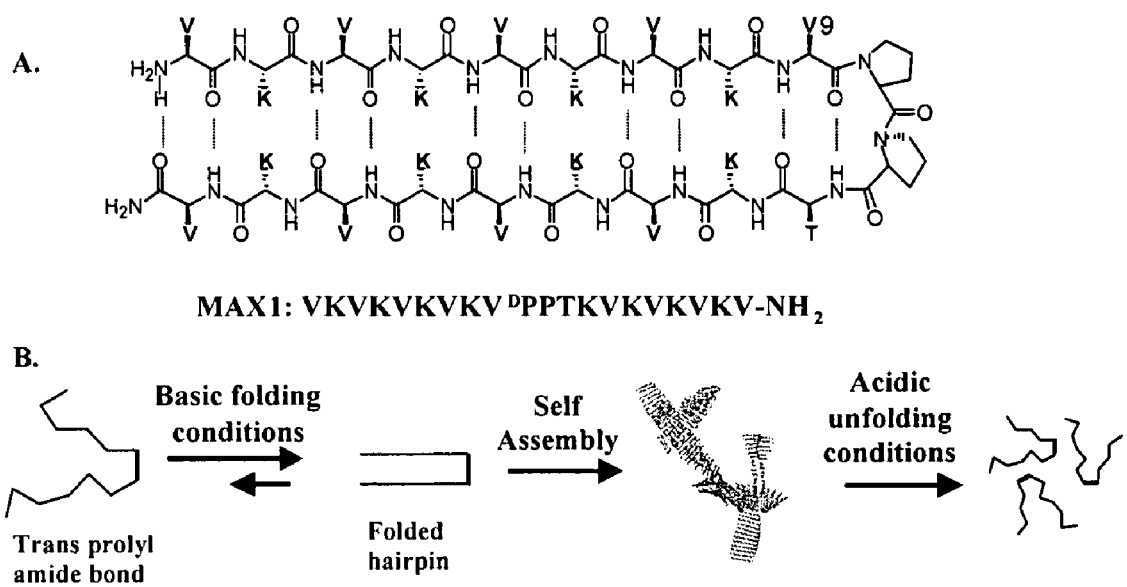
FIG. 3A shows the structure of a peptide for use in the present invention.
FIG. 3B shows a schematic representation of the reversible formation of a hydrogel according to the invention. Specifically, the peptide MAX1 is unstructured unfolded under acidic or neutral pH solution conditions. When exposed to basic solution conditions the trans prolyl amide bond in the MAX1 turn sequence forces the arms of individual peptides into a parallel conformation stabilized by the interactions listed in FIG. 2A. Self-assembly consequently occurs due to interactions described in FIG. 3B. If the resultant hydrogel is exposed to acidic pH conditions the peptides unfold and disassemble back into a dilute, low viscosity aqueous solution.

In one particular embodiment, MAX1, a 20-residue peptide, was designed to probe the effects of electrostatics on peptide intramolecular folding, self-assembly and consequent hydrogel material properties. The sequence is composed of high β-sheet propensity valine and lysine residues flanking an intermittent tetrapeptide -V$^D$PPT- designed to adopt type II' turn structure, FIG. 3A. In addition to incorporating local design elements to stabilize hairpin structure, nonlocal effects were also considered by arranging the polar and apolar residues flanking the β-turn in an alternating fashion to favor β-hairpin formation in the self-assembled state. In addition, a β-branched residue was placed at the i-position of the turn (Val-9) to enforce a trans prolyl amide bond geometry at the i+1 position. This design element ensures that under folding conditions, intramolecular folding of monomeric hairpins is favored prior to self-assembly. A cis prolyl bond, which is designed against, could result in the presentation of individual β-strands within each monomer in an extended conformation. Peptides capable of adopting both cis and trans conformers could undergo indiscriminant self-association of extended and correctly folded monomers and may be actively designed against.

The ability of MAX1 to undergo hydrogelation is dependent upon its unimolecular folded state. Under basic aqueous solution conditions (pH 9.0, 125 mM Borate, 10 mM NaCl), where some of the lysine side chains of MAX1 are neutral, this peptide intramolecularly folds into an amphiphilic β-hairpin (folding can also be triggered at pH 7 under physiological conditions). One face of the hairpin is lined with hydrophobic valine residues while the other face is lined with hydrophilic lysine residues, FIGS. 2 and 3A. After intramolecular folding, subsequent self-assembly of hairpins is facilitated (a) laterally via H-bond formation and attractive hydrophobic interactions between distinct hairpins as well as (b) facially by hydrophobic association of the valine-rich faces of the folded peptide resulting in hydrogelation, FIG. 3B. Since the charged state of the lysine residues are controlled by pH, the unimolecular folding is reversible. Lowering the pH below the intrinsic pKa of the lysine side chains results in intra-strand charge repulsion from neighboring lysines and subsequent unfolding of individual hairpins, ultimately dissolving the self-assembled hydrogel structure. This reversible behavior is unique when compared to β-sheet-rich hydrogels prepared from classical fibril-based designs. In these systems, the self-assembly process is irreversible. This suggests that the amphiphilic hairpins undergo a self-assembly mechanism that is different from peptides that irreversibly lead to fibrils. In fact, thorough characterization of our gelation process from the molecular level through the macroscopic material properties is presented below and indicates that by linking the intramolecular folding of MAX1 to its ability to self-assemble, a responsive material can be prepared.

Figure 4A:
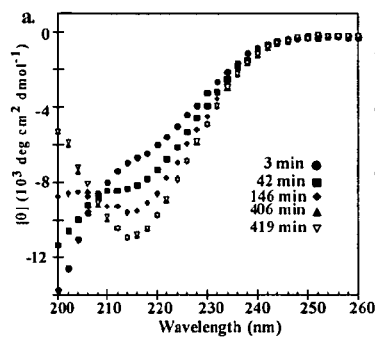
FIG. 4A shows the time-dependent far UV-CD spectra of a 150 μM MAX1 solution (pH 9.0, 125 mM Borate, 10 mM NaCl).

Time-dependent circular dichroism (CD) studies support a hydrogelation mechanism consistent with intramolecular hairpin formation followed by self-assembly. FIG. 4A shows that at micromolar concentrations, when the pH is increased from 5.5 (unfolding conditions) to 9.0 (folding conditions) unstirred solutions of MAX1 undergo a random coil to β-sheet transition taking hours at 20° C. At temperatures>25° C. the folding and self-assembly of MAX1 occurs on the order of seconds. The CD spectrum at 406 minutes displays a clear minimum at 216 nm indicating that MAX1 adopts structure rich in β-sheet.[54] FIG. 4B demonstrates that the observed $\theta_{216}$ is concentration-dependent (comparing $\theta_{216}$ at any one time point for both concentrations), indicating that MAX1 is self-associating and that the rate of assembly increases as the concentration increases. This behavior is consistent across all spectro- and microscopic methods used to interrogate MAX1. For example, at micromolar concentrations used for the CD studies shown in FIGS. 4A and 4B, self-assembly takes hours at 20° C. At millimolar concentrations, such as those used in the rheological studies described below, self-assembly leading to hydrogel takes minutes at 20° C. Interestingly, the rate of self-assembly is not only concentration dependent but also depends on the rate of mixing; vigorously stirred samples adopt sheet structure within seconds at 20° C.

Figure 4B:
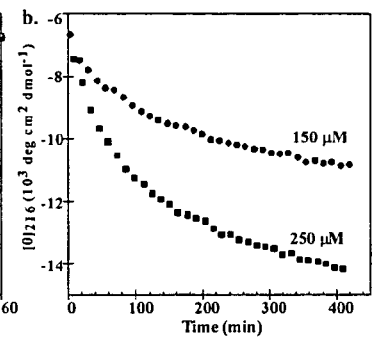
FIG. 4B shows $[\theta]_{216}$ monitored as a function of time for 150 and 250 μM MAX1 solutions under identical conditions.
Figure 4C:
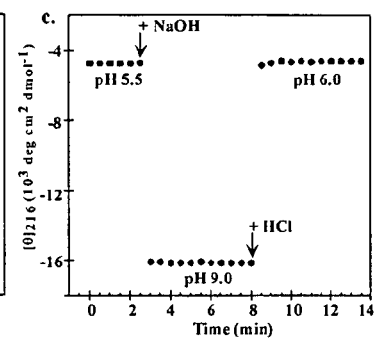
FIG. 4C shows $[\theta]_{216}$ monitored as a function of time and pH for a 300 μM solution of MAX1 showing that the random coil-sheet folding/self-assembly equilibria are reversible. All experiments performed at 20° C.

The reversibility of the folding and self-assembly process was investigated by measuring $\theta_{216}$ as a function of pH and time as shown in FIG. 4C. CD of a stirred solution of MAX1 at pH 5.5 indicates random coil conformation. Adjusting the pH to 9.0 by the addition of NaOH results in β-sheet formation as expected. However, subsequent adjustment of the pH to 6.0 results in complete loss of sheet signal and full recovery of random coil signal. This experiment demonstrates that the assembly process is reversible presumably as a consequence of deprotonating and re-protonating the lysine side chains resulting in unimolecular folding and unfolding, respectively. Again, this reversible behavior is not observed in hydrogels formed from amyloid/prion-like fibrils.

Figure 5:
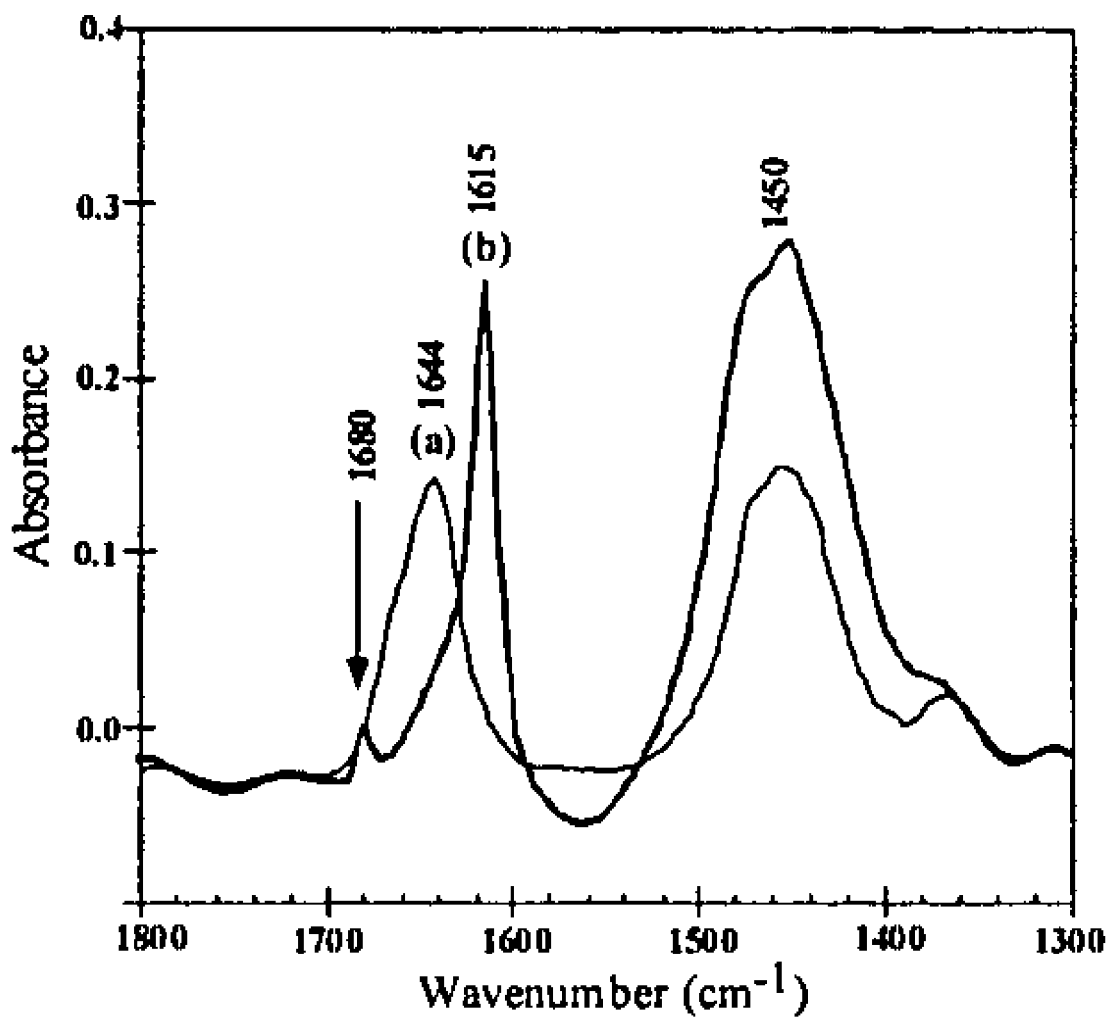
FIG. 5 shows an FTIR; 1 wt % MAX1 at pH 5.5 (trace a) and pH 9.0, after gelation (trace b). The large shift in the amide 1 stretch from 1644 in (a) to 1615 in (b) strongly indicates the growth of beta-sheet structure.

The existence of β-sheet structure within the hydrogel matrix is also supported by FTIR spectroscopy, FIG. 5. 1 wt. % solutions of MAX1 in $D_2O$ at pH 5.5 (where the peptide is soluble) show an Amide I band at 1644 $cm^{-1}$ suggesting that the peptide is unfolded. However, when the pH of this solution is adjusted to 9.0 by the addition of NaOD, gelation occurs and the Amide I band shifts to 1615 $cm^{-1}$, strongly suggesting that MAX1 adopts a structure rich in β-sheet.

Figure 6B:
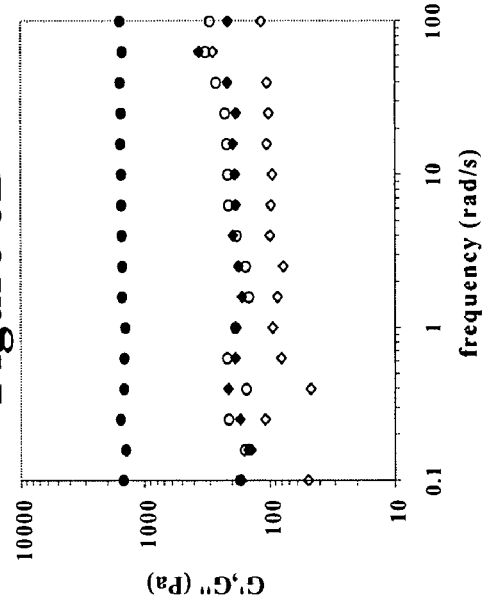
FIG. 6B shows frequency sweep data. The insensitivity of the moduli to frequency indicates a strongly crosslinked, rigid hydrogel due to the peptide folding and self-assembly.
Figure 6A:
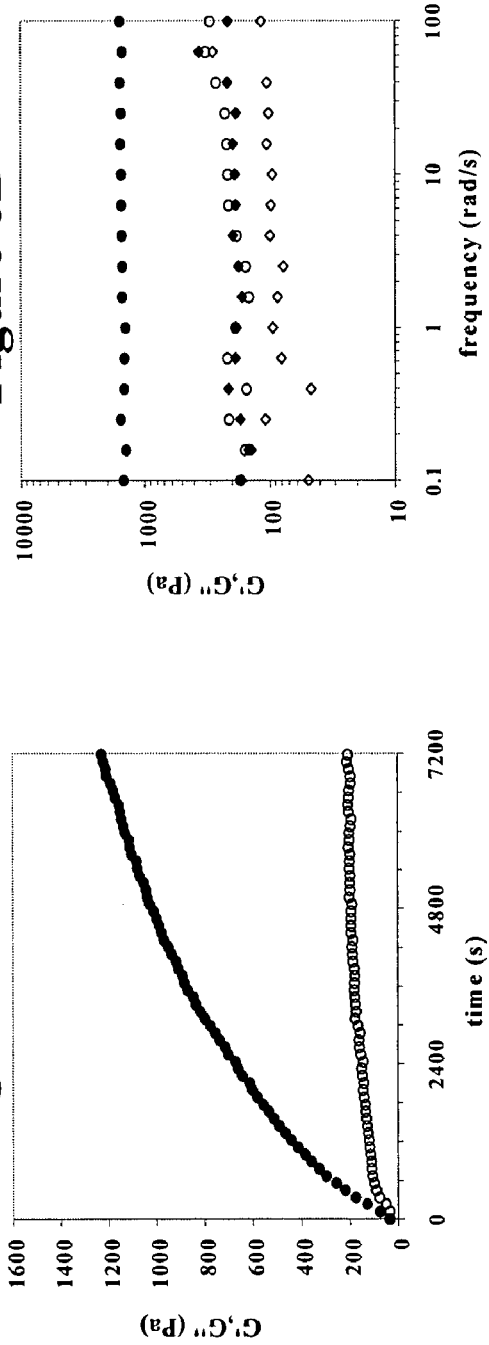
FIG. 6A shows the quick hydrogelation monitored at 6 Hz, 1% strain as a function of time via increase in storage (G', solid symbols) and loss (G", open symbols) shear moduli.

Bulk rheology experiments exhibit the manifestation of unimolecular folding and subsequent self-assembly into a gel network by the onset and growth of elastic properties. FIG. 6A shows the results of a time sweep experiment at constant strain and frequency during which the growth of the storage modulus (sample rigidity) was monitored after hydrogelation was initiated for a 2 wt % solution of MAX1. Similar to the rate of β-sheet formation observed by CD (FIG. 4B), rheology shows that the folding and assembly of MAX1 has significantly progressed after 30 minutes at 20° C. (gel storage modulus of ~600 Pa). Gel formation continued to mature after two hours with a doubling of the gel modulus to ~1200 Pa. An equilibrium storage modulus of ~1600 Pa was reached after several hours of gel formation. This equilibrium behavior is clearly shown by the linear, frequency independent moduli measurements in FIG. 6B. For comparison, the storage modulus of strawberry gelatin is ~50 Pa (data not shown). Rheology indicates that the crossover concentration separating a predominantly liquid-like (G">G') vs. a predominantly gel-like (G'>G") response is about 1 wt %. Several examples of hydrogel moduli from the literature are also shown in FIG. 6B for comparison.

Two hallmarks of a self-assembled gel are to exhibit shear thinning and subsequent recovery of elastic properties after shearing has ended. This drop in viscosity (shear thinning) results from the disruption of physical crosslinks by the application of strain. FIG. 6C clearly shows that MAX1-derived gels shear-thin, the viscosity drops with increasing strain-rate. Importantly, self-assembled gels of MAX1 are capable of quickly reforming after cessation of shear due to the quick relaxation time of the molecular self-assembly process. Herein lies one major advantage of the β-hairpin based hydrogels for potential use in tissue engineering-ease of processibility. Hydrogels can be preformed ex vivo under highly controlled conditions and introduced into a host via syringe injection/shear thinning.

Figure 6D:
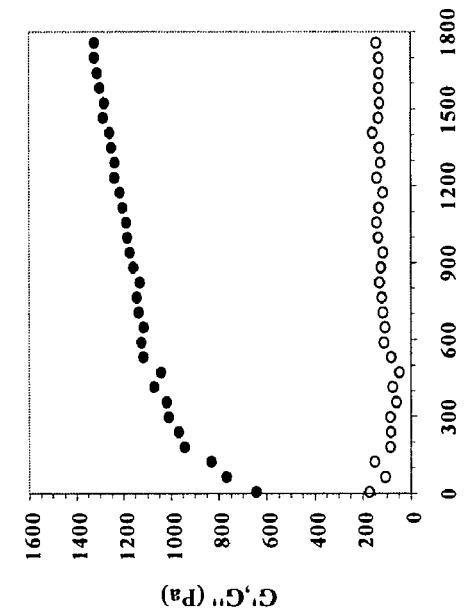
FIG. 6D shows restoration of gel moduli as a function of time after the cessation of strain treatment (1000% strain at 6 Hz for 180 s). Symbols are as defined for FIG. 6A. Immediately after hydrogel destruction via large strain the gel immediately solidifies back to ~75% of its former rigidity and quickly (~10-20 minutes) regains its prestrain rigidity.
Figure 6C:
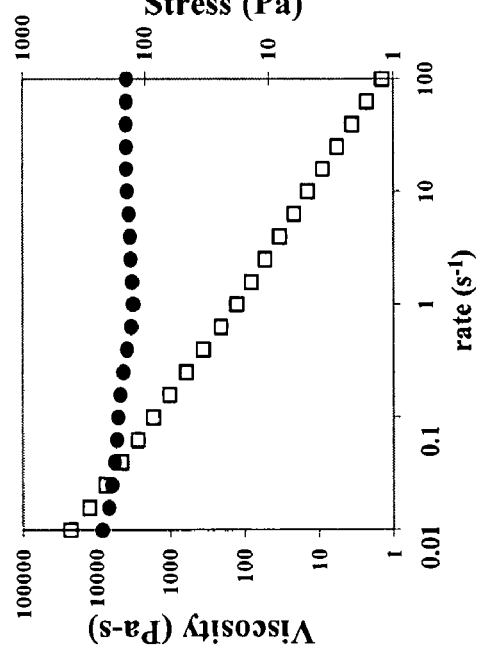
FIG. 6C shows rate sweep data (viscosity, open symbols; stress, closed symbols) indicative of shear thinning material that is easy to post-assembly process (e.g. inject through a syringe).

In FIG. 6D, a time sweep experiment identical to that performed during the original gel formation was run immediately after the application of 1000% strain at 6 Hz for 180 seconds. The initial modulus of the reforming gel was 650 Pa with 80% of the equilibrium modulus recovered after only 30 minutes making this a quick recovering and relatively strong hydrogel. For comparison, a 2 wt % gelatin hydrogel takes over 4 h to recover 80% of its equilibrium modulus after shear thinning.

An interesting comparison can be made between the rheology data and the concentration dependent CD data in FIG. 4B. CD clearly demonstrates that the rate at which MAX1 intramolecularly folds and self-assembles is positively dependent on peptide concentration. The rheologically monitored formation of the 2.0 wt % gel, approximately 6 mM in concentration, can be considered an analogous view of molecular folding and self-assembly at higher peptide concentrations, FIG. 6A. Only after folding can the β-hairpins self-assemble into a gel scaffold and thus provide a viscoelastic response. In fact, a control peptide similar in sequence to MAX1 but designed to disfavor hairpin formation did not undergo hydrogelation when subjected to identical folding conditions (see below).

A rheology experiment demonstrating that the gelation mechanism is reversible with pH changes was attempted by adding a small amount of concentrated HCl to a 2 wt % gel resulting in a final pH~6.0. The rheological response of the system was essentially that of pure water, below the sensitivity threshold of the instrument. This indicated a clear obviation of the self-assembled scaffold and reversibility of gelation. This is in complete agreement with the immediate unfolding of MAX1 under acidic conditions as actively monitored via CD, FIG. 4C. Therefore, CD experiments, which actively monitored the intramolecular folding and intermolecular sheet assembly of MAX1, and rheology experiments, which actively monitored the self-assembly of peptide into a gel scaffold, combine to form a clear image of how material properties can be attributed to molecular folding and consequent assembly mechanisms.

Laser scanning confocal microscopy (LSCM) reveals a heterogeneous gel microstructure in which a continuous gel matrix is permeated by water channels, FIG. 7A. This microscale porosity may be exploited to produce a tissue engineering scaffold. Porous microstructure must be processed into hydrogels prepared from traditional crosslinked hydrophilic polymers. In contrast, the microporosity of hairpin-based gels is a result of the self-assembly process and additional processing is not necessary. The gel matrix regions in FIG. 7A are not solid peptide but rather a dilute peptide network on the nanoscale that is itself permeated by water, FIG. 7B.

Figure 8:
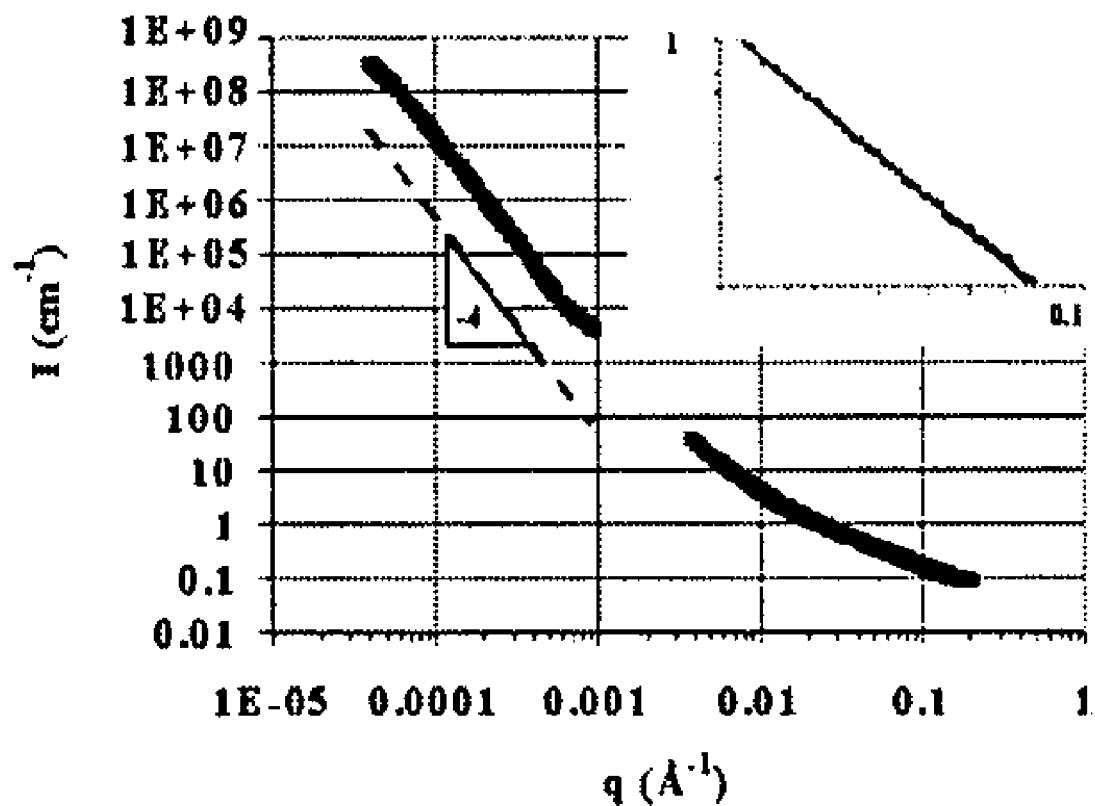
FIG. 8 shows combined USANS/SANS plot of 1 wt % MAX1 hydrogel. (Inset is an enlargement of the log(intensity) from 0.02<q<0.08 with a nonlinear, least-squares fit of −1.1). The −4 slope at low q is indicative of a microporous structure as can be seen microscopically in FIG. 7A. The −1 slope in the inset is indicative of a local rod-like structure as can be seen microscopically in FIG. 7B.

Combined small and ultrasmall neutron scattering (SANS/USANS) data for a 1 wt % gel in $D_2O$ (FIG. 8) is consistent with fibrillar structure of the gel matrix on the nanoscale and the heterogeneous morphology on the microscale. Intensity at low scattering vector, q (where $q=(4\pi/\lambda)\sin(\theta/2)$, $\lambda$=neutron wavelength and $\theta$=scattering angle), clearly exhibits a slope of −4 indicative of scattering from a sharp interface between two phases. In this q regime the two phases are the gel matrix and the 1-10 μm sized water pores and channels as clearly observed in the LSCM in FIG. 7A. In the SANS data at higher q, the most notable feature is the slope of approximately −1 in the Gunier region where the product of q and the radius of gyration, $R_g$, of a particle is <1. This is indicative of scattering from a rod-like object on the nanoscale. This description is consistent with what can be observed in the cryoTEM data (FIG. 7B) where the gel scaffold consists of short regions of fibrillar structure interconnected via junction points.

The results discussed above allow one of ordinary skill in the art to vary the electrostatic characteristics of a peptide and thereby control the formation and/or material properties of hydrogels of the invention. In the specific example described above, self-assembly and material properties demonstrate that peptide folding is partly governed by reducing the lysine charge density of the primary sequence. This allows all of the lysine residues to occupy one face of the folded amphiphilic hairpin. One of ordinary skill in the art will appreciate that amino acid residues other than lysine may be used. For example, any residue that has a charge or can be made to have a charge by varying the environmental conditions may be used. In addition, multiple different amino acid residues may be used in the same peptide.

In some embodiments of the invention, by using changes in solution pH, the intramolecular folding event and subsequent hydrogelation can be triggered and may be reversible. Thus, chemical responsiveness may be realized by linking intramolecular folding to consequent intermolecular assembly. Resultant hydrogels may be mechanically rigid, yet porous on the nano- and microscale, making them very good candidates as cytocompatible materials. In addition, the self-assembled nature of the hydrogel scaffold produces mechanically responsive materials, an attribute that could be exploited to deliver hydrogel/cell constructs via shear thinning methodology.

Figure 2A:
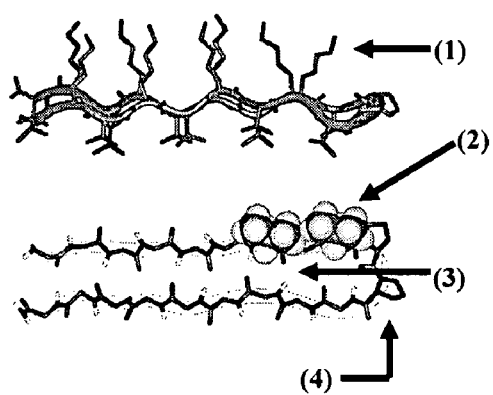
FIG. 2A-*describes* manipulations to influence intramolecular folding and include: 1) electrostatic interactions between the primary amine chemical functionality of the lysine residues of individual peptides, 2) hydrophobic, van der Waals interactions between peptide backbone arms of individual peptides, 3) hydrogen bonding between arms of an individual peptide backbone, 4) turn propensity of individual peptides (i.e. the "stength" of a peptide to fold relative to a particular stimulus).
Figures 9A, 9B:
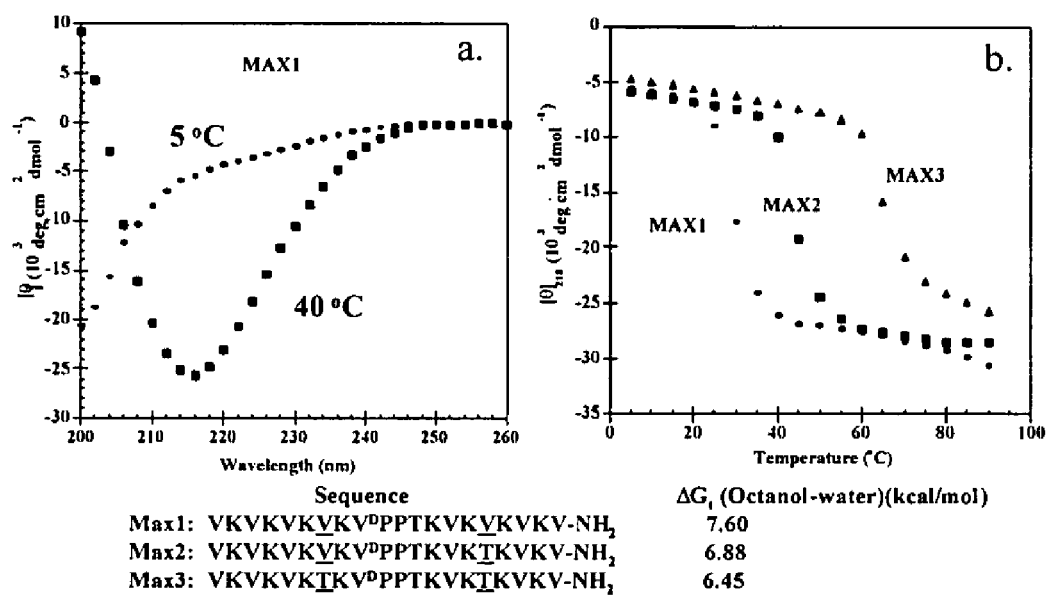
FIG. 9A shows temperature dependent CD of a 150 μM solution of MAX1 (125 mM Borate, 10 mM NaCl, pH 9). At low temperature MAX1 is unfolded (and unassembled). At high temperature MAX1 folds into beta-sheet (and consequently self-assembles into a hydrogel).
FIG. 9B shows temperature dependence of $[\theta]_{218}$ for MAX1, 2 and 3 under identical conditions where MAX1=VKVKVK VKV$^D$PPTKVK<u>V</u>KVKV-NH$_2$, MAX2=VKVKVK <u>V</u>KV$^D$PPTKVK<u>T</u>KVKV-NH$_2$ and MAX3=VKVKVK <u>T</u>KV$^D$PPTKVK<u>T</u>KVKV-NH$_2$. The relative hydrophobicity is MAX1>MAX2>MAX3 due to the isostructural but less hydrophobic substitutions of threonine for valine at the underlined positions. The most hydrophobic folds at the lowest temperature while the least hydrophobic folds at the highest temperature. This is a direct manifestations of the molecular parameter manipulations described in FIG. 2. Also shown are the calculated free energy of transfer of each corresponding unfolded peptide having an overall +8 charge state from octanol into water at 25° C. MAX1, the most hydrophobic has the highest free energy of transfer equal to 7.60 kcal/mol. MAX2 has a calculated transfer free energy of 6.88 kcal/mol, while the least hydrophobic MAX3 has the lowest energy of transfer of 6.45 kcal/mol.

With reference to FIG. 2A, the present invention demonstrates that the formation of intramolecular Van der Waals contacts between residues within a hairpin may stabilize the folded state and that intermolecular lateral and facial contacts between residue side chains of distinct hairpins may stabilize the self-assembled state. This allows the characteristics of the hydrogels of the invention to be varied by adjusting these parameters. This is demonstrated by studying the temperature dependence of hairpin folding and self-assembly of peptides that vary in relative hydrophobicity. It is well known that water is better able to solvate hydrophobic groups at low temperatures. This phenomenon has been used to describe the cold denaturation of proteins where some proteins unfold at low temperatures, exposing their hydrophobic interiors to aqueous solvent. A 150 μM aqueous solution of MAX1 unfolds when cooled below room temperature. The CD spectrum at 5° C. is consistent with random coil conformation, FIG. 9A. However, warming the solution to 40° C. results in a spectra consistent with β-sheet structure. Monitoring the mean residue ellipticity at 218 nm as a function of temperature demonstrates that the temperature at which folding and consequent self-assembly is triggered ($T_{gel}$) is approximately 20° C., FIG. 9B. In fact, previous studies involving the pH induced folding and self-assembly of MAX1 were performed at 20° C. At this temperature, folding and self-assembly are slow enough to be conveniently monitored. At higher temperatures, folding and self-assembly leading to hydrogelation is fast (instantaneous to seconds depending on concentration). If the formation of hydrophobic interactions affects the folding and self-assembly process, then altering the hydrophobic content of MAX1 should affect the temperature at which folding is triggered. FIG. 9B shows CD data for MAX1 and two additional peptides, MAX2 and MAX3. MAX2 is identical to MAX1 except that one valine residue has been replaced with the isostructural, but less hydrophobic residue, threonine. In MAX3, two valines are replaced with threonine residues. The resulting peptides vary in their hydrophobicity as evident by comparing calculated free energies of transfer from octanol into water, FIG. 9. CD data shows that as the hydrophobicity decreases, the temperature at which folding is induced incrementally increases. Thus, the formation of hydrophobic contacts influences folding and self-assembly. This data also shows that in addition to pH, temperature can be used to trigger folding. Thus, the characteristics of the hydrogels of the invention can be varied by adjusting the amino acid residues of the peptides used to form the hydrogels to increase or decrease the hydrophobicity of the amino acid residues used.

Figure 12:
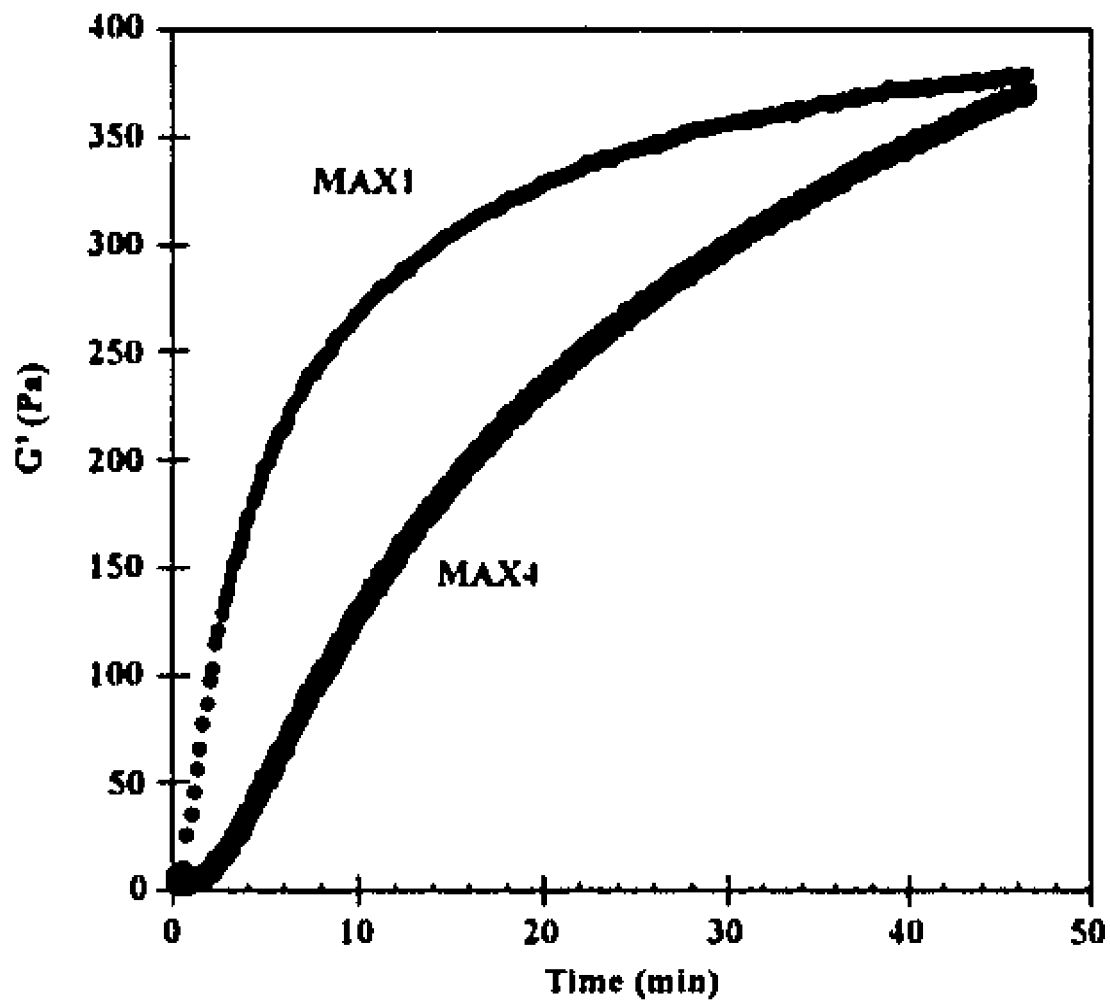
FIG. 12 shows the results of a rheology study. Rate of storage modulus increase for 1 wt % preparations of MAX1 and MAX4 at 40° C. (pH9.0, 125 mM Borate, 10 mM NaCl); frequency=6 rad/sec. MAX1 clearly assembles more quickly than MAX4 due to increased intermolecular, lateral hydrophobic contact.

There are reports of large polymers that are thermally responsive. The present invention provides the first system that employs temperature triggered folding to induce self-assembly. Although thermally induced hydrogelation is not reversible for MAX1 and MAX2, the folding, self-assembly and consequent hydrogelation of MAX3 is thermally reversible. CD spectra of a 150 μM solution of MAX3 demonstrates that this peptide is unfolded at 5° C., FIG. 10A. Heating the solution to 80° C. results in a spectra consistent with β-sheet structure. Subsequent temperature cycles show that folding and unfolding are reversible. In FIG. 10B, rheology demonstrates that a 2 wt % aqueous solution of MAX3 undergoes thermally reversible hydrogelation over several heating/cooling cycles. The temperatures used in both CD and rheology bracket the temperature ($T_{gel}$=60° C., FIG. 9) at which folding and consequent self-assembly is triggered. The CD and rheology data taken together suggest a mechanism of hydrogelation consistent with temperature induced unimolecular folding followed by self-assembly. The temperature responsive behavior exhibited by these peptides expands their versatility due to ease of processing. For example, free flowing peptide solutions could be prepared at room temperature and administered in vivo where the temperature of the body could induce gelation. Some Poly-N-isopropylacrylamide polymers have been engineered have been engineered to undergo such transitions ultimately affording extracellular-like scaffolds for tissue regeneration. The above studies support the idea that the formation of hydrophobic interactions are important. MAX1-3 all contain valines and threonines at hydrogen bonded positions. At these positions, their side chains prefer to adopt a trans rotamer. As a result, hydrophobic residues that oppose each other across the hairpin point their side chains in opposite directions thus making the formation of intramolecular hydrophobic interactions across the strands difficult, FIG. 11A. However, these side chains are nicely positioned to interact laterally with the hydrophobic side chains of neighboring hairpins in the self-assembled state, FIG. 11B. Forming these lateral hydrophobic interactions should favor self-assembly. This was demonstrated using MAX4, a peptide of comparable hydrophobicity to MAX1 that incorporates all of its valine residues at nonhydrogen bonded positions. In MAX4, opposing valine side chains are expected to point towards each other, FIG. 11B. Thus, the valine side chains of MAX4 are less likely than those in MAX1 to form lateral intermolecular hydrophobic interactions. If the formation of lateral intermolecular hydrophobic interactions is of more importance for self-assembly than intramolecular hydrophobic contacts, then the rate of self-assembly should be faster for MAX1 than for MAX4. This difference in rate should be evident in the rate of storage moduli (rigidity) increase. Indeed, FIG. 12 shows that self-assembly leading to a rheological response is faster for 1 wt % preparations of MAX1 as compared to MAX4 at 40° C. ($T_{gel}$=20° C. for both peptides). Therefore, in addition to electrostatics, the formation of lateral hydrophobic contacts during self-assembly also contributes to hydrogelation.

In some embodiments of the invention, various functionalities (e.g., cell adhesion epitopes, receptor agonists, receptor antagonists, ligands, small molecules, etc) may be incorporated into the hairpin hydrogel scaffold. One way to accomplish this would be to functionalize one or more amino acid side chains of the peptide. MAX2 and MAX3, which contain threonine substitutions on the hydrophobic face, are capable of folding and self-assembling at elevated temperatures indicating that neutral residues having similarly sized side chains may be tolerated. In some embodiments, the moieties to be incorporated at a particular side chain may be much larger (e.g. RGD-based motifs) and may contain charged residues. MAX5 (VKVKVKVKV$^D$PPTKVK$\underline{E}$KVKV-NH$_2$) was prepared to investigate the possibility of incorporating a charged residue on the hydrophobic face of MAX1. The sequence contains a glutamic acid residue at position 16 which is negatively charged at basic pH where MAX1 normally folds and assembles. CD spectroscopy confirmed that 150 μM solutions (pH 9.0, 125 mM Borate, 10 mM NaCl) of MAX5 exist as random coil indicating that negative charges are not tolerated on the hydrophobic face (data not shown). However, alterations to the hydrophilic face of MAX1 are well tolerated. Sequences in which one or two lysine residues are replaced with other residues such as cysteine, serine, and glutamic acid are capable of folding and self-assembly into rigid hydrogels (data not shown).

Figure 13:
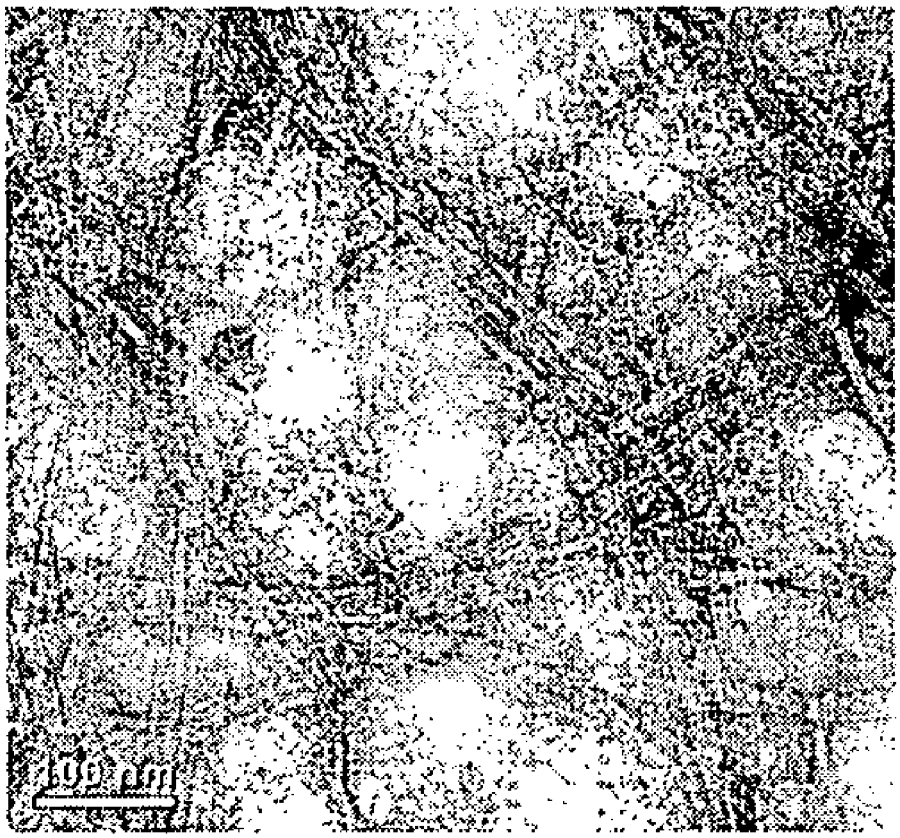
FIG. 13 shows a TEM micrograph of MAX9 fibrils negatively stained with uranyl acetate. This stiff, irreversible fibrils are due to the nonfolding nature of MAX9 and lead to no hydrogelation.

The peptides described above contain identical turn sequences, namely (-V$^D$PPT-). This sequence has a strong propensity to form a type II' turn and therefore helps to drive intramolecular folding. Since intramolecular folding must occur prior to self-assembly, alterations to this turn sequence that inhibit turn structure formation can be used to modulate intramolecular folding and self-assembly leading to hydrogelation. MAX9 was prepared to probe the importance of the turn region (VKVKVKVKV$^L$PPTKVKVKVKV-NH$_2$). MAX9 is identical to MAX1 with the exception that the $^D$Pro at position ten has been replaced with $^L$Pro. Unlike the dipeptide $^D$Pro$^L$Pro contained within MAX1 that favors type II' turn formation, the $^L$Pro$^L$Pro motif of MAX9 favors an open conformation. The two strands emanating from an open $^L$Pro$^L$Pro conformation would be projected in opposite directions. Thus, intramolecular folding resulting in β-hairpin formation would be highly unfavored. Any observable self-assembly would likely result from the direct intermolecular association of extended peptide conformers. CD of a 150 μM solution of MAX9 under folding conditions showed only random coil even after four hours (data not shown). Also, 2 wt % solutions of MAX9 failed to undergo hydrogelation and remained a low viscosity solution for days. Interestingly, after one week, self-assembly did occur but did not result in hydrogelation. Instead, long fibrils were observed that have dimensions consistent with self-assembled, extended conformers of MAX9, FIG. 13. This is strong support that intramolecular folding into a β-hairpin conformation is necessary for self-assembly into hydrogel and that the mechanism leading to hydrogel is distinct from the mechanism leading to extended fibril. In some embodiments, turn sequences can be incorporated that serve as cell adhesion sites. For example RGD binding epitopes are commonly found within turn regions of proteins important in cell adhesion events.

In one aspect, the present invention provides peptides having designed sequences that fold only in the presence of a desired environmental stimulus resulting in a hydrogelation system that is triggered on cue. The ability to control material formation temporally and spatially allows one to fully control the processing of the material. Specific to preparing hydrogel-cell constructs for tissue engineering applications, controllable hydrogel formation can take place in vitro and/or in vivo depending on the nature of the triggering mechanism. For example, MAX1 is unfolded under acidic solution conditions (pH<9, 10 mM NaCl) but rapidly folds and self-assembles within seconds when the pH is adjusted to 9 (10 mM NaCl) at temperatures greater than 25° C. Peptides were also presented that fold in response to changes in temperature. For example MAX2 is unfolded at pH 9 (10 mM NaCl) when the temperature is below 40° C., but folds/self-assembles when warmed to temperatures greater than 45° C., FIG. 9B. We have also demonstrated that the temperature at which folding occurs can be predictably modulated. It is important to point out that designing folding triggers is only made possible by understanding the fundamental principles that govern the folding and self-assembly process.

Hydrogelation of peptides discussed thus far has occurred at basic solution conditions (pH=9) in the presence of 10 mM NaCl. It is desirable to trigger hydrogelation at biologically relevant conditions, namely pH 7 in the presence of 150 mM NaCl. In fact, initiating folding and self-assembly at these solution conditions is possible with MAX1. FIG. 14A shows CD data indicating that at pH 7 (20 mM Tris) the folding of MAX1 is dependent on salt. In the presence of 20 mM KF, MAX1 is unfolded, but in the presence of 150 mM KF, MAX1 folds and self-assembles. Optically transparent KF is used for CD studies since 150 mM solutions of NaCl produce significant signal scatter at low wavelengths. The salt triggered folding event is further confirmed by FTIR which shows that the amide I band at 1643 cm$^{-1}$ (random coil) shifts to 1616 cm$^{-1}$ (β-sheet) upon the addition of KF at pH 7 for 1 wt % preparations (data not shown). NaCl is also capable of triggering hydrogelation at pH 7, adding NaCl (final concentration=150 mM) to an aqueous solution of MAX1 results in self-assembly affording rigid hydrogels (3000 Pa at 2 wt %, data not shown). For the formation of hydrogel-cell constructs, initiating hydrogelation by the addition of cell growth media would be ideal. Since DMEM growth media contains NaCl as well as other salts (~400 mM in total salt concentration) it can be used as a trigger. 2 wt. % aqueous solutions of MAX1 will undergo hydrogelation on the addition of serum free DMEM growth media. FIG. 14B shows frequency sweep data for the resultant viscoelastic, rigid gels. Additional folding triggers may be used to initiate folding including, but not limited to, specific ion binding (e.g., calcium binding) and/or electromagnetic radiation (e.g., light).

Figure 15:
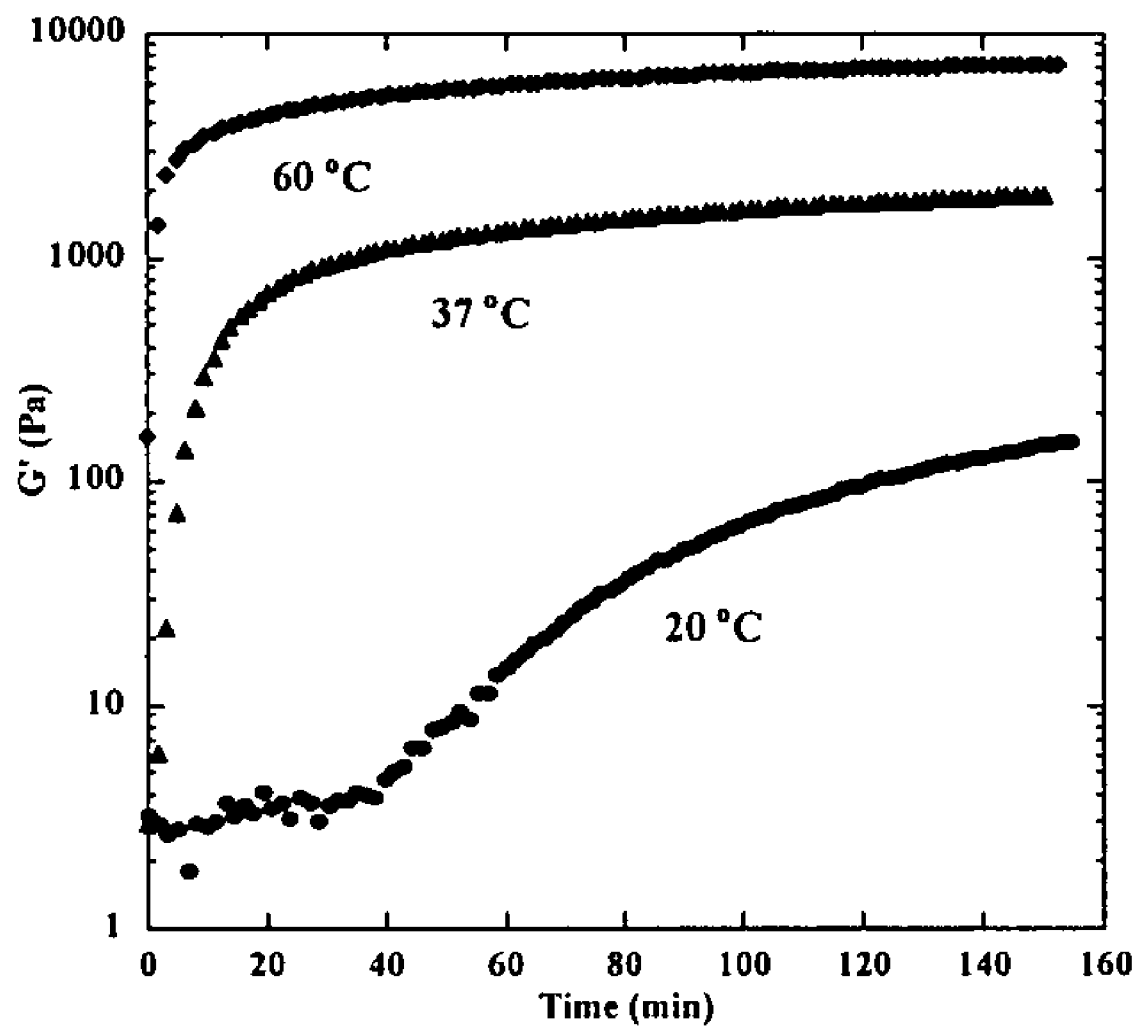
FIG. 15 shows the storage modulus of 2 wt % MAX1 versus time at different temperatures (pH 7.4, 1% strain, 6 rad/s). ●=20°, ▲=37° C., and ♦=60° C. The higher the temperature, the more quickly the peptide folds and assembles and the more rigid the resultant hydrogel network.

Those skilled in the art are aware that the mechanical properties of material substrates affect cell-material interactions. For example, it has been recently shown that vascular smooth muscle cells migrate from less rigid to more rigid areas of crosslinked polyacrylamide substrata. Also, a direct correlation between the rate of dorsal root ganglion neurite extension and agarose hydrogel rigidity has been shown. The present invention allows the modulation of the rigidity of hydrogels (e.g., MAX1 containing hydrogels) via peptide concentration and peptide folding triggering conditions, namely salt concentration and temperature. FIG. 15 shows the rigidity of 2 wt % MAX1 hydrogels at constant salt concentration and pH 7.4 assembled at different temperatures. The bulk modulus of the final networks is tunable over 3 decades from low to high temperature. Importantly, when MAX1 assembly is triggered with temperature the process is irreversible and thus the gel stiffness achieved at each triggering temperature is maintained when taken to physiological temperature. The tunability of hydrogel stiffness will allow correlation between hydrogel rigidity and cellular behavior such as adhesion and proliferation.

The present invention demonstrates that the folding triggers described herein can be used to form hydrogels that support the adhesion and proliferation of fibroblasts (NIH 3T3, mouse). These cells were used as a model system because of their importance in connective tissue development and their easily distinguished morphology when adhered to the hydrogel scaffold. Qualitative studies were performed in which cells were added to either polystyrene control wells or wells containing a uniform slab (3 mm thick) of MAX1-hydrogel. Cell adhesion was qualitatively monitored via direct observation of cell spreading after four hours from the time of initial cell seeding by optical microscopy (a quantitative cell attachment assay is described below, see also Akiyama, S. K. Functional analysis of cell adhesion: Quantitation of cell-matrix attachment, 2002; Vol. 69, pp 281-296). Non-adhered fibroblasts have rounded morphologies and adhered fibroblasts have spread morphologies Proliferation was measured both qualitatively by optical microscopy and quantitatively by a $^3$H thymidine-based cell seeding assay as described below. Hydrogels were prepared in 48 well tissue culture plates by either one of the following protocols. Protocol 1: MAX1 was dissolved in water (resulting in an acidic solution, pH~5) and an equal volume of buffer (pH 9, 250 mM borate, 20 mM NaCl) was added at room temperature to induce folding/self-assembly resulting in a 2 wt % hydrogel. The resulting gel was bathed in DMEM containing 10% calf serum and 10 mg/mL gentamicin. This allowed media to permeate throughout the gel and adjust the pH to 7.3 The storage moduli (rigidity) of gels prepared by protocol 1 are about 1600 Pa. Protocol 2: MAX1 was dissolved in water and an equal volume of serum free DMEM containing 10 mg/mL gentamicin was added to induce folding/self-assembly affording 2 wt % hydrogels. Depending on the experiment, DMEM containing calf serum can then be added to introduce serum proteins. The storage moduli of gels prepared by protocol 2 are about 1200 Pa. FIG. 16A shows that after four hours (in the presence of serum) fibroblasts have adhered to the surface of the gel as indicated by their spread out morphology. Proliferation of the cells occurs until confluency is reached, usually around 72 hours if $10^4$ cells are initially plated, FIG. 16B. Cells remain viable for at least a month as long as fresh media is provided (we stopped the assay after 1 month). Cells added to control wells containing no gel show similar behavior, FIGS. 16 C and D. In FIGS. 16A-D, cells are plated in the presence of DMEM containing 10% calf serum. Serum proteins may help mediate cellular adhesion to the hydrogel by first coating the scaffold. To determine if the hydrogel scaffold alone is conducive to cell adhesion, cells were plated onto 2 wt. % hydrogels in the absence of serum. FIG. 16E shows that the fibroblasts begin to attach and spread after about four hours even in the absence of serum proteins, but to a lesser extent as compared to the serum containing cultures. Addition of serum after four hours, results in cell proliferation, reaching near confluency after 72 hours, FIG. 16F. Identical control experiments performed in wells without hydrogel, showed that the cells behaved similarly. These experiments demonstrate that the peptidic surface provided by the hydrogel scaffold is amenable to fibroblast adhesion in the presence of serum proteins and to a lesser extent when serum is not present. The incorporation of cell binding epitopes in peptides used in hydrogel formation may be used to enhance cell adhesion in the absence of serum. This optical microscopy data qualitatively shows that MAX1 hydrogels support fibroblast proliferation.

Figure 17:
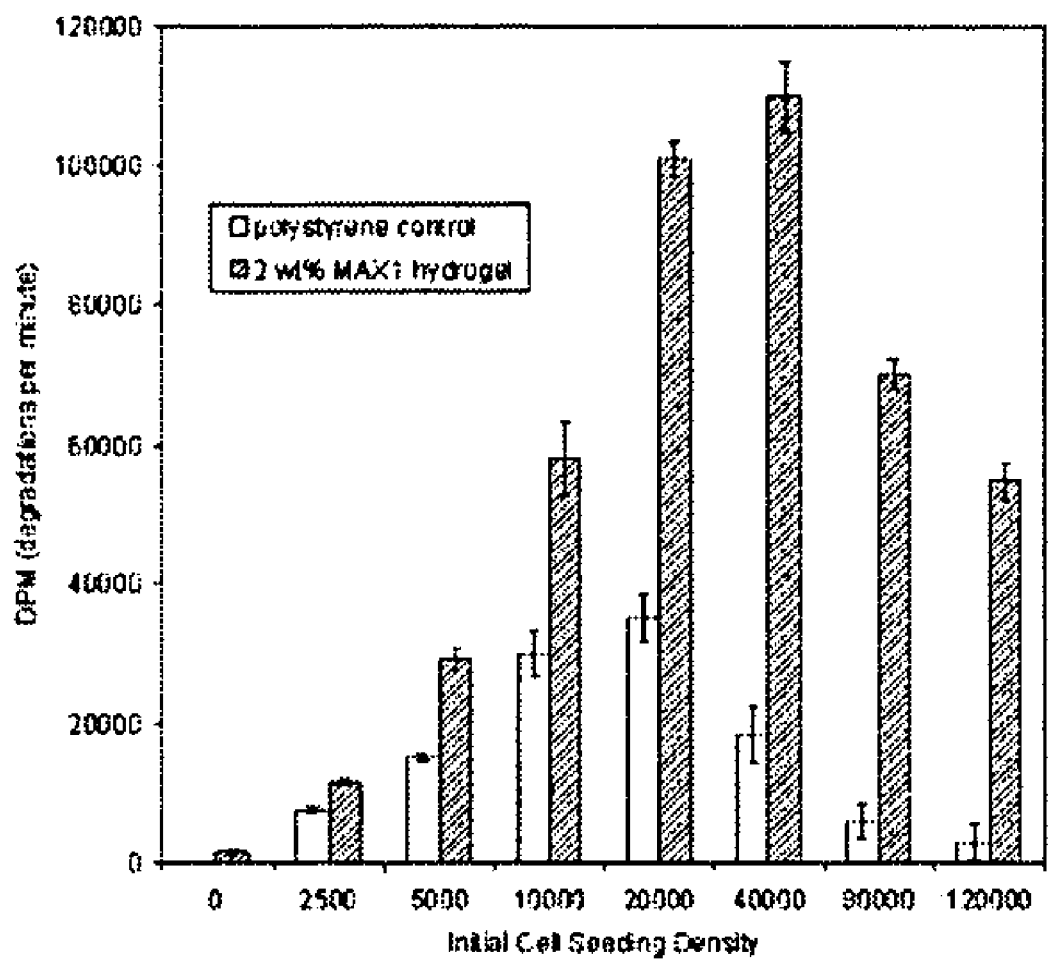
FIG. 17 shows the results of a proliferation assay of NIH 3T3 fibroblasts on MAX1 hydrogels versus cell culture polystyrene at varying initial cell seeding densities. The clear bars indicate cell proliferation on tissue culture polystyrene control while the shaded bars are the cell proliferation on 2 wt. % MAX1 hydrogel. The proliferation on the self-assembled hydrogel was higher than the control at all cell seeding densities.

A quantitative assay that could be used to measure the rate of cell proliferation was developed. This allows gels having different material properties and constituent peptide sequences to be compared in terms of how well they support proliferation. Standard colorimetric assays such as the MTT and XTT have proven unsuitable for use with hydrogels of the invention. These assays rely on the ability of cells to metabolize tetrazolium derivatives to their corresponding colored formazan analogs. The analogs permeate into the hairpin hydrogel and become immobilized making subsequent quantification by UV spectroscopy unreliable. This problem has been addressed by utilizing $^3$H thymidine-based assays in which thymidine is incorporated into proliferating cells undergoing DNA replication. This method does not require the solubilization of an analyte and unincorporated thymidine is easily washed from the hydrogel scaffold making quantification of only incorporated thymidine possible. The assay is two-fold. First, a cell seeding experiment may be performed to determine the optimal number of cells that should be plated if one wishes to follow proliferation over a given time period without the cells reaching confluency (48 hours is chosen here for convenience). Second, a proliferation rate may be determined for a given material by seeding the cells (at optimal density) onto the material and determining the number of cells undergoing DNA replication at discrete time points up to 48 hours when confluency is reached. Shown in FIG. 17 are results from a $^3$H thymidine cell seeding experiment that allows one to determine the optimal cell seeding density for hydrogels of the invention. Cells to be assayed (e.g., fibroblasts) may be seeded onto either MAX1 hydrogels or a polystryene control surface at different initial densities. After 48 hours, the growth media can be removed and replaced with media containing $^3$H thymidine and incubated for three hours. Unincorporated thymidine may be washed out (washes may be assayed until $^3$H thymidine is no longer detected) and the cells sacrificed for scintillation counting. The data shows that for 2 day proliferation assays involving MAX1 hydrogels, 40,000 fibroblasts should be seeded providing an optimal rate of proliferation. It should be noted that the optimal seeding density for polystyrene is different (20,000); it is known that any given cell type will display different optimal seeding densities for distinct materials (and different cell types will have different optimal seeding densities for one given material). Therefore, for each new material, similar cell seeding experiments may be performed before rates of proliferation are determined. This data also suggests that after 48 hours, more cells have grown on the hydrogel than on the control surface (comparing degradations (counts) at each surface's respective optimal seeding density). A possible explanation is that the three dimensional porosity of the hydrogel scaffold allows cells to proliferate into the hydrogel, which is not possible with a two dimensional polystyrene surface. This data shows that a quantitative proliferation assay has been established. One of ordinary skill in the art can use the assay described herein to study the effects of peptide sequence and hydrogel rigidity on cell proliferation.

The experiments outlined in FIGS. 16 and 17 entail plating the cells onto the two-dimensional surface of gel. Assays accessing adhesion and proliferation on the surface of two dimensional gels allow facile comparison among different hydrogel scaffolds and the results can be directly compared to materials in the literature since this is the most common technique to investigate material-cell interactions.

Figure 18:
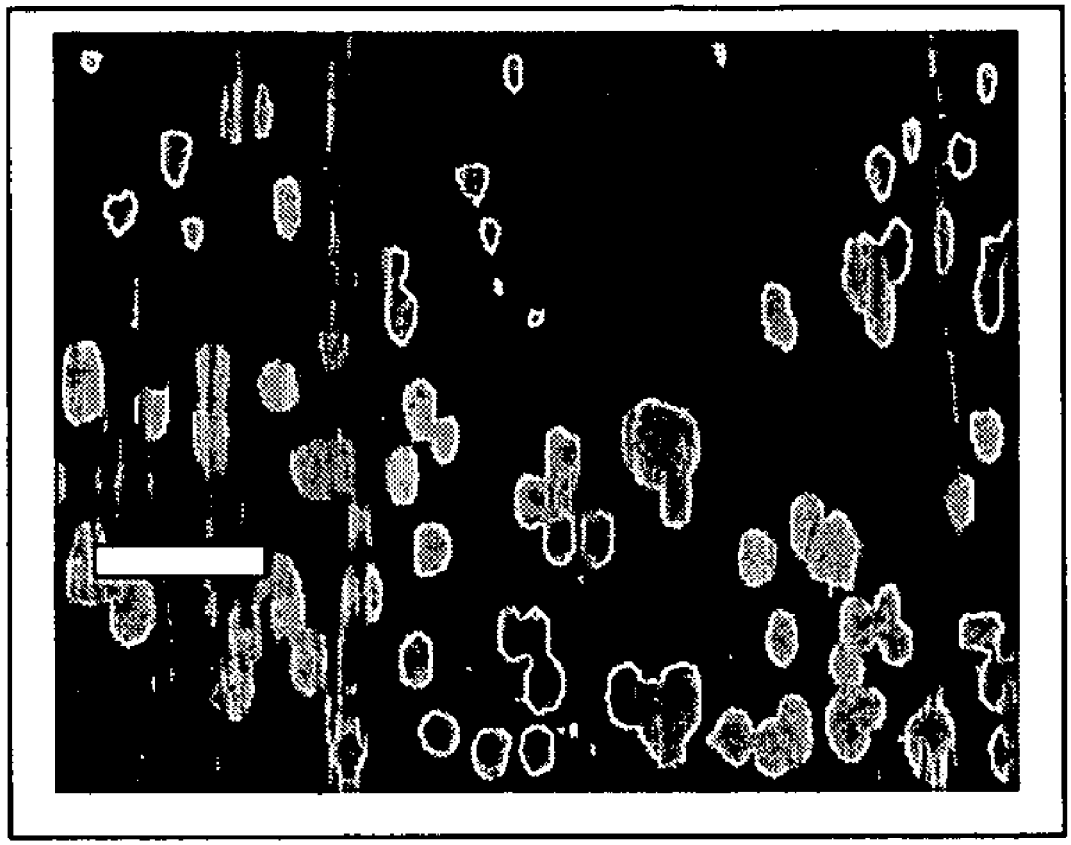
FIG. 18 is an LSCM image showing that fibroblasts are impregnated throughout the MAX1 hydrogel. Z-stack image viewed perpendicular to Z-axis. Bar=100 μm Therefore, due to the self-assembly mechanism of hydrogel formation, cells can readily be encapsulated in three dimensions.

The present invention also encompasses hydrogel-cell constructs in which cells are incorporated throughout the gel scaffold in three dimensions. This can be accomplished by initiating the hydrogelation of aqueous solutions of MAX1 via the addition of serum free DMEM that contains fibroblasts. Scaffolds that mimic a cell's 3-D in vivo environment will provide additional insights into cell-material interactions not evident in two dimensional studies. FIG. 18 shows an LSCM image of a 2 wt. % MAX1 hydrogel prepared in this manner. The image is constructed so that one can view the interior of the gel from the side. Cells stained with cell tracker green (CMFDA, Molecular Probes) are seen throughout the gel with a slightly larger concentration near the bottom of the gel where cells begin to settle before gelation is complete. One of ordinary skill in the art will appreciate that any cell type of interest may be used in conjunction with the present invention. For example, cells that may be used include, but are not limited to, yeast cells, plant cells and animal cells. Suitable cells are commercially available from, for example, known culture depositories, e.g., American Type Culture Collection (Manassas, Va.), and commercial sources known to those in the art. Preferred animal cells for use in the methods of the invention include, but are not limited to, insect cells (most preferably *Drosophila* cells, *Spodoptera* cells and *Trichoplusa* cells), nematode cells (most preferably *C. elegans* cells) and mammalian cells (including but not limited to CHO cells, COS cells, VERO cells, BHK cells, AE-1 cells, SP2/0 cells, L5.1 cells, hybridoma cells and most preferably human cells such as 293 cells, PER-C6 cells and HeLa cells). In addition, primary cell cultures, tissue homogenates, and/or cells derived from tissue homogenates may be used in conjunction with the present invention.

Figure 2B:
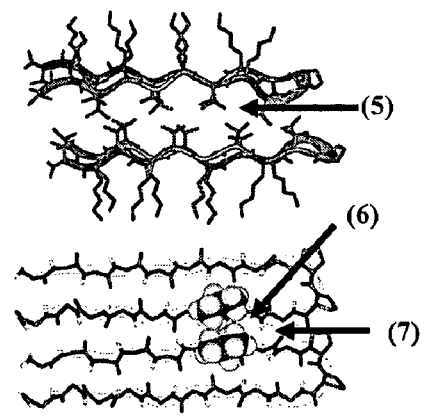
FIG. 2B-*describes* manipulations to influence intermolecular self-assembly and include: 5) hydrophobic, van der Waals interactions between neighboring folded peptide valine-rich faces, 6) hydrophobic, van der Waals interactions between peptide backbone arms of neighboring peptides, 7) hydrogen bonding between peptide backbone arms of neighboring peptides.

With regard to FIG. 2, electrostatics, H-bonding and hydrophobic interactions all play a role in folding and self-assembly. Varying electrostatics and lateral inter- and -intramolecular hydrophobic contacts for folding and self-assembly can be used to vary the material properties and/or formation conditions of the hydrogels of the invention. In addition, varying the turn region of the hairpin may also be used to modulate the characteristics of the hydrogels of the invention. Without wishing to be bound by theory, it is believed that self-assembly is governed by the interplay of two factors: 1) hydrophobic collapse of hairpins; and 2) intermolecular H-bond formation. The interplay of these two factors results in scaffolds composed of short segments of fibril interspersed with hydrophobically associated interfibril junctions, FIG. 1. One of ordinary skill in the art, given the teachings set forth herein, can alter the sequences (and hence physical nature) of the peptides used in order to modulate the contribution of either or both of these factors in order to produce a hydrogel having any desired characteristics.

The intermolecular interactions outlined in FIG. 2 may be varied to control the self-assembly process and resultant material properties, such as the degree of gel porosity which is important for cell proliferation. Specific examples of hairpins composed of 20 residues have been provided herein. The present invention also encompasses peptides both longer and shorter than this and the length of the peptides used may be varied so as to influence material properties of the resulting hydrogels.

The present invention also encompasses peptides having one or more amino acid substitutions as compared to the turns of the peptides used in the specific examples. Any turn sequence know to those skilled in the art may be used in conjunction with the present invention.

In some embodiments of the invention, one or more functional moieties, which may be peptide sequences, organic molecules or other molecules, which may be incorporated into the peptides at, for example, the side chains of the amino acids emanating from the hydrophilic face, the side chains of the amino acids emanating from the hydrophobic face, the side chains of the amino acids comprising the turn sequence, within the primary sequence of one or both strands of the hairpin, and/or within the primary sequence of the turn sequence. Specific examples of such functional moieties include, but are not limited to, peptide sequences (e.g., cell adhesion epitopes, nuclear localization signals, etc), and receptor agonists and/or receptor antagonists (e.g., cholesterol derivatives and the like), peptidomimetics, cyclic peptides, metal chelators, fluorescent and spin active probes and small molecule therapeutics. Peptides comprising one or more of such functional moieties may be analyzed by spectroscopy, light and neutron scattering, microscopy, and rheology techniques as described herein in order to produce a hydrogel having the folding/self-assembly characteristics and/or material properties desired.

In order to vary the contribution of forming intermolecular facial and lateral hydrophobic contacts relative to constant H-bonding, peptides based on MAX1 may be prepared. Such peptides may have the same number of residues but contain amino acids of varying side chain hydrophobicity on the hydrophobic face of the folded hairpin. Thus, the number of possible intra- and intermolecular H-bonds formed during folding and self-assembly is constant but the surface area of the hydrophobic face varies. Examples of peptides that may be prepared include, but are not limited to, those of the general sequence X̲KX̲KX̲KX̲KV$^D$PPTKX̲KX̲KX̲KX̲-NH$_2$ where X̲=valine, MAX1; X̲=isoleucine, MAX34; and X̲=phenylalanine, MAX33. Molecular modeling (Insight/Discover) indicates that the surface areas of these peptides increase in the order MAX1<MAX34<MAX33. Varying the surface area may effect various parameters of the hydrogels, for example, may decrease the temperature at which each peptide folds and self-assembles (T$_{gel}$) as monitored by CD (see FIG. 9). Also, the rheological properties of each peptide may be different; more hydrophobic peptides may lead to more rigid hydrogels. In addition, the rate of hydrogelation may be affected with more hydrophobic peptides forming hydrogels faster. Rate of hydrogelation can be determined by rheology (see FIG. 12). Cryo-TEM can be used to determine if these design changes affect the nano-scale structure of the hydrogel (e.g. as the hydrophobic surface area increases the number of interfibril junctions in the self-assembled state may increase) and LSCM can be employed to assess changes in micro-scale structure (e.g., changes in gel porosity). Varying the nature and number of amino acid residues emanating from the hydrophobic face of the folded peptides and/or varying the nature and number of functional moieties emanating from the hydrophobic face of the folded peptides may be used to vary the material characteristics of the hydrogels thus formed.

In order to vary the contribution of forming intermolecular hydrogen bonds during self-assembly, peptides may be prepared that have a greater or lesser capability of forming intermolecular hydrogen bonds. For example, derivatives of MAX1 containing Nα-alkylated lysine residues may be prepared. Lysine residues in MAX1 are sequentially positioned such that they are able to form intermolecular H-bonds with neighboring hairpins during self-assembly, FIG. 3A. Alkylating one or more lysine residues within each strand of a hairpin may inhibit self-assembly leading to hydrogelation. Examples of such peptides include, but are not limited to, (VKVKVKVKV$^D$PPTKVKVKVKV-NH$_2$) and (VKVKVKVKV$^D$PPTKVKVKVKV-NH$_2$), which have the sequence of MAX1, but contain Nα-butylated lysine residues at the bold positions. One of ordinary skill in the art will readily appreciate that by varying the amino acid residues and/or functional moieties attached to the amino acid residues, other peptides having a modulated (increased or decreased) capability of forming intermolecular hydrogen bonds may be constructed. It is known that the self-assembly of human amylin into fibrils has been inhibited by peptides containing N-butyl residues. CD spectroscopy and rheology may be used to assess the ability of these peptides to fold and self-assemble into hydrogel under varying folding conditions.

In some embodiments, peptides may be constructed so as to take advantage of intermolecular interactions to control the self-assembly process and resultant material properties. For peptides that fold and self-assemble via a combination of hydrophobic collapse and intermolecular H-bonding, temperature may be used to control the degree to which each of these processes contributes to the self-assembly mechanism. As discussed above, each peptide has a characteristic temperature at which it folds (T$_{gel}$) and begins to self-assemble. In addition, it has been well demonstrated in the literature that temperature can be used to drive hydrophobic collapse. Therefore, for any given peptide, if just enough heat is supplied to fold but not greatly enhance hydrophobic collapse, then H-bonding may predominate the self-assembly mechanism and resulting hydrogel scaffolds may be composed of longer segments of fibril structure. Resultant hydrogels may be characterized by larger pore sizes. Conversely, subjecting peptide to extreme temperature where hydrophobic collapse is kinetically favored over H-bonding may result in scaffolds having shorter fibril segments and more interfibril crosslinks. Resultant gels may have smaller pore sizes. Therefore, temperature control provides a general way to control nano- and microscopic features in the gel. In some embodiments, peptides may be assembled at two different temperatures (T$_1$=T$_{gel}$ and T$_2$=T$_{gel}$+30° C.). Resultant hydrogels may be visualized via cryo-TEM and LSCM to assess nano- and microscale properties. Gels containing more interfibril crosslinks may be more rigid; this can be verified via rheology.

In some embodiments, peptides may be prepared that vary in sequence length, for example, based on the general structure of MAX1, namely VK(VK)$_m$VKVKV$^D$PPTKVKV (KV)$_n$KV-NH$_2$, where m=1-20 and n=1-20 and m may be the same or different as n in any given peptide. Peptides composed of longer strand regions may form more rigid gels because of the increased hydrophobic surface area of longer hairpins. Peptides composed of longer strand regions that afford more rigid gels could be used to incorporated functional moieties. It has been shown that monomeric hairpins are most stable when their strands are approximately 7 residues in length and lengthening them doesn't increase hairpin stability. Hydrogels of peptides having longer strand regions may be prepared and their rigidity assessed, for example, via rheology under identical folding conditions.

In some embodiments, one or more amino acids of the turn region may be substituted and/or modified as compared to the turn region of MAX1. In some embodiments, turn sequences may be incorporated that not only play a structural role but also play a biofunctional role. For example, RGD binding epitopes are normally found within turn regions of proteins known to be important in cell adhesion events, and residues that flank RGD provide additional specificity to the binding event. Incorporating these epitopes into the turn regions of self-assembling hairpins may lead to hydrogel scaffolds having enhanced cell adhesion properties. As discussed above, incorporating a sequence that is incapable of forming turn structure results in a peptide (MAX9) that can not fold and does not form hydrogel. However, peptides that contain alternate turn sequences that are capable of adopting turn structure but are not as promotive as the -V$^D$PPT- of MAX1 may still fold and undergo hydrogelation. In the context of MAX1, peptides may be prepared in which the tetrapeptide sequence -V$^D$PPT- is replaced with sequences that vary in their inherent propensity to form turn structure, from weak turn formers to strong turn formers. The ability of each peptide to intramolecularly fold and self-assemble may be determined by CD and the rheological properties of their corresponding hydrogels may be studied to identify hydrogels with desired characteristics (e.g., their suitability as possible scaffolds for tissue engineering). Examples of peptides that may be prepared include, but are not limited to, VKVKVKVK-XXXX-KVKVKVKV-NH$_2$ (SEQ ID NO:12), where -XXXX- is -V$^D$PGT-, very strong turn; -A$^D$PGT-, strong turn; -VNGT-, moderate turn; -VGGT- (SEQ ID NO:13), weak turn.

In some embodiments, functional moieties (e.g., cell adhesion epitopes) may be incorporated at one or more of: a) onto one or multiple side chains of amino acids in the β-strand portion of the peptides, b) within the primary sequence at the ends and middle portions of the β-strands, c) at positions that flank the turn region, d) onto the side chain of one or more of the amino acid residues forming the turn sequence, and/or e) within the primary sequence of the turn sequence. An example of a functional moiety that may be used is the simple tripepetide RGD. The sequences may be varied depending on the intended use of the hydrogel. For example, if the hydrogel is intended to be used as a scaffold for cells, the functional moiety may be varied depending on the known sequences to elicit adhesion of specific cell types to be used. Examples of specific adhesion sequences for various cell types are presented below. Peptides in FIG. 19 may be prepared (sidechain modified peptides will be synthesized using well established orthogonal protection strategies) and studied by CD and rheology to establish their folding and rheological properties. Hydrogels prepared according to this embodiment may have enhanced cell adhesion and proliferation characteristics.

In some embodiments, concentration of folded monomer present before self-assembly may be varied in order to produce a hydrogel having desired characteristics. CD may be used in concert with dynamic light scattering (DLS) to determine a concentration of folded monomer that must be present in order for self-assembly to occur. DLS allows direct monitoring of nanostructure growth due to the self-assembly process. Distributions of particle sizes above 5 nm up to 1 micron can be readily observed. For example, using MAX1, CD may be used to monitor the rate of β-sheet formation at 20° C. The extent to which the magnitude of CD signal can be attributed to intra- (due to folding) vs. intermolecular (due to self-assembly) β-sheet formation may be determined via a real-time comparison of the growth of CD β-sheet signal to the growth of self-assembled particle size for identical solutions (μM peptide concentrations). Importantly, folded monomers will not give rise to a growth of particle size in DLS. Therefore, if a significant amount of β-sheet structure is observed by CD without concurrent particle size growth then it can be concluded that a significant population of folded monomer must be present in order for self-assembly to occur. Conversely, if particle self-assembly occurs concurrently with CD β-sheet signal growth then one can conclude that self-assembly immediately follows intramolecular folding. A similar real-time comparison may be made between particle size growth in DLS and storage modulus growth monitored via rheology. Millimolar peptide concentrations will be used so that direct comparisons between DLS and rheology can be made. The threshold of particle size above which network rheological properties are introduced will be directly observed.

In some embodiments, hydrogels of the invention may exhibit an enhanced processibility. The processibility of the hydrogels of the invention may be enhanced as compared to hydrogels known in the art as a result of designing peptides having one or more active intramolecular folding triggers that allow peptide solutions to undergo hydrogelation on cue. As shown above, the ability to trigger folding provides a direct means to control self-assembly and consequent hydrogel formation. In addition, a specific example of a suitable peptide secondary structure (i.e., the hairpin motif) has been provided, which is an ideal molecular scaffold in which triggering elements can be easily incorporated. In some embodiments of the invention, hairpins can be designed to undergo hydrogelation in response to physiologically relevant stimuli such as pH, ionic strength and temperature. In terms of processibility, triggering folding enables both in vitro and in vivo hydrogelation strategies. In additional embodiments of the invention, additional avenues may be used to trigger hydrogelation, for example, electromagnetic radiation (e.g., light) and specific ion binding (e.g., calcium ion binding). Using electromagnetic radiation to trigger hydrogelation offers a convenient means to induce spatially resolved material formation in vivo via fiber optics. For example, low viscosity peptidic-cell suspensions can be administered and subsequently gelled locally by irradiation. The ability to trigger hydrogelation ex vivo via stimuli naturally found in tissue provides another convenient means of controlling material formation. Peptides may be prepared that undergo hydrogelation in response to specific ion binding (e.g., calcium ion binding). When calcium ion is used as a specific ion, resultant materials would not only serve as scaffolds upon which cells could proliferate but also provide a source of calcium that would be released upon biodegradation of the peptide scaffold.

In the design of hydrogels of the invention, the folding and self-assembly process may be characterized by any suitable technique known to those skilled in the art, for example, CD and FTIR. Material nano- and microscale porosity may be determined via cryoTEM, LSCM, USANS, and SANS and material rigidity may be measured by rheology (using, for example, the methods described herein). The efficiency of the triggering process may also be examined. In some embodiments, triggering systems for peptides intended for in vivo hydrogelation may be those affording fast hydrogelation leading to rigid, porous gels. The rate of trigger-induced sheet formation for dilute solutions of peptide may be determined by CD and the rigidity of corresponding 1-2 wt % hydrogels may be determined by oscillatory rheology. For in vitro applications, fast gelation kinetics may be desirable but aren't necessary. In a specific example, MAX1 may be used as a model system to investigate the effectiveness of each trigger discussed below. However, once the viability of a particular trigger has been established in the context of MAX1, the trigger can be incorporated into other peptide sequences that display desired attributes distinct from MAX1.

In some embodiments of the invention, electromagnetic radiation (e.g., light) may be used to trigger the hydrogelation a peptide of the invention. Examples of suitable methodology include those depicted FIG. 20. The embodiments depicted in FIG. 20 include the use of photocages to inhibit folding. Such photocages may be incorporated in the peptides of the invention, for example, at the side chains of residues comprising the hairpin and/or within the peptide backbone. Folding and consequent self-assembly may be initiated by exposing aqueous solutions of peptide to light.

As discussed above, incorporating charged residues into the hydrophobic face of the hairpin (e.g. Glu) inhibits folding and consequent self-assembly. This inhibition may be utilized to inhibit folding via the incorporation of the negatively charged photocage (2-nitrophenylacetic acid) on the hydrophobic face. In one embodiment, the amino acid residue at position 16 of MAX1 may be replaced with a cysteine (MAX6) and may be alkylated with 2-bromo-2-(2-nitrophenyl)acetic acid according to literature protocol affording the caged peptide (Pan & Bayley, *Febs Letters* 1997, 405, 81-85). 2-nitrophenylacetic acid is a commonly used photocage and its light induced cleavage from heteroatoms has been thoroughly studied. Exposing caged peptides to light (330-360 nm) results in release of the negatively charged cage and the generation of neutral Cys on the hydrophobic face. If the nitrosoketone by-product formed during photolysis is alkylating the newly formed Cys side chain (a potentially deleterious side-reaction), 1 mM dithiothreitol may be added to quench the nitrosoketone and maintain a reducing environment. Position 16 is initially chosen for modification since a control peptide with Cys at this position folds and self-assembles. One of ordinary skill in the art will appreciate that one or more other positions in peptides may by treated in a similar fashion. Photolysis efficiency may be dependent on sequence position and thus varying the location and/or number of residues photocaged may be used to vary the properties of the resultant hydrogels. In some embodiments, the rate of photolysis may be in the micro- to millisecond time regime. Typically, the period of irradiation maybe from about a microsecond to several milliseconds, for example, from about 0.01 μs to about 1000 ms, from about 0.01 μs to about 100 ms, from about 0.01 μs to about 10 ms, from about 0.01 μs to about 1 ms, from about 0.01 μs to about 0.5 ms, from about 0.1 μs to about to about 1000 ms, from about 0.1 μs to about 100 ms, from about 0.1 μs to about 10 ms, from about 0.1 μs to about 1 ms, from about 0.1 μs to about 0.5 ms, from about 1.0 μs to about 1000 ms, from about 1.0 μs to about 100 ms, from about 1.0 μs to about 10 ms, from about 1.0 μs to about 1 ms, from about 1.0 μs to about 0.5 ms, from about 10 μs to about 1000 ms, from about 10 μs to about 100 ms, from about 10 μs to about 10 ms, from about 10 μs to about 1 ms, or from about 10 μs to about 0.5 ms. Suitable irradiation sources include may provide bulk and/or spatially resolved irradiation and may include, but are not limited to, a Nikon eclipse TE2000 inverted fluorescence microscope equipped with a mercury arc lamp and UV laser to allow spatially resolved illumination; all commercially available.

In some embodiments, the N-alkylation of peptides may be used to inhibit H-bond driven self-assembly. β-hairpins that incorporate an N-o-nitrobenzyl cage at a backbone amide nitrogen that would normally form an intramolecular H-bond (e.g. position 16 of MAX1) may be synthesized using standard techniques. A cage occupying this position may be used to inhibit intramolecular folding since intramolecular H-bonding is sterically hindered, FIG. 20. o-nitrobenzyl cages are another class of compounds whose properties are well established. Exposure to light (330-360 nm) releases the cage resulting in regeneration of a protonated amide capable of engaging in H-bond formation and consequent folding/self-assembly. The efficiency of photolysis may varied dependent on sequence position and this may be used to vary formation and/or characteristics of the hydrogels. Site specific N-alkylated peptides may be prepared by solid phase peptide synthesis (SPPS) via literature protocol (see Reichwein, et al., *Tetrahedron Letters* 1998, 39, 1243-1246 and Tatsu, et al., *Febs Letters* 2002, 525, 20-24). Since the particular cages described above have been used in cellular context, cage by-products are unlikely to be cytotoxic. However, cytocompatibility of this system may be measured via methods described in the literature (see Bryant, et al., *Journal of Biomaterials Science-Polymer Edition* 2000, 11, 439-457). Another possible concern is that using light at 330-360 nm to trigger hydrogelation in the presence of cells may lead to UV-based cellular photodamage since the o-nitro derivatives described above all involve one photon excitation to induce cleavage. Although one photon excitation has been commonly used in the context of cell-based experiments with no apparent damage to cells, if UV-based damage is observed for any particular cell type, two photon cages that absorb in the IR (e.g. coumarin derivatives) may be used (Furuta, et al., *Proceedings of the National Academy of Sciences of the United States of America* 1999, 96, 1193-1200).

Figure 20:
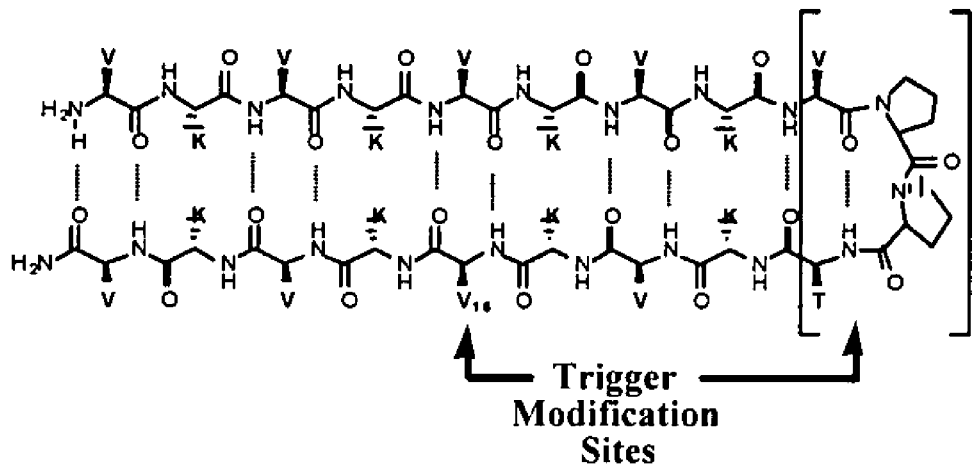
FIG. 20 shows examples of triggers that may be used in connection with the present invention. 330-360 nm wavelength light can be used as an intramolecular folding (and, thus, hydrogelation) trigger by incorporation of chemistries shown in the figure at Val(16) (schemes 1 and 2). Calcium II binding can be used as an intramolecular folding (and, thus, hydrogelation) trigger by incorporation of chemistries shown in schemes 3 and 4 into the turn sequence.

In some embodiments, binding of a specific ion may be use to trigger hydrogelation. For example, hydrogelation may be triggered via calcium ion binding. In embodiments involving binding of calcium ion, typically, in the absence of calcium ion, peptides are unfolded while the addition of calcium nucleates folding/self-assembly. As shown above, the turn region of the hairpin may be critical for promoting intramolecular folding and consequent self-assembly. In one specific example, variants of MAX1 may be prepared in which the four residue turn -V$^D$PPT- is replaced with a turn/loop sequence or unnatural chelate incapable of adopting ordered structure in the absence of metal ion. Metal binding affects turn formation which, in turn, promotes intramolecular folding and self-assembly. FIG. 20 shows the metal-triggers described in detail below.

In one specific embodiment, a variant of MAX1 is formed in which the four residue turn -V$^D$PPT- is replaced with -DR KADGYIDFEE- resulting in VKVKVKVKV DRKADG YIDFEE VKVKVKVKV-NH$_2$ (SEQ ID NO:14). This peptide should be unordered in the absence of metal but rapidly fold and self-assemble after binding Ca(II). The sequence -DRKADGYIDFEE-corresponds to a calcium binding loop contained within the EF hand domain of Troponin C. The underlined residues bind Ca(II) via both side chain and main chain carbonyls affording a pentagonal bipyramidal geometry with water occupying one of the equatorial positions. Importantly, is has been shown that this linear peptide is capable of binding Ca(II) with a low mM Kd and that the binding event leads to structure formation. The crystal structure of troponin C indicates that the N- and C-terminal residues of the calcium bound loop are within about 6 Å and that these terminal residues adopt dihedral angles conducive to antiparallel sheet formation. In fact, energy minimization and dynamics simulations with explicit solvent were performed with this designed peptide and demonstrated that this metal bound loop is geometrically well suited to nucleate β-hairpin structure in the context of MAX1.

In another specific embodiment, an additional high affinity trigger may be employed. This design invokes the use of a non-natural Ca(II) chelator DOTAM, which is a derivative of the thoroughly studied octadentate ligand DOTA, FIG. 20. DOTAM binds calcium tightly (Kd=29 nM) forming a square antiprism complex that situates the carbonyl containing arms of the ligand within 5 Å of each other, making these two positions ideal for peptide attachment. Therefore, replacing the four residue turn -V$^D$PPT- of MAX1 with the DOTAM-derivative in FIG. 20 affords a system that is unstructured in the absence of Ca(II); however, when Ca(II) binds, the two β-strands are brought within 5 Å of each other and folding is initiated. This peptidomimetic may be prepared using manual solid phase synthesis using commercially available or easily synthesized starting materials.

In some embodiments, peptide structure and material properties may be used to modulate the adhesion and proliferation of cell lines, for example, model fibroblast and osteoblast cell lines. Hydrogels described above may be useful for tissue engineering applications (e.g. those that undergo triggered material formation via biocompatible stimuli such as electrolyte concentration, temperature and light affording porous gels of sufficient rigidity to be self-supporting, >10 Pa). The present disclosure will allow one of ordinary skill in the art to correlate peptide structure, material rigidity, and cytocompatibility concurrent with identifying hydrogels that may ultimately be useful in tissue engineering. Three desirable cell level biological characteristics for tissue engineering feasibility are: a) the hydrogels should be noncytotoxic to desired cells b) the hydrogel should promote cell adhesion (attachment and spreading), and c) the hydrogel should allow cell proliferation. Hydrogels of the invention typically, although not necessarily, possess one or more of these characteristics. First, the experimental strategy for assessing cytocompatibility (parts a, b and c) will be described. Second, examples of cell lines suitable for these studies will be discussed. Third, specific experiments are described that will permit one of ordinary skill in the art to delineate the interplay between peptide structure, material rigidity and cytocompatibility and to select appropriate peptides and triggers for particular applications (e.g., particular cell types). In some embodiments, cell binding epitopes may be incorporated into the peptide to enhance material cytocompatibility. Examples of cell types that may be used include, but are not limited to, mammalian cells, NIH 3T3 fibroblasts, HEK 293, HELA cell lines, and rat calvarial MC3T3-E1 osteoblasts, neuronal cells, stem cells, and cells derived from tissue samples (e.g., brain, liver, heart, etc)).

In some embodiments, it is desirable to select peptides and triggering conditions that facilitate cell adhesion and proliferation. Typically, four hours is sufficient time for fibroblast attachment, with almost all of the cells undergoing spreading but not proliferation. Literature protocol indicates that 12 hours is sufficient for osteoblast attachment without proliferation. Therefore, fibroblast vitality may be assayed four hours following their introduction to the hydrogel, for example, by preferentially staining living versus dead cells and performing fluorescence-based imaging; osteoblasts may be assayed after 12 hours. Known numbers of respective cells may be seeded onto hydrogels preformed in tissue culture plates. After the respective time for each cell type, calcein AM or pentafluorobenzoyl aminofluorescein diacetate may be used to stain the cytoplasm of living cells. Propidium iodide may be used to stain dead cells. Parallel controls using tissue culture plates without hydrogel may be performed. If the number of dead cells in the hydrogel is higher than that observed in the control plates, then the material may be deemed unsuitable for the specific cell type. The possibility exists that cells undergoing apoptosis may resist dye incorporation leading to an incorrect assessment of hydrogel cytotoxicity. The cytotoxicity of these gels may be further verified in the adhesion and proliferation studies described below. Based on preliminary results, a majority of the proposed gels appear to be non-cytotoxic. Lastly, if the proposed dyes prove problematic, an alternate set of dyes may be used to assess cytotoxicity, for example, SYTO, a nucleic acid indicator of live cells used in combination with SYTOX, a nucleic acid indicator of dead cells.

In general, when synthetic materials are used in vitro as cell culturing substrates, cell adhesion is primarily mediated by serum proteins (e.g. fibronectin and vitronectin) present in the growth media that non-specifically coat the scaffold. However, for hydrogels that may ultimately be introduced in vivo by the triggering mechanisms described herein, the hydrogel scaffold may innately promote cell adhesion in the absence of serum proteins. This ensures cell attachment when a potential host does not provide a mechanism to introduce cell adhesion proteins to the scaffold. Hydrogels of the invention may promote cell adhesion both in the presence and absence of 10% calf serum. An assay may be used to identify appropriate hydrogels for cell attachment in which cell attachment is radiologically quantitated by determining the fraction of attached versus unattached cells after gentle washing. Specifically, 1) a cell line of interest (e.g., mammalian fibroblasts or osteoblasts) may be cultured and pre-labeled for 24 hours with $^3$H thymidine; unincorporated label may be removed by washing and a two hour chase. 2) Known concentrations of labeled cells may then be introduced to both untreated tissue culture wells (control) and wells comprising a hydrogel of the invention. In wells containing hydrogel, cell growth media with or without calf serum may be added. 3) The kinetics of cell adhesion may initially be monitored, for example, over six hours for fibroblasts in time increments that may be experimentally determined by one of ordinary skill in the art using routine experimentation. The kinetics of osteoblast adhesion may initially be monitored over 24 hours. These end time points may be experimentally refined; enough time must be given to allow attachment and spreading but not proliferation. Also, a potential problem with end points that are too long is that some cells, if incubated for extended times, may modify the hydrogel surface via membrane bound proteases or secreted matrix proteins and allow attachment even on "non-stick" surfaces. In this scenario, attachment is promoted by the cell and not necessarily the material surface. Optimum end points may be determined by plating cells onto surfaces coated with heat denatured BSA (a typical non-stick surface). When greater than 2-3% of the cells have attached, the maximal end point has been reached. 4) At appropriate times, unattached cells may be gently washed away and counted by liquid scintillation spectrometry and attached cells may be solubilized for scintillation counting employing stand curves for quantitation. Thus comparisons can be made among polystyrene tissue culture and hydrogel surfaces with and without serum proteins. Cell spreading following attachment may be optically verified. Using the information thus generated, a suitable hydrogel may be designed to promote the adhesion of any cell type of interest. By varying the peptide structure, material properties such as rigidity and scaffold morphology may be adjusted to optimize a hydrogel's ability to foster cell adhesion. For example, simple cell spreading assays described above showed that fibroblasts efficiently attached to MAX1 hydrogels (storage modulus=1200 Pa) in the presence of serum proteins but less efficiently in the absence of serum proteins. Hydrogels having this characteristic may be useful for in vitro applications. By introducing structural modifications to the peptides and/or by preparing hydrogels of differing rigidity enhanced cell adhesion in the absence of serum proteins may be obtained. Hydrogels with enhanced cell adhesion may be used for both in vitro and in vivo applications and may be more suited for in vivo applications than hydrogels having a lower degree of cell adhesion.

In some embodiments, non-cytotoxic hydrogels that promote cell adhesion as outlined above may be used to support the proliferation of the adhered cells. Proliferation rates may be assessed using the $^3$H thymidine assay described above. For a given gel, the optimal cell seeding density may be determined, for example, by using rate experiments lasting 48 hours for fibroblasts. With reference to FIG. 17, initially seeding of MAX1 hydrogels with 40,000 fibroblasts allows proliferation to be followed for 2 days until confluency is reached. Proliferation may be followed for any suitable length of time, for example, over two days or over longer time periods. The duration of rate experiments involving other cell types (e.g., osteoblasts, neuronal cells, stem cells, etc.) may be experimentally determined in a similar manner. After the optimal seeding density has been determined, quiescent cells may be seeded onto hydrogel and the number of proliferating cells may be quantitated as a function of time via $^3$H thymidine uptake. In one embodiment, cells at optimal density may be plated onto preformed hydrogels in 24 well tissue culture plates in the presence of unlabeled media containing 10% calf serum. In triplicate, cells may be allowed to proliferate for distinct time periods (e.g. 6, 12, 18 hours, etc.). After each discrete time, growth media may be removed and replaced with media containing $^3$H thymidine. Cells may be allowed to uptake $^3$H thymidine for three hours. Unincorporated thymidine may be washed out (washes may be assayed until $^3$H thymidine is no longer detected) and the cells may be sacrificed for scintillation counting. Comparing to standard curves (which may be previously determined by culturing desired cells on tissue culture polystyrene and directly correlating cells counted by hemocytometry to scintillation counts) allows one to quantify cells undergoing DNA replication at that time. In some embodiments, the number of proliferating cells on certain hydrogels may exceed the number that could possibly fit within the two dimensional area of the hydrogel surface. In these cases, cells may have proliferated into the pores and channels of the hydrogel scaffold. In some embodiments, hydrogels of the invention may be designed to promote the proliferation of cells into the hydrogel scaffold. Hydrogels of this type may be readily identified, for example, by following the proliferation of pre-stained cells via LSCM where 3-D images may be collected as a function of time; cells that have migrated into the hydrogel interior will be clearly visible. Cells may be pre-stained with any suitable dye, for example, Vybrant CFDA SE (Molecular Probes), a green fluorescent probe that is sequestered in the cytoplasm of cells and is passed on to daughter cells (cell viability is unaffected). One of ordinary skill in the art may use assays of this type to identify hydrogels having the desired ability to promote cell proliferation. By varying peptide structure and the resultant material properties of the hydrogel such as rigidity and scaffold morphology, hydrogels may be produce that foster cell proliferation as discussed below.

The assays described above will be useful in assessing adhesion and proliferation on the surface of two dimensional hydrogels and allow facile comparison among different hydrogel scaffolds, and the results can be directly compared to materials in the literature since most published work has been performed in 2-D. As shown in FIG. 18, triggering material formation in the presence of cells allows the three-dimensional incorporation of these cells throughout the hydrogel. Non-cytotoxic hydrogels that promote cell adhesion (for example, hydrogels identified as above) may also be used as 3-D substrates. Cell attachment may be difficult to quantify since unattached cells sequestered in the interior of hydrogel can not be washed away. However, a qualitative cell spreading assay may be used to gauge cell spreading and thus attachment. Cells may be pre-stained, for example, with Vybrant CFDA SE and subsequently incorporated into the hydrogel matrix. Cell morphology of initially incorporated cells may be visualized in three dimensions by LSCM (non adhered cells will appear round and adhered cells will appear spread). In addition, since the dye is passed on to prodigy, cell proliferation can be qualitatively visualized. Proliferation rates can be quantitatively determined using the same assay as described above for the 2-D work. $^3$H thymidine diffuses readily into the hydrogel matrix and should be available to cells undergoing DNA replication.

In some embodiments, the present invention may be used to support the adhesion and/or proliferation of cells (e.g., cell lines). Such cells or cell lines may be of any type known to those skilled in the art and may be cultivated for any purpose (e.g., to generate a tissue or for expression of a desired protein). In embodiments related to tissue engineering, model cell lines may be chosen based upon their relationship to human cells involved in connective tissue and bone generation/healing in addition to their robust performance during in vitro culturing. Examples of suitable cell lines for this purpose include, but are not limited to NIH/3T3 mouse fibroblasts, an immortalized cell line, which may be used as a model of fibroblasts involved in human connective tissue development and rat calvarial (MC3T3-E1 Subclone 4) cells, which may be used as a model of human osteoblast cells. Both cell lines are well studied and a significant literature database exists allowing the performance of the proposed hydrogels to be benchmarked against previously studied materials. One of ordinary skill in the art is aware of the possible limitations using the MC3T3-E1 cell line such as their ability to revert to a non-differentiating fibroblast-like phenotype. In some embodiments, hydrogels of the invention may be used to support the adhesion and/or proliferation of cells derived from primary tissue samples, for example, primary osteoblasts from calvaria or bone marrow.

In some embodiments, the hydrogels of the invention, which may contain one or more cells and/or one or more therapeutic agents (e.g., pharmaceuticals). Hydrogels for this purpose may be identified using standard techniques in animal model systems. Hydrogels may be preformed prior to insertion into an animal or may be inserted into in the form of a solution and undergo triggered hydrogelation in situ. In some embodiments, hydrogels may be formed by peptides that undergo triggered material formation via biologically relevant stimuli. For example, a solution of peptides, which may include cells and/or therapeutic agents, may be inserted into an animal (e.g., a human) and undergo hydrogelation as a result of the one or more triggers endogenous to the animal (e.g., pH, ionic strength, etc). In other embodiments, hydrogelation may be effected using an exogenous trigger, for example, electromagnetic radiation (e.g., light). Using materials and methods of the invention, scaffolds with desired rigidity may be constructed and used in vivo. Such scaffolds may provide a substrate with optimal mechanical properties for adhesion and proliferation of cells and/or delivery of therapeutics.

In some embodiments, the present invention provides a method for predicting the cytocompatibility of a hydrogel. For example, the experimental data from the cytocompatibility assays described above may be used to draw correlations between peptide structure presented in the studied hydrogels and cytocompatibility. In some embodiments, correlations between cytocompatibility and molecular parameters such as peptide hydrophobicity, β-hairpin strand length, and other parameters discussed above may be identified and used to predict the cytocompatibility of proposed hydrogel. The molecular parameters may have been varied in order to understand and control the self-assembly process. These correlations will then allow the design of completely new peptides with both optimal material and cytocompatibility properties in an iterative design process.

In a specific embodiment, cell adhesion epitopes may be incorporated into hairpin-based hydrogels in order to enhance cell attachment in the absence of serum proteins. Enhancement in the rate of proliferation may also be measured. The two-dimensional quantitative cell attachment and proliferation assays previously described may be used. In one embodiment, cell adhesion epitopes may be incorporated into hydrogels. One of ordinary skill in the art will appreciate that there is clear experimental evidence that the addition of cell adhesion epitopes within tissue engineering matrices promotes cell attachment and/or proliferation (see, for example, Urry, *Angewandte Chemie-International Edition in English* 1993, 32, 819-841, David, et al., *Bioconjugate Chemistry* 2001, 12, 890-899, Rezania & Healy, *Journal of Orthopaedic Research* 1999, 17, 615-623, Cook, et al., *Journal of Biomedical Materials Research* 1997, 35, 513-523, Burdick & Anseth, *Biomaterials* 2002, 23, 4315-4323, Houseman & Mrksich, *Biomaterials* 2001, 22, 943-955, Kao, et al., *Journal of Biomedical Materials Research* 2001, 55, 79-88, and Schmedlen, et al., *Biomaterials* 2002, 23, 4325-4332). One or more cell binding ligands may be covalently attached to individual hairpins and self-assembled into a hydrogel matrix. One or more sequence epitopes may be incorporated at any position of the peptide, for example, at one or multiple lysine side chains or within the primary sequence of a peptide (e.g., MAX1). Any position that can tolerate the additional epitopes without adversely affecting the self-assembly as discussed above may be used.

Within the structural context of MAX1, one can incorporate one or multiple epitopes allowing precise control of the concentration of epitopes displayed. In addition, copies of epitopes can be identical or can vary in identity. For example, synergistic ligand binding sites are known to exist in α5β1; mutagenesis experiments on fibronectin demonstrate that RGD is a more effective ligand with neighboring SDV and RNS epitopes (Ruoslahti, *Annual Review of Cell and Developmental Biology* 1996, 12, 697-715). Therefore, in some embodiments, hairpins rich in epitope diversity may be prepared and used to promote cell adhesion and proliferation. In some embodiments, one or more integrin binding ligands may be incorporated. Such integrin binding ligands may be based on extracellular matrix proteins specific to fibroblasts and epitopes from bone sialoprotein specific to osteoblasts. The epitopes to be incorporated may be selected to be complementary to the cell line to be used with the hydrogel.

In one specific embodiment, a hydrogel suitable for use with 3T3 fibroblasts may be prepared. Such a hydrogel may incorporate one or more RGD epitopes known to bind α5β1. This integrin has been shown to exist in fibroblasts cultured from healthy human periodontal connective tissues (Hakkinen, et al., *Biochimica Et Biophysica Acta-Molecular Cell Research* 1994, 1224, 33-42). In specific embodiments, one or more of the peptide epitopes TRGDSP (SEQ ID NO:15), RGDG (SEQ ID NO:16), RGDY (SEQ ID NO:17), and RGDW (SEQ ID NO:18) may be incorporated into the peptides at any position and used to prepare a hydrogel of the invention. One or more copies of each epitope may be incorporated alone or in combination with one or more copies of the other epitopes.

In another specific embodiment, a hydrogel suitable for use with MC3T3 osteoblasts may be prepared. Such a hydrogel may incorporate one or more copies of the epitope FHRRIKA (SEQ ID NO:19), an epitope derived from bone sialoprotein, known to bind to heparan sulfate proteoglycans displayed on osteoblast surfaces. In other embodiments, hydrogels of the invention may incorporate an additional epitope known to positively affect osteoblast adhesion, GRGDSPY (SEQ ID NO:20). Hydrogels may be prepared with one or more copy of either epitope or with one or more copies of both epitopes in combination. Rezania & Healy (supra) have observed an increase in osteoblast proliferation when RGD-containing peptides and FHRRIKA were used together.

In some embodiments, suitable epitopes for enhancing cell binding and/or proliferation may be identified using competitive binding assays with soluble epitope. For example, if cell attachment and/or proliferation is mediated by specific ligand binding events, enhancement of attachment or proliferation should be competitively inhibited by increasing concentrations of added soluble ligand. In addition, for those peptides containing RGD sequences that lead to significant enhancements, control sequences will be prepared in which the 1-aspartic acid residue in the RGD sequence will be replaced with d-aspartic acid. It has been shown that this simple change in stereochemistry is completely deleterious to integrin binding.

The present invention also encompasses hydrogels having varying stiffness. Varying the stiffness of the gel can be used to modulate cell-material interactions, specifically cell adhesion and proliferation. Hydrogels of varying stiffness may be prepared while keeping the peptide primary sequence constant. In one specific embodiment, the peptide MAX1 may be used to prepare hydrogels of varying stiffness. The rigidity of MAX1 hydrogels may be varied by altering peptide folding triggering conditions, namely folding temperature, while holding peptide concentration constant. Based on preliminary data accessible storage moduli (gel stiffness) will range from several Pa to 10,000 Pa. MAX1 gels formed at different temperatures retain their rigidity even after being re-equilibrated at 37° C. (e.g., cell culturing conditions). By subsequently observing two-dimensional cell adhesion and proliferation on hydrogels of varying stiffness, the optimal substrate stiffness for any particular cell type (e.g., neuronal-material, stem cells, fibroblast-material and/or osteoblast-material) may be determined. Although MAX1 may be used for this purpose, the stiffness of a hydrogel may be varied using any peptide described herein. Varying the stiffness of the gel may also be used to optimize the cytocompatibility of the hydrogels.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Intramolecular folding events, triggered by the presence of salt, induce the self-assembly of β-hairpin peptides into hydrogel networks at physiological conditions. At pH 7.4, low ionic strength solution conditions, dilute, homogeneous solutions of peptide (≦2 wt. %) exhibit the viscosity of pure water. Circular dichroism spectroscopy shows that at pH 7.4 in the absence of salt, peptides are unfolded. By raising the ionic strength of solution, electrostatic interactions between charged amino acids within the peptide are screened and a β-hairpin conformation is adopted. Folded β-hairpin molecules supramolecularly assemble via hydrophobic collapse and hydrogen bonding into a three dimensional hydrogel network. FTIR and x-ray scattering data demonstrate that these hydrogels are rich in β-sheet. Dynamic oscillatory Theological measurements demonstrate that the resultant supramolecular structure forms an elastic material whose structure, and thus modulus, can be tuned by salt concentration and temperature. Storage moduli of hydrogels increase with increasing salt concentration. Robust hydrogelation is also observed in cell growth media at physiological conditions. Transmission electron microscopy reveals that the hydrogel elasticity arises from a network nanostructure consisting of semi-flexible fibrillar assemblies.

Hydrogels are collectively an important class of biomaterial that have extensive uses in tissue engineering and drug delivery applications. Self-assembly strategies provide precise control in order to construct new hydrogel materials with desired nano- and micro- structures that can be responsive to environmental conditions, such as temperature, pH, electric field, ionic strength or light. Hydrogelation of β-hairpin peptide using pH and temperature triggers has been shown (see Pochan 2003 and Schneider 2002 supra). These molecules exhibited a pH and temperature dependent intramolecular folding event that resulted in a reversible intermolecular self-assembly process leading to hydrogel scaffold formation. In general, by controlling the peptide-folding event, it is possible to design responsive materials that undergo self-assembly with desired stimuli. In addition, the self-assembly process can be controlled in order to engineer desired morphological and mechanical properties. In one specific embodiment shown below, salt concentration is used as a trigger to induce the β-hairpin intramolecular folding event followed by self-assembly into a supramolecular elastic network. The rate of folding, and thus, final gel Theological properties, may be tuned by ionic strength of the peptide solutions. Importantly, the formation of these physical hydrogels does not involve any chemical crosslinking chemistry and can be performed at physiological temperature and pH.

There are different strategies reported in the literature to make polymeric gels that are responsive to stimuli, e.g. undergo sol-gel or swelling transitions as a response to changes in physical or chemical environmental conditions. While temperature and pH are the most prevalent stimuli, ionic strength is also used to trigger gelation by phase transition, self-assembly or polymer conformational changes. The formation of salt complexes can change solution and self-assembly properties of block copolymers that form self-assembled structures like spherical or worm-like micelles. For example, the type and amount of salt has been shown to change aggregation properties and, thus, the elasticity of the networks formed by Pluronic based block copolymer systems. Chemical hydrogels of synthetic polymers such as N-isopropylacrylamide, well known to exhibit thermal responsiveness due to an LCST-type phase transition, also exhibit salt induced volume phase transitions. At relatively high salt concentrations (or at temperatures higher than the LCST), hydrophobic interactions dominate and lead to the precipitation of the chemically crosslinked polymer chains causing gel collapse. Swelling of hydrophilic networks such as poly(acrylic acid) and poly(methacrylic acid) hydrogels caused by ionic strength and pH has been explored for the potential to produce responsive biomaterials.

Gelation behavior of biomacromolecules, such as gelatin, polysaccharides, and β-lactoglobulin, is extensively studied in the literature. It is well known that by applying thermal treatments, these macromolecules undergo secondary structure (conformational) phase transitions, resulting in the formation of intermolecular network structures. For example, gelatin forms hydrogels with decreasing temperature via the formation of triple helical physical junctions. Rheological studies on gelatin gels revealed that the viscoelastic properties are highly dependent on processing conditions, such as rate of cooling, degree of undercooling and concentration. However, due to the polyelectrolyetic nature of biomacromolecule solutions, ionic strength is also a vital parameter to control assembly properties. Effects of ionic strength on biomacromolecular gel networks, such as pectin, β-lactoglobulin, welan, and gelatin have been well studied due to their importance in food processing and pharmaceutical applications. In general, increasing the ionic strength of these solutions results in an increase in network elasticity due to the formation of intermolecular salt-bridge physical crosslinks.

There is a great interest in mimicking the stimuli responsive self-assembly routes of biomacromolecules with well-defined sequences of oligo and poly-peptides because of their potential applications as responsive biomaterials. Self-assembly of oligopeptides into β-sheet rich, β-amyloid-like structures triggered by ionic strength and pH has been investigated as a biomimetic material formation strategy. For example, Caplan et al. (*Biomacromolecules* 2000, 1, 627-631) showed that self-assembly and resultant gel properties of an oligopeptide, with an alternating sequence of hydrophobic amino acid residues with positively or negatively charged amino acids, can be altered by the ionic strength of the solution. In addition, elastin-mimetic peptides (McMillan and Conticello, *Macromolecules* 2000, 33, 4809-4821), hybrid molecules with coiled-coil protein-synthetic polymer domains (Wang, et al., *Nature* 1999, 397, 417-420), and leucine zipper polypeptide domains with additional polyelectrolyte segment (Petka et al. *Science* 1998, 281, 389-392), form responsive hydrogels that undergo gelation with temperature or pH at appropriate ionic strength.

In the specific embodiment detailed below, salt-triggered physical hydrogel formation via intramolecular folding and consequent intermolecular self-assembly of a 20 amino acid β-hairpin molecule (MAX1) at low peptide concentrations (2 wt %) under physiological conditions is demonstrated. The molecule consists of two strands composed of an alternating sequence of valine (V), (isopropyl hydrocarbon side chain) and lysine (K) (primary amine capped side chain) amino acid residues that are connected with a tetrapeptide turn sequence (-$V^DPPT$-) that adopts what is known as a type II' turn. While V is a nonpolar residue, K is positively charged and hydrophilic at pH values around physiological conditions (~7.4). Electrostatic forces and hydrophobic interactions, due to the charges on K residues and nonpolar V residues respectively, are the primary intramolecular parameters that can be used to control the folding of the molecule. In the folded state the molecule is facially amphiphilic, having all V residues on one face of the hairpin with K residues on the other. Once the molecule is folded self-assembly is driven by both lateral intramolecular hydrogen bonding and facial hydrophobic interactions. Therefore, these molecules are specifically designed to first fold, and then self-assemble into quaternary structures rich in β-sheet that gives rise to gel properties of the system. Final elastic properties of the self-assembled structure can be tuned by salt concentration. In addition, due to the facial hydrophobic association, temperature can also be used as a parameter in controlling gelation kinetics. Therefore, these molecules are designed to exhibit sol-gel transitions when solution conditions (ionic strength, temperature, pH) are adjusted to physiological levels providing significant potential uses for tissue engineering applications.

Sample Preparation: MAX1 was prepared on amide resin via automated Fmoc based solid phase peptide synthesis employing an ABI 433A peptide synthesizer and HBTU/HOBT activation. The details of peptide preparation are given elsewhere (Schneider supra). Hydrogels are prepared by dissolving the lyophilized peptide first in DI water and the desired final solution conditions achieved by the subsequent addition of buffer and salt containing solution. Bis-trispropane is used for buffering the solution at pH 7.4 with the exception of the x-ray study in which TRIS buffer was used.

Circular Dichroism: CD spectra were collected using an Aviv model 215 spectropolarimeter. Measurements were done either at 20° C. or 37° C. Wavelength scans, between 190 and 260 nm, for 2 wt % MAX1 (pH 7.4, 50 mM BTP) with 0 mM and 150 mM KF solutions were obtained in a 0.01 mm detachable quartz cell. The spectra were taken after 2 hours of dissolution of peptide in DI water and buffer solution. For time dependent studies, mean residue ellipticity θ, was measured at 218 nm. θ was calculated from the equation $θ=θ_{obs}/l/c/r$, where l is the path length of the cell, c is the concentration and r is the number of residues.

Infrared Spectroscopy: IR spectra were taken on a Nicolet Magna-IR 860 spectrometer. Deuterated MAX1*nDCl was prepared by lyophilizing the TFA salt of peptide once from 0.1 M HCl and twice from $D_2O$. Samples were kept in a temperature controlled water bath at 20° C. for two hours before measurements were immediately taken at room temperature in a zinc-selenide flow cell with 30 μm path length. The equipment was operated at 1 $cm^{-1}$ resolution and the spectrum recorded was an average of 100 scans.

Wide Angle X-Ray Scattering: X-Ray spectra of the hydrated gels were collected at the National Synchrotron Light Source, Brookhaven National Laboratory, beamline, X10A. Hydrogel was smeared on Kapton tape just before taking measurements in order to avoid dehydration. Data was collected for 10 minutes on a two dimensional Bruker CCD array. Peptide solutions were buffered with 125 mM TRIS. Measurements were done at room temperature.

Rheology: Dynamic time and frequency sweep experiments were performed in a strain controlled Rheometrics ARES rheometer with 25.0 mm diameter parallel plate geometry and 0.5 mm gap distance. Lyophilized peptide was dissolved in de-ionized water and buffer or cell growth media solution at 10° C. in order to suppress folding and gelation before the sample is loaded into the rheometer. After the sample was loaded, temperature was increased to either 20° C. or 37° C. Standard low viscosity mineral oil was used to insulate the sides of the plate in order to suppress evaporation. Control experiments showed that mineral oil had no effect on rheological measurements. Strain sweep experiments were performed to determine the linear viscoelastic regime in which all rheological experiments were performed. Dynamic time sweep experiments were performed with a frequency and strain of 6 rad/s and 1%, respectively. Frequency sweep experiments were performed with a frequency and strain of 0.1-100 rad/s and 5%, respectively.

Transmission Electron Microscopy: A very thin layer of hydrogel was applied to carbon coated copper grids. The samples were negatively stained by placing a drop of 2 wt/v % of uranyl acetate aqueous solution on the grid. The excess of the solution was blotted with filter paper and the sample subsequently left to dry. To prevent the formation of salt and/or buffer crystals, and to image the individual fibrils clearly, hydrogel with 2 wt % peptide concentration was diluted to ~0.1 wt % in DI water. To disperse the fibrils evenly in the solution, gentle sonication was employed with a tip sonicator. Bright field images of hydrogel nanostructure were taken on a JEOL 2000-FX transmission electron microscope at 200 kV accelerating voltage on both a Gatan CCD camera and Kodak negative films.

Figure 21A:
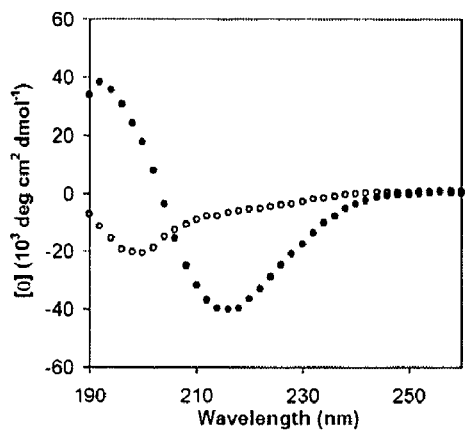
FIG. 21A shows a CD spectra of 2 wt % Max1, pH 7.4 solution with 0 mM (○) and 150 mM (●) KF at 20° C. showing clear beta-sheet formation with salt.

FIG. 21A shows CD spectra of 2 wt % MAX1 solutions at pH 7.4 and 20° C. for different salt concentrations. Both spectra shown were taken after 2 h of dissolution of MAX1 with DI water and buffer solution. The minima at 218 nm for the peptide solution with 150 mM KF indicates that at 2 wt % gelation concentrations MAX1 folds and adopts secondary structure rich in β-sheet. However, 2 wt % MAX1 at identical pH in the absence of salt did not show significant regular secondary structure even after 2 hr, indicating the peptide remains unfolded without the presence of added salt.

Figure 21B:
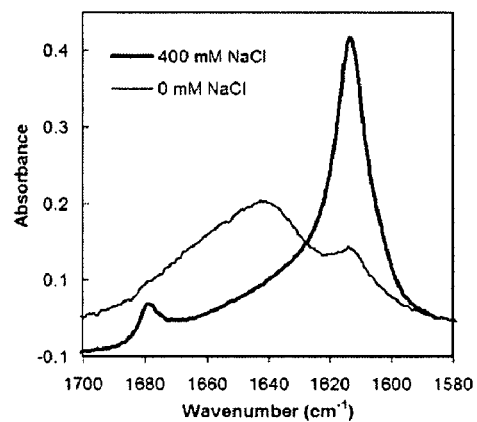
FIG. 21B shows an FTIR spectrum of 2 wt % Max1 solution, pH7.4 with 0 and 400 mM NaCl again showing clear beta-sheet formation with salt addition.

Folding of the peptide molecule to β-hairpin structure and subsequent β-Sheet formation with the presence of salt was also confirmed by FTIR spectroscopy. The FTIR spectrum of MAX1 solution at pH 7.4 and with 400 mM NaCl, between 1580 and 1700 $cm^{-1}$, is given in FIG. 21B. The amide I band for unordered peptide in $D_2O$ is centered around 1645 $cm^{-1}$. The shift of the amide I band from 1644 $cm^{-1}$ to 1614 $cm^{-1}$ suggests that the peptide is in β-sheet conformation in 400 mM NaCl solution. The weak band in the spectrum at 1680 $cm^{-1}$ may be an indication of antiparallel β-sheet structure. For MAX1 solution without NaCl, a very broad spectrum is obtained in the plotted range. The strong band at 1644 $cm^{-1}$ suggests that peptide is in an unordered state. However, the weak band at 1614 $cm^{-1}$ also indicates the presence of a small amount of folded β-hairpin molecules in the solution. We believe that folding of some of MAX1 is due both to the excess buffer salt and relatively high concentration of peptide in the solution. It was shown that peptide concentration has an effect on the kinetics of β-sheet formation. Therefore, this small amount of β-sheet amide I signal, in the context of the high concentration of peptide and lack of gelation is insignificant.

Since MAX1 has a net positive charge at pH 7.4 due to the primary amines on the lysine residues the data suggest that it cannot fold due to the electrostatic repulsion between the strands. Therefore, when the positive charges on the lysine residues are screened by $Cl^-$ ions the intramolecular folding event is favored leading to formation of β-hairpin structure. Increased salt concentrations may also drive the hydrophobic association of residues, which should also contribute to folding and self-assembly. Both CD and FTIR data show that the folding mechanism is triggered by ionic strength of the solution. It has been shown that folding can be triggered by pH and temperature (Pochan, Schneider supra). Similar to the effect of salt, when pH is used as a stimulus, lysine residues are deprotonated at high pH and MAX1 folds. When folded, MAX1 is capable of self-assembly into higher order structures by intermolecular hydrogen bonding and hydrophobic interactions. The kinetics of folding, structure of assembled aggregates, and the consequent hydrogel network properties will be discussed below.

Figure 21C:
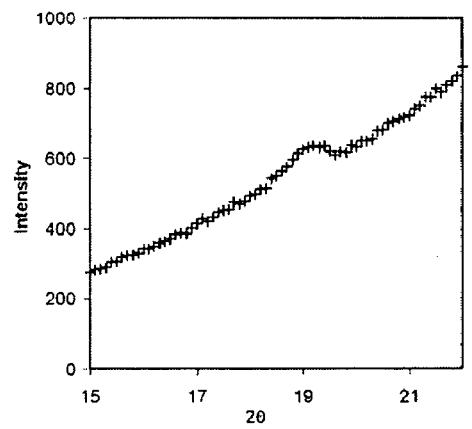
FIG. 21C shows a WAXS spectrum of 3 wt % Max1 solution, pH 7 with 150 mM NaCl. The peak represents a spacing of 4.7 Å, the intermolecular spacing of peptides in a beta-sheet conformation.

Crystallographic β-sheet structure is observed in the final hydrogels using x-ray scattering techniques. FIG. 21C shows the wide-angle curves for a hydrogel consisting of 3 wt % of MAX1 and 150 mM NaCl. The scattering peak corresponds to 4.7 Å. This is the characteristic signature of the interchain distance in β-sheet rich structures. Since the measurements were taken without drying out the hydrogels, the scattering background contribution at high angles due to the water structure is significant.

Figure 22A:
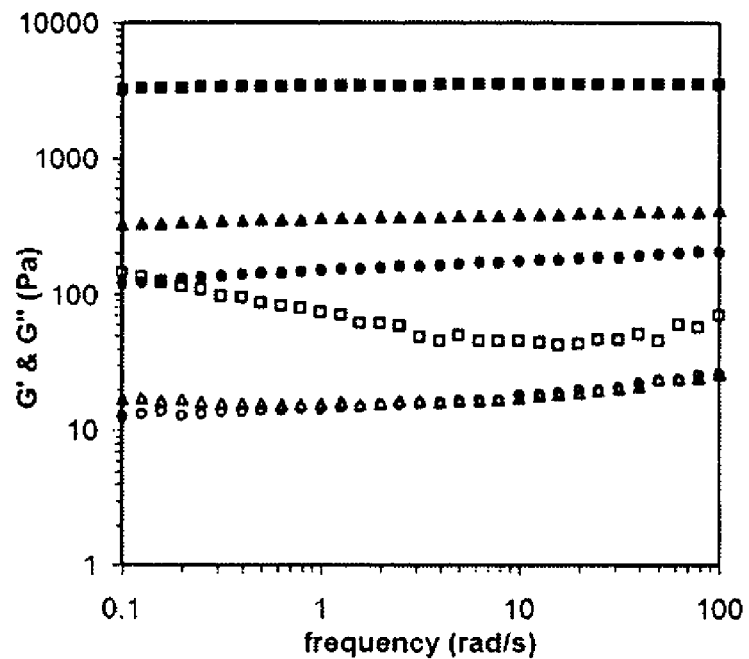
FIG. 22A shows a dynamic frequency sweep (5% strain) of 2 wt % Max1, pH7.4 solution with 20 mM (G':●, G":○), 150 mM (G':▲, G":Δ), and 400 mM (G':■, G":□) NaCl at 20° C. The higher the salt concentration stimulus, the more rigid the hydrogel network.
Figure 22B:
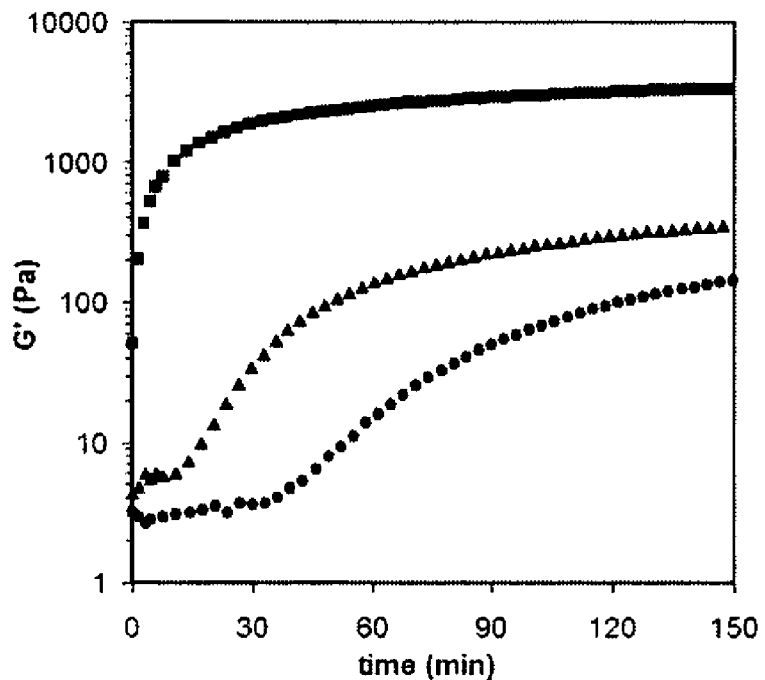
FIG. 22B shows dynamic time sweep (1% strain, 6 rad/s) of 2 wt % Max1 solution with 20 mM (G':●), 150 mM (G':▲) and 400 mM (G':■) NaCl at 20° C. The higher the salt concentration, the more quick the folding and consequent self-assembly, and the more rigid the ultimate hydrogel material.

Hydrogels formed via the intramolecular folding mechanism exhibit rigid viscoelastic properties, even at low concentration of MAX1 peptide, as observed by dynamic oscillatory techniques. FIG. 22A shows frequency sweep measurements from $10^{-1}$ to $10^2$ rad/s for 2 wt % MAX1 peptide solutions at 20, 150 and 400 mM NaCl concentrations. Before the frequency sweep measurements peptide solutions were allowed to gel for 2.5 hr in the rheometer (FIG. 22B). For MAX1 solution with 400 mM NaCl the equilibrium storage modulus (G') is ~3000 Pa. Decreasing salt concentration resulted in the decrease of both G' and loss modulus (G") values. A hydrogel with low rigidity (G'~100 Pa) is formed when only 20 mM NaCl is present in the solution. MAX1 at pH 7.4 without added NaCl did not exhibit any gelation even after 3 hours with G' values approximately 1 Pa (the response of the sample to the applied strain was negligible; torque values were under the detection limit of the instrument leading to insignificant measurements that are not shown). For all three samples with salt, G' values are at least one order of magnitude greater than the G" values. Also, for all NaCl concentrations, the G' values are essentially independent of the frequency in the studied range exhibiting no crossover point between G' and G" at low frequencies. These characteristics are a clear signature of crosslinked networks. The frequency sweep data in FIG. 22A suggests that these solutions form rigid, solid-like hydrogels with properties similar to covalently cross-linked polymer gels.

The spectroscopy data in FIG. 21 suggests that in solutions without salt the electrostatic repulsion of lysine residues keeps the peptide unfolded, thus preventing self-assembly into a network structure. However, once the molecule is folded, self-assembly can occur. Since all valine residues are positioned on one side of the molecule in the folded state, facial hydrophobic dimerization can occur. Additional intermolecular hydrophobic interactions and hydrogen bonding can consequently occur forming an interconnected network.

Importantly, the differences in the hydrogel rigidity with different salt concentrations, as shown in FIG. 22A, reveal that not only can the self-assembly be triggered with ionic strength, but also that the resultant nanostructure can be predictably altered by the ionic strength of the medium. FIG. 22B shows the increase in G' values during self-assembly of MAX1 solution for the same peptide concentration of 2 wt %. This experiment clearly demonstrates the differences in the kinetics of self-assembly and network formation for different salt concentrations. MAX1 solution with 400 mM NaCl shows a rapid increase in its G' value in the first couple of minutes of the self-assembly process while the 20 and 150 mM NaCl solutions stiffened with a relatively slow rate. In fact, the 20 mM NaCl solution G' values do not change significantly for 3000 seconds, remaining around 2-3 Pa. This lag time is shorter for 150 mM (~1000 sec) and does not exist for 400 mM salt solution. FIG. 22B clearly suggests that faster kinetics of folding and self-assembly due to higher ionic strength results in stiffer gels. The order of magnitude differences in stiffness between solutions with the same peptide concentration presumably arise from more highly crosslinked networks due to faster folding and assembly kinetics.

Figure 23A:
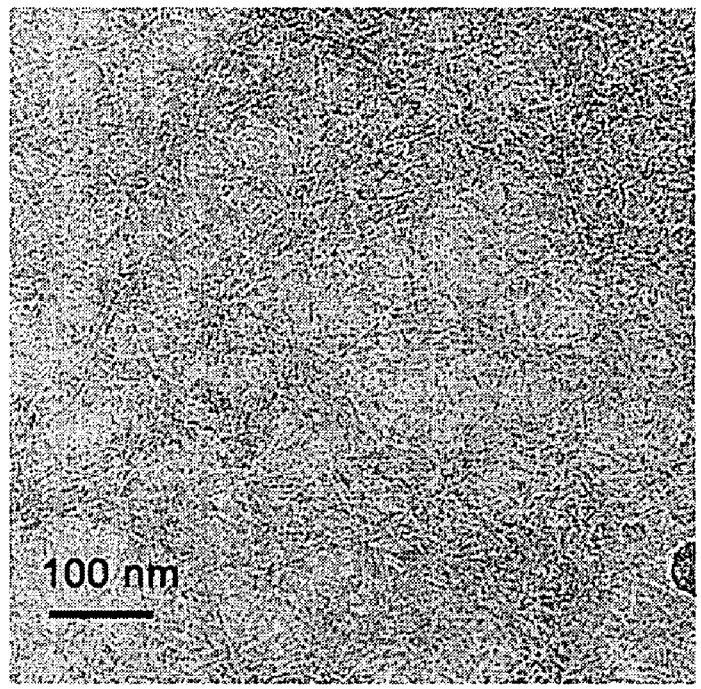
FIG. 23A shows a densely interconnected network of 2 wt % Max1, pH7.4, 400 mM NaCl solution.
Figure 23B:
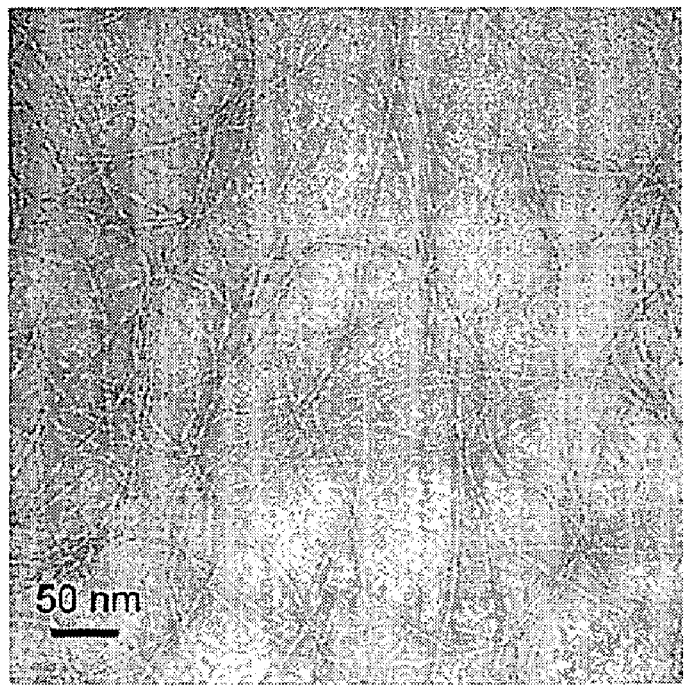
FIG. 23B shows fibrillar assemblies of a diluted hydrogel (final concentration after dilution: ~0.1 wt %). The nanostructure is in agreement with the network structure schematically shown in FIG. 1 and FIG. 24.
Figure 24:
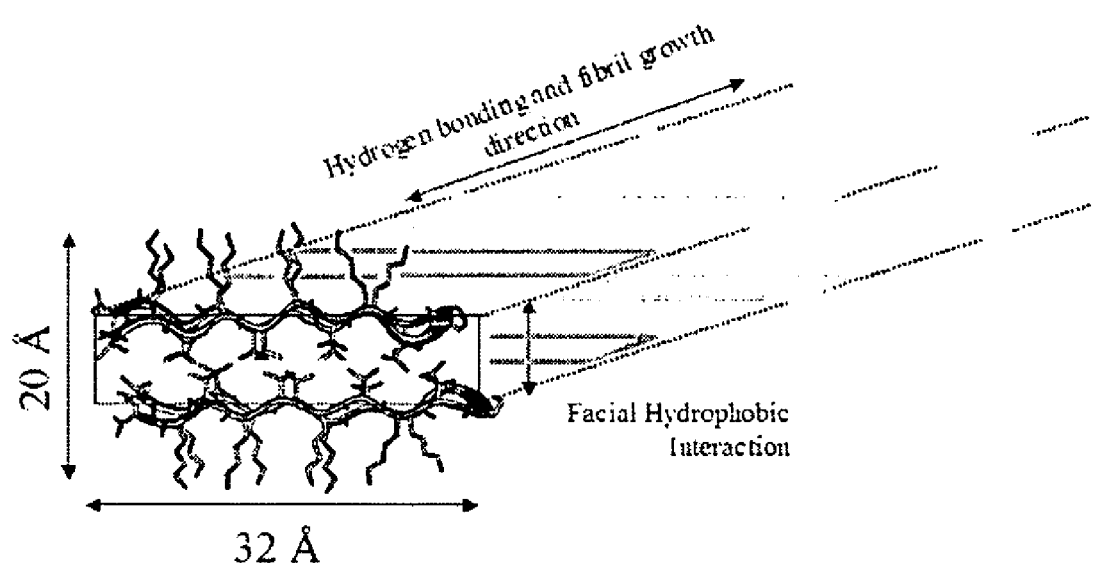
FIG. 24 shows the proposed structure of self-assembled Max1 β-Hairpin molecules in a fibril. The stand axis of the molecule is 32 Å and the cross-section thickness is 20 Å. The long axis of the structure shows the hydrogen bonding and fibril growth direction.

The nanostructure of the hydrogels that results in elastic properties was studied by transmission electron microscopy (TEM). FIG. 23A shows the TEM image of a 2 wt % MAX1 hydrogel network formed at pH 7.4 with 400 mM NaCl. The micrograph reveals the highly interconnected fibrillar network structure at the nanoscale. Although it cannot be directly seen from the TEM micrograph, it is believed that most of the junction points formed during self-assembly are intersecting fibrils and are not simply entanglements of long, nonintersecting fibrils (although certainly entanglements contribute to the modulus). These crosslink points between the fibrils, although not covalent in origin, are permanent and are formed via both hydrogen bonding and hydrophobic interactions. Frequency sweep data, given in FIG. 22A, also supports this view; G' is insensitive to frequency, is an order of magnitude greater than G", and no G" to G' crossover exists. Due to the evaporation of the water prior to imaging and relatively high salt concentration the 2 wt % structure is very dense with some parts of the network embedded in precipitated salt. Therefore, the hydrogel was diluted with DI water by approximately a factor of 20 (to ~0.1 wt % peptide) and a sample was immediately prepared for TEM imaging. FIG. 23B shows the more dilute fibrillar assemblies. Contour lengths of the fibrils are on the order of micrometers. Although drying during sample preparation may cause conformational changes along the fibril axis, micrographs suggest that the self-assembled fibrils are semi-flexible. Importantly, the widths of the fibrils are monodisperse in size and approximately 3 nm. The proposed local self-assembled structure and the dimensions are shown in FIG. 24. Insight II modeling shows that the strand axis of the folded peptide is 32 Å in length and the distance from valine face to lysine face is ~10 Å. The ~3 nm width of the fibrils is in very good agreement with these molecular dimensions. TEM data along with the CD data strongly suggests that MAX1 is in the folded state during the self-assembly process. In the proposed structure in FIG. 24, β-turns are shown to be on the same side of the fibrillar bilayer for simplicity.

CD and rheology results clearly demonstrate that folding and subsequent gelation of β-hairpin molecules can be triggered with a change in salt concentration at pH 7.4. This type of response provides an opportunity for using these materials at physiological conditions. Therefore, the self-assembly and gelation behavior of these molecules was studied at physiological temperature, 37° C. It has been shown that folding and β-sheet formation of MAX1 is temperature dependent. CD studies indicated that for MAX1 the transition temperature from an unordered, random coil state to folded β-sheet structure is around 25° C. at pH 9 and low (20 mM) salt. This transition was shown to be tunable to higher temperatures via changing the hydrophobic character of the assembling peptide.

Figure 25A:
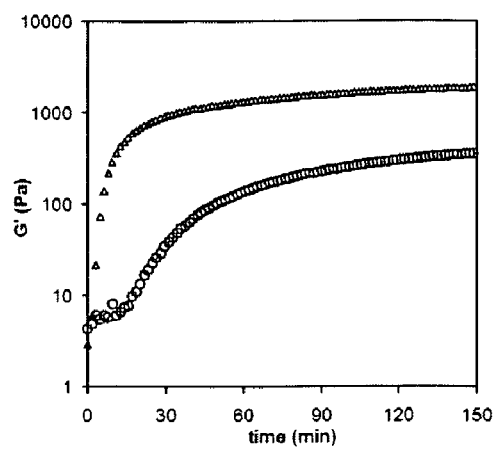
FIG. 25A shows dynamic time sweep data (1% strain, 6 rad/s) of 2 wt % Max1, pH7.4 solution with 150 mM NaCl at 20° C. (G':○) and 37° C. (G':Δ). The higher the temperature, the more quick the assembly and the more rigid the ultimate material.
Figure 25B:
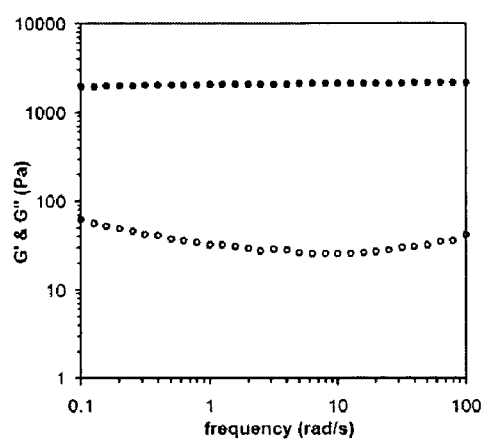
FIG. 25B shows frequency sweep data (5% strain) of hydrogel at 37° C. after 2.5 hours of gelation (G':●, G":○).

To observe the effect of temperature on the self-assembly triggered by ionic strength, gelation was monitored over 2.5 hours by dynamic time sweep experiments at 20° C. and 37° C. In FIG. 25A, the change in G' is plotted as a function of time for 2 wt % MAX1 at pH 7.4 and 150 mM NaCl solution. In both cases MAX1 solutions were initially kept at 10° C. to suppress folding before measurements were taken. An instantaneous increase in G' at 37° C. indicates that the peptide formed a network structure immediately during self-assembly. Contrastingly, at 20° C. the increase in elastic response of the hydrogel is slower showing an insignificant increase in G' for the first 15 minutes of self-assembly. This behavior can be beneficial for potential applications in which one desires a solution with viscous-like behavior at room temperature while exhibiting a fast gelation response when exposed (e.g. injected in vivo) to body temperature and salt concentration. FIG. 25A clearly shows that at physiologically relevant conditions (e.g. pH 7.4, 37° C.), gelation leading to a material that displays useful rigidity occurs in about 10 minutes. The frequency sweep measurement (FIG. 25B) taken at the end of 2.5 hours gelation period at 37° C., indicates that a rigid hydrogel (G'>G") was formed with a G' value around 2000 Pa. During gelation at both temperatures G" values (not shown) were constant and always well below (>1 order of magnitude) the G' values throughout the gelation process. In all samples, even during the early stages of gelation, G'>G". Similar behavior has also been seen in the gelation of biomacromolecules. Similar to ionic strength effect, the formation of stiffer gels assembled at higher temperatures may be due to structural differences at the nanoscale. A faster rate of folding and consequent self-assembly can form network structure more dense in number of junction points leading to higher G' values. This data shows that the rigidity of MAX1 hydrogel can be easily and predictably controlled by either temperature or salt concentration.

Figure 25C:
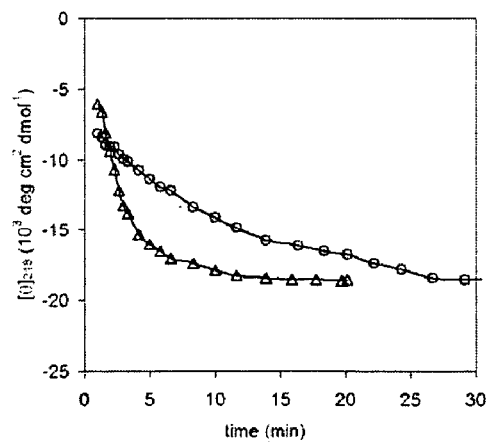
FIG. 25C shows time-dependent mean molar ellipticity at 218 nm ($[\theta]_{218}$) of 2.0 wt % Max1, pH 7.4 with 150 mM NaCl at 20° C. (○) and 37° C. (Δ).

The rate of folding and β-sheet formation of MAX1 peptide was studied by CD. FIG. 25C shows the rate of change of ellipticity, measured at 218 nm, at 20 and 37° C. for 2.0 wt % MAX1, pH 7.4 with 150 mM KF solution. KF is used as the electrolyte since it is optically silent and conducive to CD measurements. CD data reveals that in the early stages of self-assembly, β-sheet formation is very fast at 37° C. The rate of folding during the first 5 minutes is significantly high, reaching a plateau region after 15 minutes. However, at 20° C. the rate of folding is slower. The differences in the kinetics of β-sheet formation and, thus, self-assembly, are in accordance with the rheological measurements shown in FIG. 25A. At 37° C., changes in G' and $\theta_{218}$ values are very rapid at the early stages of self-assembly, while at 20° C. the rates of change of both values are much slower. Therefore, higher storage moduli for gels formed at 37° C. may be attributed to the fast rate of folding. At the initial stages of self-assembly, the high folding rate results in more nucleation sites for β-sheet rich fibril growth, and, consequently, a network is formed with more junction points. This working mechanism is consistent with all of the data obtained thus far.

Figure 26A:
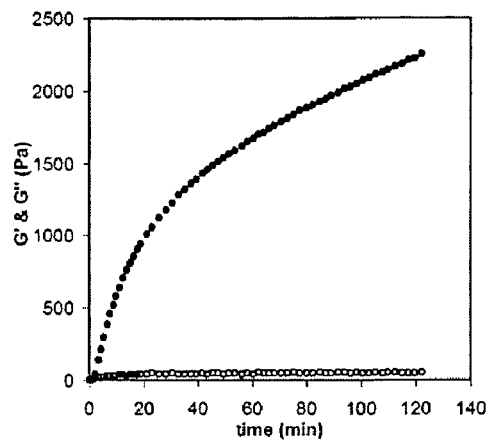
FIG. 26A shows rheology data of gel formation (1% strain, 6 rad/s frequency).
Figure 26B:
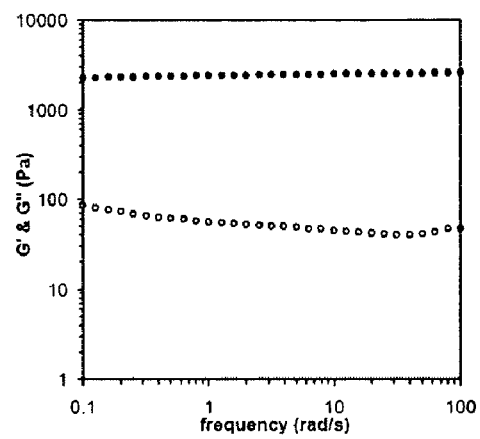
FIG. 26B shows frequency sweep data (5% strain) and FIG. 26C shows G' and G" recovery of hydrogel (1% strain, 6 rad/s frequency) after cessation of high amplitude of strain (1000%, 6 rad/s).
Figure 26C:
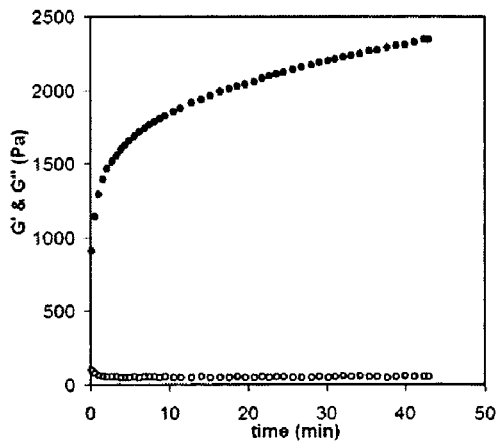

For biomaterials applications it is important to understand the response of MAX1 to biologically relevant conditions. Therefore, the gelation of MAX1 was studied in serum free DMEM cell growth media. FIG. 26A shows G' and G" during the gelation of MAX1 in cell growth media at 37° C. (mammalian cell culturing conditions). At the end of 2 hours of gelation G' and G" values were 2300 and 50 Pa, respectively. It can be seen that the rate of increase in G' value at the end of 2 hours is still significant. To eliminate the effects of evaporation that would result in an increase in peptide concentration and G' value, the dynamic time sweep experiment was stopped after 2 hours of gelation. (This continuing increase in the G' value without showing a final value has also been seen in gelatin gels). Frequency sweep data, shown in FIG. 26B, indicates that the MAX1-cell growth media solution forms a rigid gel with G' values ~2500 Pa. The properties of the frequency sweep data of the media induced hydrogel (G'>10× G", G' independent of frequency) are similar to those shown in FIG. 21A. The response of the hydrogel to significant shear was studied by monitoring recovery of G' after application of high magnitude of strain (1000% at 6 rad/s) to the gelled solution. Since the applied strain is well outside the linear regime, G' and G" values are not shown. FIG. 26C shows that after cessation of shear and the immediate application of 5% strain at 6 rad/s, G' instantaneously recovers almost 50% of its initial value. When recovery data is compared with the gelation data (FIG. 26A) it can be seen that the rate of increase of G' is faster than the rate during initial gelation. This suggests that during the application of high magnitude of strain the physically crosslinked, self-assembled network structure is fractured, resulting in the decrease of connectivity and, thus, elasticity of the material. After the cessation of shear, the network can quickly reheal as manifested in the immediate recovery of significant network stiffness. This experiment demonstrates that these hydrogels are processable and can recover initial rheological properties after being disturbed by external mechanical forces. This ease of processibility and recovery can be advantageous for tissue engineering applications (e.g. in vivo injection).

Rigid hydrogels are formed via folding and self-assembly of β-hairpin peptides. While MAX1 is in a random coil confirmation at physiological pH (7.4), the addition of salt to the solution results in the formation of self-assembled structures rich in β-sheet. Rheological data demonstrates that peptide solutions form gels with G' at least one order of magnitude greater than G". In addition, G' is insensitive to frequency indicating that the network is similar in elastic properties to chemically crosslinked polymer gels. Kinetics of self-assembly as well as storage modulus of the hydrogels, can be tuned by the ionic strength of the peptide solution. The network structure is composed of dense fibrillar assemblies that are crosslinked to each other by physical junction points possibly due to facial hydrophobic interactions and hydrogen bonding. The width of the fibrils is approximately 3 m and this dimension is in a good agreement with the folded state of the hairpins in the self-assembled state. Salt-triggered self-assembly and consequent gelation properties are also tuned by temperature. At 37° C., the kinetics of β-sheet formation and gelation is faster than at 20° C. resulting in stiffer gels. In addition, MAX1 forms rigid and processible hydrogels in cell growth media at physiological conditions. Thus, properly designed peptides can be triggered by salt to intramolecularly fold and consequently intermolecularly assemble into supramolecular structures that result in hydrogels with tunable modulus.

While the foregoing invention has been described in some detail for purposes of clarity and understanding, it will be appreciated by one skilled in the art from a reading of this disclosure that various changes in form and detail can be made without departing from the true scope of the invention and appended claims. All patents and publications cited herein are entirely incorporated herein by reference.

What is claimed is:

1. A peptide hydrogel comprising from about 20 mM to about 400 mM NaCl, wherein the peptide is in a β-hairpin conformation and the pH of the hydrogel is from about 7.0 to about 8.0.

2. A hydrogel according to claim 1, wherein the pH of the hydrogel is about 7.4.

3. A hydrogel according to claim 1, comprising MAX1.

4. A hydrogel according to claim 1, wherein the peptide is selected from the group consisting of MAX2, MAX3, MAX4, MAX5, MAX6, MAX7, MAX8, MAX9, MAX10, MAX11, MAX12, MAX13, MAX14, MAX15, MAX16, MAX17, MAX18, MAX19, MAX20, MAX21, MAX22, MAX23, MAX24, MAX25, MAX26, MAX27, MAX28, MAX29, MAX30, MAX31, MAX32, MAX33, MAX34, MAX35, MAX36, MAX37, MAX38, MAX39, MAX40, MAX41, MAX42, MAX43 and MAX44.

5. A hydrogel according to claim 1, wherein the peptide is selected from the group consisting of $MAXX_1$, $MAXX_2$, $MAXX_3$, $MAXX_4$, $MAXX_5$, $MAXX_6$ and $MAXX_7$.

6. A hydrogel according to claim 1, wherein the peptide comprises a functional moiety.

7. A hydrogel according to claim 5, wherein the functional moiety is selected from the group consisting of cell adhesion epitopes, nuclear localization signals, receptor agonists, receptor antagonists, cholesterol derivatives, peptidomimetics, cyclic peptides, metal chelators, fluorescent probes, spin active probes and small molecule therapeutics.

8. A hydrogel according to claim 1, further comprising a therapeutic agent.

9. A hydrogel according to claim 8, wherein the therapeutic agent is selected from the group consisting of small molecules, peptides, proteins, and cells.

10. A hydrogel according to claim 8, wherein the therapeutic agent comprises cells.

11. A hydrogel according to claim 8, wherein the therapeutic agent comprises an antibody.

12. A hydrogel according to claim 8, wherein the therapeutic agent comprises a pharmaceutical.

13. A hydrogel according to claim 1, wherein the peptide comprises at least one modified amino acid residue.

14. A hydrogel according to claim 1, wherein the peptide comprises at least one D-amino acid.

15. A hydrogel according to claim 1, having a storage modulus in a range from 100 to 5000 Pa.

16. A hydrogel according to claim 1, having a storage modulus in a range from 100 to 10000 Pa.

17. A hydrogel according to claim 1, having a storage modulus in a range from 100 to 50000 Pa.

18. A hydrogel according to claim 1, having a storage modulus in a range from 100 to 100000 Pa.

* * * * *